United States Patent
Moser et al.

(10) Patent No.: US 11,555,202 B2
(45) Date of Patent: Jan. 17, 2023

(54) ELITE EVENT EE-GM5 AND METHODS AND KITS FOR IDENTIFYING SUCH EVENT IN BIOLOGICAL SAMPLES

(71) Applicant: BASF Agricultural Solutions Seed US LLC, Florham Park, NJ (US)

(72) Inventors: Hal Moser, Shafter, CA (US); Michael McCarville, Omaha, NE (US); Maxim Buyse, Zwijnaarde (BE); Filip Slabbinck, Zwijnaarde (BE); Vadim Beilinson, Cary, NC (US); Thomas W Kleven, Muskegon, MI (US); Julia Daum, Morrisville, NC (US); Wendy Aartsen, Zwijnaarde (BE); Veerle Habex, Zwijnaarde (BE)

(73) Assignee: BASF AGRICULTURAL SOLUTIONS SEED US LLC, Florham Park, NJ (US)

( * ) Notice: Subject to any disclaimer, the term of this patent is extended or adjusted under 35 U.S.C. 154(b) by 319 days.

(21) Appl. No.: 16/471,776

(22) PCT Filed: Dec. 22, 2017

(86) PCT No.: PCT/US2017/068121
§ 371 (c)(1),
(2) Date: Jun. 20, 2019

(87) PCT Pub. No.: WO2018/119364
PCT Pub. Date: Jun. 28, 2018

(65) Prior Publication Data
US 2020/0123561 A1    Apr. 23, 2020

Related U.S. Application Data

(60) Provisional application No. 62/481,292, filed on Apr. 4, 2017, provisional application No. 62/437,874, filed on Dec. 22, 2016.

(51) Int. Cl.
| C12N 15/82 | (2006.01) |
| C12N 15/11 | (2006.01) |
| A01N 35/06 | (2006.01) |
| A01N 43/80 | (2006.01) |
| C12Q 1/6895 | (2018.01) |

(52) U.S. Cl.
CPC ......... *C12N 15/8274* (2013.01); *A01N 35/06* (2013.01); *A01N 43/80* (2013.01); *C12N 15/11* (2013.01); *C12N 15/8285* (2013.01); *C12Q 1/6895* (2013.01); *C12Q 2600/158* (2013.01)

(58) Field of Classification Search
CPC .............................................. C12N 15/8274
See application file for complete search history.

(56) References Cited

U.S. PATENT DOCUMENTS 6,245,968 B1 *   6/2001   Boudec ............... C12N 9/0069
                                                          435/320.1
2010/0269230 A1   10/2010  Fincher et al.
2015/0267180 A1   9/2015   Poree et al.
2017/0016018 A1   1/2017   Poree et al.
2017/0166918 A1   6/2017   Dubald et al.

FOREIGN PATENT DOCUMENTS

WO   2007147029 A2   12/2007
WO   2014043435 A1   3/2014
WO   2015135881 A1   9/2015
WO   2015138394 A2   9/2015

OTHER PUBLICATIONS

GenBank Accession XM_009690805, submitted on Jul. 8, 2015.*
GenBank Accession No. XM005149195, submitted on Jul. 26, 2013.*
GenBank Accession No. CP049889, submitted on Mar. 4, 2020.*
Wei et al (2003) PNAS 100:2760-2765.*
International Search Report received from corresponding PCT/US2017/068121, dated Apr. 17, 2018.
Huilin, Yu et al., "Expression of Cry1Ac in transgenic Bt soybean lines and their efficiency in controlling lepidopteran pests," Pest Management Science, vol. 69, No. 12, Dec. 5, 2013, pp. 1326-1333, XP55220399.
GenBank Accession No. AP011946.1, Theileria orientalis strain Shintoku DNA, chromosome 1, nucleotides 588197-588215, Sep. 6, 2012.
Hitoshi Kakidani et al., "Three-Dimensional Modeling of Plant 4-Hydroxyphenylpyruvate Dioxygenase, a Molecular Target of Triketone-Type Herbicides," Journal of Pesticide Science, 2003, vol. 28, pp. 409-415.
Michael Matringe et al., "p-Hydroxyphenylpyruvate dioxygenase inhibitor-resistant plants," Pest Management Science, 2005, vol. 61, pp. 269-276.
GenBank Accession No. AP011946, Dec. 15, 2006.
National Geographic Editorial Team, "Creating synthetic DNA that is capable of evolving," Apr. 25, 2012, National Geographic, http://www.nationalgeographic.es/ciencia/crean-un-adn-sintetico-capaz-de_evolucionar.
Daniel Villalobos, "First organism with artificial DNA succeeds in reproducing", May 8, 2014, FayerWayer, https://www.fayerwayer.com/2014/05/primer-organismo-con-adn-arlincial-logra-reproducirse/.

* cited by examiner

Primary Examiner — Mykola V. Kovalenko
(74) Attorney, Agent, or Firm — ArentFox Schiff LLP

(57) ABSTRACT

The invention provides specific transgenic soybean plants, plant material and seeds, characterized in that these products harbor a specific nematode resistance and herbicide tolerance transformation event at a specific location in the soybean genome. Tools are also provided which allow rapid and unequivocal identification of the event in biological samples.

26 Claims, 9 Drawing Sheets

Specification includes a Sequence Listing.

ELITE EVENT EE-GM5 AND METHODS AND KITS FOR IDENTIFYING SUCH EVENT IN BIOLOGICAL SAMPLES

CROSS REFERENCE TO RELATED APPLICATIONS

This application is a National Stage entry of International Application No. PCT/US2017/068121, filed Dec. 22, 2017, which claims the benefit of U.S. Provisional Application Ser. No. 62/437,874, filed Dec. 22, 2016, U.S. Provisional Application Ser. No. 62/481,292, filed Apr. 4, 2017, the contents of which are herein incorporated by reference in their entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000052-038000_ST25.txt" created on 1 Jun. 2019, and 75,895 bytes in size) is submitted concurrently with the instant application, and the entire contents of the Sequence Listing are incorporated herein by reference.

BACKGROUND

Field of the Invention

This invention relates to novel nucleic acids and transgenic soybean plants, plant material and seeds, characterized by harboring a specific transformation event, particularly by the presence of genes conferring nematode resistance and herbicide tolerance, at a specific location in the soybean genome. The soybean plants of the invention combine the nematode resistance and herbicide tolerance phenotype with an agronomic performance, genetic stability and functionality in different genetic backgrounds equivalent to the corresponding non-transformed soybean genetic background in the absence of HPPD inhibitor herbicide(s) or nematode infestation. This invention further provides methods and kits for identifying the presence of plant material comprising specifically transformation event EE-GM5 in biological samples.

Description of Related Art

The phenotypic expression of a transgene in a plant is determined both by the structure of the gene or genes itself and by its or their location in the plant genome. At the same time the presence of the transgenes or "inserted T-DNA" at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, introgression, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary.

Planting nematode resistant and herbicide tolerant soybean EE-GM5 varieties provides growers with new options for nematode and weed control, using HPPD inhibitor herbicides such as isoxaflutole (IFT), topramezone or mesotrione (MST) herbicide. HPPD inhibitor herbicides offer an alternative weed control option for the soybean grower to help manage problem weed species and as an alternative mode of action tool to help slow the spread of herbicide resistant weeds.

Soybean cyst nematode (SCN) *Heterodera glycines* (Ichinohe), a worldwide problem for soybean production, is a continuing threat to producers. Since its first detection in the US in 1954 from a single county in North Carolina, SCN has spread to nearly every soybean-producing state in the United States and is estimated to cause more than $1.2 billion in annual yield losses in the US, making it the most damaging soybean pathogen there. SCN was first detected in Brazil in the early 1990s and has since spread throughout South America, and is one of the most important pathogens in Brazil causing losses in practically all Brazilian growing regions. Similarly, SCN continues to spread across soybean producing regions of China with detection in 15 provinces and yield loss estimates of more than $120 million. A multi-year study in the state of Iowa, USA (2001 to 2015) where almost all SCN-resistant soybean varieties contain SCN resistance from PI 88788, found that the virulence of SCN populations increased over the years, resulting in increased end-of-season SCN population densities and reduced yields of SCN-resistant soybean varieties with the PI88788 source of resistance (Mitchum (2016), Phytopathology 106(12):1444-1450, Allen et al. (2017) Plant Health Progr. 18:19-27, Arias et al. (2017) www.researchgate.net/publication/266907703_RESISTANCE_TO_SOYBEAN_CYST_NEMATODE_GE NETICS_AND_BREEDING_IN_BRAZIL; McCarville et al. (2017) Plant Health Progress 18:146-155).

The root lesion nematode *Pratylenchus brachyurus* has become an increasingly important pathogen of soybean. It has a broad host range and is widely distributed in tropical and subtropical regions, especially in Brazil, Africa, and the Southern United States. *Pratylenchus brachyurus* has become a concern among cotton and soybean growers in the Brazilian Cerrado region and is considered the main nematode pathogen of soybean in the region. In soybean, this nematode can reduce yields 30 to 50%, with greater damage being observed on sandy soils. The use of resistant soybean varieties would be the best way to control this nematode, however, *P. brachyurus*-resistant soybean varieties have not been identified to date. Although several soybean genotypes have been studied for *Pratylenchus brachyurus* resistance, and some cultivars identified with increased tolerance, breeding resistant cultivars against *P. brachyurus* is difficult due to the fact that this nematode is polyphagous and lacks a close interaction with its hosts (Machado (2014) Current Agricultural Science and Technology 20:26-35; Antonio et al. (2012) Soil productivity losses in area infested by the nematoid of the root lesions in Vera, Mont. In: Brazilian Congress of Soy, 6, 2012, Cuiabá. Abstracts. Londrina: Embrapa Soja, 4pp; Rios et al. (2016) Ciência Rural 46:580-584; Lima et al., 2017, Chapter 6 in the book: Soybean—The Basis of Yield, Biomass and Productivity; Edited by Minobu Kasai, ISBN 978-953-51-3118-2, Print ISBN 978-953-51-3117-5, InTech; Inomoto et al. (2011) Sucessão de culturas sob pivô central para controle de fitonematoides: variação populacional, patogenicidade e estimativa de perdas. Tropical Plant Pathology 36:178-185).

It is known that protecting plants against nematodes such as SCN can help plants to better cope with other stresses such as soil composition/content, weather conditions, pathogen stress, herbicide applications, etc. Particularly when such other stresses give a phenotype that is easily seen, such as chlorosis/yellowing of leaves, the effect of SCN control is more easy to see while otherwise often not "visible". E.g., when soybean plants have Sudden Death Syndrome (SDS) or Iron Deficiency Chlorosis (IDC), protection from SCN will result in plants that are greener or have less severe SDS/IDC symptoms. Despite extensive research and variety screening efforts, iron deficiency remains a challenge in large soybean production areas in the North Central U.S. The importance of this problem has increased due to expanded soybean production on soils susceptible to iron deficiency and to possible interactions with cropping system changes. Iron deficiency occurs in soils with high pH and carbonates, but the expression of iron deficiency is highly variable in space due to interactions with spatially variable soil properties such as moisture content, salinity, availability of iron, and other micronutrient and metal concentrations. Further, iron deficiency expression interacts with biotic factors such as nitrogen fixation, pests, diseases and with management induced stresses such as herbicide application. Variety selection is the most important means to manage iron deficiency, but selecting varieties is complicated by a large genotype by environment interaction related to chlorosis tolerance (Hansen et al. (2004) Soil Sci. Plant Nutr. 50(7):983-987).

Sudden death syndrome (SDS) of soybean was first discovered in 1971 in Arkansas and since then has been confirmed throughout most soybean-growing areas of the USA. SDS is a fungal disease that also occurs in a disease complex with the soybean cyst nematode (SCN). SDS is among the most devastating soil-borne diseases of soybean in the USA. When this disease occurs in the presence of SCN, symptoms occur earlier and are more severe. SDS is caused by soil-borne fungi within a group of the *Fusarium solani* species complex. In North America, *Fusarium virguliforme*, formerly *Fusarium solani* f. sp. *glycines*, is the causal agent. In South America, *F. brasiliense, F. cuneirostrum, F. tucumaniae*, and *F. virguliforme* cause SDS symptoms. Although soybean cultivars that are less susceptible to SDS have been developed, no highly resistant cultivars are available. The fungus may infect roots of soybean seedlings soon after planting, but above ground symptoms of SDS rarely appear until soybean plants have reached reproductive stages. The fungus produces toxins in the roots that are translocated to the leaves. The first noticeable symptoms of SDS are yellowing and defoliation of upper leaves. If the disease develops early in the season, flowers and young pods will abort. When the disease develops later, the plant will produce fewer seeds per pod or smaller seeds. The earlier severe disease develops, the more the yield is reduced. Because the SDS fungus can persist in soil for long periods, larger areas of a field will show symptoms of the disease each growing season until most of the field is affected (Westphal et al. (2008). Sudden Death Syndrome of Soybean. The Plant Health Instructor. DOI:10.1094/PHI-I-2008-0102-01, www.apsnet.org/edcenter/intropp/lessons/fungi/ascomycetes/Pages/SuddenDeath.aspx.

Currently, no soybean plants genetically engineered for nematode resistance are commercialized. Soybean plants comprising one or more herbicide tolerance genes have been disclosed in the art. WO2006/130436 describes a glyphosate tolerant soybean event comprising an epsps gene, and WO2011/034704 describes a dicamba-tolerant soybean event. WO2012/082548 describes soybean plants comprising both an hppd and pat gene. WO2011/063411 describes a soybean event with tolerance to HPPD inhibitors and glyphosate, while WO2011/063413 describes soybean plants with tolerance to HPPD inhibitors, glufosinate and glyphosate. WO2011/066384 describes a soybean event with tolerance to 2,4-D and glufosinate, while WO2012/075426 describes a soybean event with tolerance to 2,4-D, glufosinate and glyphosate and WO2017/059795 describes a soybean event with tolerance to glyphosate. WO2009/064652 describes a soybean event with resistance to lepidopteran insects, and WO2013/016527 describes a soybean event with resistance to lepidopteran insects and glufosinate tolerance.

HPPD genes and proteins that confer improved tolerance to HPPD inhibitor herbicides have been disclosed e.g., in WO2015138394, WO2015135881, WO2014043435, and nematicidal activity of Cry proteins has been described in, e.g., WO2010027805, WO2010027809, WO2010027804, WO2010027799, WO2010027808 and in WO2007147029.

None of the prior art disclosures teach or suggest an elite event in soybean comprising a nematode-active Cry gene, and certainly not an elite event in soybean comprising a nematode-active Cry gene combined with a gene conferring tolerance to HPPD inhibitors.

It is known in the art that getting a commercial elite transformation event in soybean plants with acceptable agronomic performance is by no means straightforward.

SUMMARY

This invention provides a nucleic acid encoding a Cry14Ab-1 protein, such as the cry14Ab-1.b coding sequence of SEQ ID No. 7 or a sequence encoding a nematicidal Cry14Ab protein having at least 95, 96, 97, 98, or at least 99% sequence identity to SEQ ID No.7. Also provided herein is a nucleic acid encoding an HPPD-4 protein, such as the hppdPf-4Pa coding sequence of SEQ ID No. 9 or a sequence having at least 95, 96, 97, 98, or at least 99% sequence identity to SEQ ID No. 9, wherein said sequence encodes an HPPD protein providing tolerance to HPPD inhibitor herbicides when expressed in a plant. Also provided herein are a chimeric cry14Ab-1.b gene comprising the sequence of SEQ ID No. 11 from nucleotide position 131 to nucleotide position 5276, or the complement thereof, or a chimeric cry14Ab-1.b gene comprising the sequence of SEQ ID No. 11 from nucleotide position 412 to nucleotide position 3969 operably-linked to a plant-expressible promoter, or a sequence encoding a nematicidal Cry14Ab protein having at least 95, 96, 97, 98, or at least 99% sequence identity to the sequence of SEQ ID No. 11 from nucleotide position 131 to nucleotide position 5276, or the complement thereof, or to the sequence of SEQ ID No. 11 from nucleotide position 412 to nucleotide position 3969 (when operably-linked to a plant-expressible promoter). Further provided herein is a chimeric hppdPf-4 Pa gene comprising the sequence of SEQ ID No. 11 from nucleotide position 5382 to nucleotide position 7459, or the complement thereof, or comprising the sequence of SEQ ID No. 11 from nucleotide position 5589 to nucleotide position 6665 operably-linked to a plant-expressible promoter, or a sequence having at least 95, 96, 97, 98, or at least 99% sequence identity to the sequence of SEQ ID No. 11 from nucleotide position 5382 to nucleotide position 7459 or its complement, or to the sequence of SEQ ID No. 11 from nucleotide position 5589 to nucleotide position 6665 (when operably-linked to a plant-expressible promoter); wherein said sequence encodes an HPPD protein providing tolerance to HPPD inhibitor herbicides when expressed in a plant, as well as a nucleic acid comprising said chimeric cry14Ab-1.b gene and said chimeric hppdPf-4 Pa gene. These nucleic acids or genes are useful to transform plants such as soybean, cotton, corn, rice, oilseed rape, and wheat, so that they control nematodes and/or have HPPD inhibitor herbicide tolerance.

Also provided herein is a chimeric DNA molecule comprising the nucleotide sequence of SEQ ID No. 11 from nucleotide position 131 to nucleotide position 7941, or a nucleotide sequence having at least 95%, at least 96%, at least 97%, at least 98%, or at least 99% sequence identity thereto. In one embodiment, this DNA molecule encodes a protein tolerant to an HPPD inhibitor and a protein negatively affecting plant pest nematodes, such as SCN, RKN or *Pratylenchus* spp. nematodes. In one embodiment, this chimeric DNA molecule encodes the protein of SEQ ID No. 8 or a nematode control protein at least 99% identical thereto and the protein of SEQ ID No. 10, or an HPPD inhibitor tolerant protein at least 99% identical thereto. Also provided are plants, seeds, or cells, such as soybean plants, seeds, or cells, transformed to contain such a DNA molecule, and the use of such a DNA molecule to render plants or seeds, such as soybean plants or seeds, resistant to nematodes and tolerant to HPPD inhibitor herbicides.

The present invention relates to a transgenic soybean plant, plant part, seed, cell or tissue thereof, comprising, stably integrated into its genome, an expression cassette which comprises a nematode resistance gene comprising the coding sequence of the cry14Ab-1.b gene and a herbicide tolerance gene comprising the coding sequence of the hppdPf-4 Pa gene (both as described in Example 1.1 herein and as represented in SEQ ID No. 7 and 9, respectively), which provide resistance to plant parasitic nematodes such as soybean cyst nematode and tolerance to an HPPD inhibitor herbicides such as isoxaflutole, topramezone or mesotrione. In the absence of HPPD inhibitor herbicide and nematode pressure, such soybean plant has an agronomic performance which is substantially equivalent to the non-transgenic isogenic line. When encountering soybean cyst nematode (SCN) pressure affecting plant performance in the field, the plants of the invention will have a superior agronomic phenotype compared to a non-transgenic plant. Also, in the presence of weeds, after application of an HPPD inhibitor herbicide to which tolerance is provided, the plants of the invention will have a superior agronomic phenotype compared to plants that were not treated with herbicides.

According to the present invention the soybean plant or seed, cells or tissues thereof comprise elite event EE-GM5. In one embodiment, elite event EE-GM5 comprises the sequence of any one of SEQ ID No. 1, 3, 5, or 24, or the sequence of any one of SEQ ID No. 2, 4, 6, or 25, or any sequences essentially similar thereto. In one embodiment, EE-GM5 comprises the sequence of any one of SEQ ID No. 1, 3, 5 or 24 and the sequence of any one of SEQ ID No. 2, 4, 6, or 25, or any sequences essentially similar thereto, and the cry14Ab-1.b coding sequence of SEQ ID No. 7 and the hppdPf-4 Pa coding sequence of SEQ ID No. 9, or sequences essentially similar thereto. In one embodiment, elite event EE-GM5 is a T-DNA inserted at a specific position in the soybean genome, as is contained in reference seed deposited at the ATCC under deposit number PTA-123625. In one embodiment, such T-DNA in EE-GM5 comprises a chimeric Cry14Ab-1-encoding gene and an HPPD-4-encoding gene. In another embodiment, said event is characterized by the 5' junction sequence of SEQ ID No. 1 or 3, or by the 3' junction sequence of SEQ ID No. 2 or 4; or by the 5' junction sequence of SEQ ID No. 1 or 3, and by the 3' junction sequence of SEQ ID No. 2 or 4. In one embodiment, genomic DNA containing EE-GM5, when analyzed using a polymerase chain reaction ("PCR" herein) with two primers comprising the nucleotide sequence of SEQ ID No. 12 and SEQ ID No. 13 respectively, yields a DNA fragment of 85 bp. In one embodiment, genomic DNA containing EE-GM5, when analyzed using PCR with two primers comprising the nucleotide sequence of SEQ ID No. 18 and SEQ ID No. 19 respectively, yields a DNA fragment of 84 bp.

In one embodiment herein is provided a soybean plant, cell, plant part, seed or progeny thereof, each comprising elite event EE-GM5 in its genome, reference seed comprising said event having been deposited at the ATCC under deposit number PTA-123625. In one embodiment, a plant or seed comprising EE-GM5 is obtainable by propagation of and/or breeding with a soybean plant grown from the seed deposited at the ATCC under deposit number PTA-123625.

More specifically, the present invention relates to a transgenic soybean plant, plant part, pollen, seed, cell or tissue thereof, the genomic DNA of which is characterized by the fact that, when analyzed in PCR as described herein, using at least two primers directed to the region formed by a part of the 5' or 3' T-DNA flanking region of EE-GM5 and part of the inserted T-DNA, a fragment is amplified that is specific for event EE-GM5. The primers may be directed against the 3' T-DNA flanking region within SEQ ID NO: 6 or SEQ ID NO. 25 or soybean plant genomic DNA downstream thereof and contiguous therewith and the inserted T-DNA upstream thereof and contiguous therewith. The primers may also be directed against the 5' T-DNA flanking region within SEQ ID NO: 5 or SEQ ID NO. 24 or soybean plant genomic DNA upstream thereof and contiguous therewith and the inserted T-DNA downstream of and contiguous therewith. In one embodiment, such primers comprise or consist (essentially) of the nucleotide sequence of SEQ ID NO: 12 and SEQ ID NO: 13, or of SEQ ID No. 18 and SEQ ID No. 19, or of SEQ ID NO. 26 and SEQ ID NO. 28, or of SEQ ID NO. 27 and SEQ ID NO. 29, respectively (e.g., a primer pair comprising a primer containing at its extreme 3' end the nucleotide sequence of SEQ ID NO: 12 and a primer containing at its extreme 3' end the nucleotide sequence of SEQ ID NO: 13, or a primer pair comprising a primer containing at its extreme 3' end the nucleotide sequence of SEQ ID No. 18 and a primer containing at its extreme 3' end the nucleotide sequence of SEQ ID No. 19, or a primer pair comprising a primer containing at its extreme 3' end the nucleotide sequence of SEQ ID NO: 26 and a primer containing at its extreme 3' end the nucleotide sequence of SEQ ID NO: 28, or a primer pair comprising a primer containing at its extreme 3' end the nucleotide sequence of SEQ ID NO: 27 and a primer containing at its extreme 3' end the nucleotide sequence of SEQ ID NO: 29), and yield a DNA fragment of between 50 and 1000 bp, such as a fragment of 85 bp or of 84 bp.

Reference seed comprising the elite event of the invention has been deposited at the ATCC under accession number PTA-123625. One embodiment of the invention is the elite event EE-GM5 as contained in seed deposited under accession number PTA-123625, which when introduced in a soybean plant will provide resistance to nematodes and tolerance to herbicides, particularly resistance to soybean cyst nematode (*Heterodera glycines*, "SCN" herein) and/or lesion nematode (lesion nematode as used herein refers to *Pratylenchus* spp. soybean pest nematodes, including but not limited to *Pratylenchus brachyurus*) and tolerance to HPPD inhibitors such as isoxaflutole, topramezone or mesotrione. The plants with EE-GM5 of this invention also control root knot nematode (root-knot nematode as used herein refers to *Meloidogyne* spp. soybean pest nematodes, including but not limited to *Meloidogyne incognita, Meloidogyne arenaria, Meloidogyne hapla*, or *Meloidogyne javanica*, or any combination thereof), reniform nematode (*Rotylenchulus reniformis*) and Lance nematode (*Hoplolaimus* spp. such as *H. columbus, H. galeatus*, and *H. magnistylus*). Included in this invention are minor variants of this event such as a soybean event with HPPD inhibitor tolerance and SCN nematode resistance that has a nucleotide sequence with at least 90%, at least 95%, at least 98%, at least 99%, at least 99.5%, or at least 99.9% sequence identity to the nucleotide sequence of EE-GM5 as contained in the seed deposited at the ATCC under deposit number PTA-123625, or a soybean event with HPPD inhibitor tolerance and SCN nematode resistance that has a nucleotide sequence differing in 1 to 200, 1 to 150, 1 to 100, 1 to 75, 1 to 50, 1 to 30, 1 to 20, 1 to 10, or 1 to 5 nucleotides from the nucleotide sequence of EE-GM5 as contained in the deposited seed of ATCC deposit PTA-123625, or that has a nucleotide sequence differing in 1 to 200, 1 to 150, 1 to 100, 1 to 75, 1 to 50, 1 to 30, 1 to 20, 1 to 10, or 1 to 5 nucleotides from the nucleotide sequence formed by the following consecutive nucleotide sequences (5' to 3'): SEQ ID No. 5 or SEQ ID No. 24, SEQ ID No. 11 from nucleotide position 188 to nucleotide position 7101, and SEQ ID No. 6 or SEQ ID No. 25. In one embodiment, EE-GM5 comprises a nucleotide sequence with at least 95%, at least 96%, at least 97%, at least 98%, at least 99%, at least 99.5%, or at least 99.9% sequence identity to the sequence formed by the following consecutive nucleotide sequences (5' to 3'): SEQ ID No. 5 or 24, SEQ ID No. 11 from nucleotide position 188 to nucleotide position 7101, and SEQ ID No. 6 or 25. Due to natural genetic variation, single DNA base differences and small insertions and deletions in homologous DNA sequences (e.g., single-nucleotide polymorphisms (SNPs)) are commonly found in plants of the same species (Zhu et al. (2003) Genetics 163:1123-1134).

The seed of ATCC deposit number PTA-123625, is a pure seed lot of transgenic seeds homozygous for elite event EE-GM5 of the invention, which will grow into nematode resistant plants, whereby the plants are also tolerant to an HPPD inhibitor such as isoxaflutole, topramezone or mesotrione.

The seed or progeny seed obtainable from the deposited seed (e.g., following crossing with other soybean plants with a different genetic background) can be sown and the growing plants can be treated with an HPPD inhibitor such as isoxaflutole, topramezone or mesotrione as described herein or can be tested for the presence of EE-GM5 as described herein to obtain plants comprising the elite event of the invention. The invention further relates to cells, seeds, tissues, progeny, and descendants from a plant comprising the elite event of the invention grown from the seed deposited at the ATCC having accession number PTA-123625. The invention further relates to plants obtainable from (such as by propagation of and/or breeding with) a soybean plant comprising the elite event of the invention (such as a plant grown from the seed deposited at the ATCC having accession number PTA-123625, or a plant comprising the HPPD-4 coding sequence of SEQ ID No. 9 and the cry14Ab-1.b coding sequence of SEQ ID No. 7 located between the sequence of SEQ ID No. 1, 3 or 5 and the sequence of SEQ ID No. 2, 4 or 6, or a plant comprising the hppdPf-4 Pa coding sequence of SEQ ID No. 9 and the cry14Ab-1.b coding sequence of SEQ ID No. 7 located between any one of the sequence of SEQ ID No. 1, 3, 5, or 24 and the sequence of any one of SEQ ID No. 2, 4, 6, or 25). The invention also relates to progeny plants and seeds obtained from the above plants or seed and that comprise the sequence of SEQ ID No. 1 and the sequence of SEQ ID No. 2, or the sequence of SEQ ID No. 3 and the sequence of SEQ ID No. 4, or the sequence of SEQ ID No. 5 and the sequence of SEQ ID No. 6, or the sequence of SEQ ID No. 24 and the sequence of SEQ ID No. 25.

The invention further relates to a method for identifying a transgenic plant, or cells or tissues thereof, comprising elite event EE-GM5 which method is based on identifying the presence of characterizing DNA sequences or amino acids encoded by such DNA sequences in the transgenic plant, cells or tissues. According to a preferred embodiment of the invention, such characterizing DNA sequences are sequences of 15 bp or at least 15 bp, preferably 20 bp or at least 20 bp, most preferably 30 bp or more which comprise the insertion site of the event, i.e., a sequence containing both a part of the inserted T-DNA containing an HPPD inhibitor and nematode resistance transgene and a part of the 5' or 3' T-DNA flanking region contiguous therewith that extends into the soybean plant genome, allowing specific identification of the elite event. The invention also relates to plants, seeds and cells comprising the event EE-GM5 as identified herein.

The present invention further relates to methods for identifying elite event EE-GM5 in biological samples, which methods are based on primer pairs or probes which specifically recognize the 5' and/or 3' T-DNA flanking sequence and the inserted T-DNA sequence contiguous therewith in EE-GM5. Any other methods to identify EE-GM5, e.g., to identify its specific characterizing sequences, are also included herein, such as whole or partial (directed) genome sequencing.

More specifically, the invention relates to a method for identifying elite event EE-GM5 in biological samples comprising amplifying a sequence of a nucleic acid present in said biological samples, using a polymerase chain reaction with at least two primers, or a polymerase chain reaction with at least two primers and a probe, wherein one of these primers recognizes the 5' or 3' T-DNA flanking region in EE-GM5, the other primer recognizes a sequence within the T-DNA comprising the herbicide tolerance and nematode resistance genes that is contiguous with said 5' or 3' T-DNA flanking region, preferably to obtain a DNA fragment of 50 to 1000 bp in size. In one embodiment, a first primer recognizes the 5' T-DNA flanking region in EE-GM5, and a second primer recognizes a sequence within the T-DNA comprising the herbicide tolerance and nematode resistance genes that is contiguous with and downstream of said 5' T-DNA flanking region, or a first primer recognizes the 3' T-DNA flanking region in EE-GM5, and a second primer recognizes a sequence within the T-DNA comprising the herbicide tolerance and nematode resistance genes that is contiguous with and upstream of said 3' T-DNA flanking region, to obtain a DNA fragment characteristic for elite event EE-GM5. In one embodiment, said polymerase chain reaction method further comprises the use of a probe that recognizes the DNA amplified by said primers, e.g., the junction DNA comprising part of the inserted T-DNA and part of the DNA flanking said T-DNA in EE-GM5 (at either the 5' or 3' side of the event, as applicable, such as a probe comprising the nucleotide sequence of SEQ ID No. 14 or 20 herein, or their complement), so as to detect the amplification product produced by said primers. The primers may recognize a sequence within the 5' T-DNA flanking region of EE-GM5 (SEQ ID No. 5, from nucleotide position 1 to nucleotide position 166, or SEQ ID No. 24 from nucleotide position 1 to nucleotide position 1113) or within the 3' T-DNA flanking region of EE-GM5 (complement of SEQ ID No. 6 from nucleotide position 359 to nucleotide position 691, or SEQ ID No. 25 from nucleotide position 359 to nucleotide position 1449) and a sequence within the inserted T-DNA (SEQ ID No. 5 from nucleotide position 167 to 353, or SEQ ID No. 6 from nucleotide position 1 to nucleotide position 358, or SEQ ID No. 23 from nucleotide position 1114 to 8572, or the complement thereof), respectively. The primer recognizing the 5' or 3' T-DNA flanking region may comprise the nucleotide sequence of SEQ ID No. 13, SEQ ID No. 19, SEQ ID No. 26 or SEQ ID No. 27, and the primer recognizing a sequence within the inserted T-DNA comprising nematode resistance and herbicide tolerance genes may comprise the nucleotide sequence of SEQ ID No. 12, SEQ ID No. 18, SEQ ID No. 28 or SEQ ID No. 29 described herein. This invention also relates to any event-specific primer pair and the specific DNA amplified using such primer pair, as can be obtained by a person of ordinary skill in the art or as can be obtained from commercial sources from the EE-GM5 event sequences provided herein or contained in the seed deposited at the ATCC under accession number PTA-123625.

The present invention more specifically relates to a method for identifying elite event EE-GM5 in biological samples, which method comprises amplifying a sequence of a nucleic acid present in a biological sample, using a polymerase chain reaction with two primers comprising or consisting (essentially) of the nucleotide sequence of SEQ ID No. 12 and SEQ ID No. 13 respectively, to obtain a DNA fragment of 85 bp or with two primers comprising or consisting (essentially) of the nucleotide sequence of SEQ ID No. 18 and SEQ ID No. 19 respectively, to obtain a DNA fragment of 84 bp. Also plants comprising the thus-identified elite event EE-GM5 are included in this invention.

The present invention further relates to the specific T-DNA flanking sequences of EE-GM5 described herein, which can be used to develop specific identification methods for EE-GM5 in biological samples. Such specific T-DNA flanking sequences may also be used as reference control material in identification assays. More particularly, the invention relates to the 5' and/or 3' T-DNA flanking regions of EE-GM5 which can be used for the development of specific primers and probes as further described herein. Also suitable as reference material are nucleic acid molecules, preferably of about 150-850 bp, comprising the sequence which can be amplified by primers comprising or consisting (essentially) of the nucleotide sequence of SEQ ID No. 12 and SEQ ID No. 13 or of SEQ ID No. 18 and SEQ ID No. 19.

The invention further relates to identification methods for the presence of EE-GM5 in biological samples based on the use of such specific primers or probes. Primers may comprise, consist or consist essentially of a nucleotide sequence of 17 to about 200 consecutive nucleotides selected from the nucleotide sequence of SEQ ID No. 5 from nucleotide 1 to nucleotide 166 or SEQ ID No. 24 from nucleotide 1 to nucleotide 1113, or the complement of the nucleotide sequence of SEQ ID 6 from nucleotide 359 to nucleotide 691, or the complement of the nucleotide sequence of SEQ ID No. 25 from nucleotide 359 to nucleotide 1449, combined with primers comprising, consisting, or consisting essentially of a nucleotide sequence of 17 to about 200 consecutive nucleotides selected from the nucleotide sequence of SEQ ID No. 11 from nucleotide 1 to nucleotide 7459 or SEQ ID No. 23 from nucleotide position 1114 to nucleotide position 8572, such as a nucleotide sequence of 17 to about 200 consecutive nucleotides selected from the nucleotide sequence of SEQ ID No. 5 from nucleotide 167 to nucleotide 353 or the nucleotide sequence of SEQ ID No. 6 from nucleotide 1 to nucleotide 358, or the complement thereof. Primers may also comprise these nucleotide sequences located at their extreme 3' end, and further comprise unrelated sequences or sequences derived from the mentioned nucleotide sequences, but comprising mismatches. In one embodiment, the primers as used herein, can also be identical to the target DNA or the complement thereof, wherein said target DNA is a hybrid containing nucleotide sequences from different origins, that do not occur in such combination in nature.

The invention further relates to kits for identifying elite event EE-GM5 in biological samples, said kits comprising at least one primer pair or probe which specifically recognizes the 5' or 3' T-DNA flanking region and the inserted T-DNA comprising a herbicide tolerance and a nematode resistance gene contiguous therewith in EE-GM5.

The kit of the invention may comprise, in addition to a primer which specifically recognizes the 5' or 3' T-DNA flanking region of EE-GM5, a second primer which specifically recognizes a sequence within the inserted T-DNA comprising an HPPD inhibitor herbicide tolerance and a nematode resistance gene of EE-GM5, for use in a PCR identification protocol. The kits of the invention may comprise at least two specific primers, one of which recognizes a sequence within the 5' T-DNA flanking region of EE-GM5 or a sequence within the 3' T-DNA flanking region of EE-GM5, and the other which recognizes a sequence within the inserted T-DNA comprising an HPPD inhibitor herbicide tolerance and a nematode resistance gene. The primer recognizing the 5' T-DNA flanking region may comprise the nucleotide sequence of SEQ ID No. 19 and the primer recognizing the inserted T-DNA contiguous with said 5' T-DNA flanking region may comprise the nucleotide sequence of SEQ ID No. 18, or the primer recognizing the 3' T-DNA flanking region may comprise the nucleotide sequence of SEQ ID No. 13 and the primer recognizing the inserted T-DNA contiguous with said 3' flanking region may comprise the nucleotide sequence of SEQ ID No. 12, or any other primer or primer combination as described herein or obtainable from the description or the seed deposit. The kit may further comprise a probe recognizing a sequence located between the primer recognizing the 5' T-DNA flanking region and the primer recognizing the sequence within the inserted T-DNA, or recognizing a sequence between the primer recognizing the 3' T-DNA flanking region and the primer recognizing the sequence within the inserted T-DNA, such as a probe comprising the sequence of SEQ ID No. 14 or a probe comprising the sequence of SEQ ID No. 20.

The invention further relates to a kit for identifying elite event EE-GM5 in biological samples, said kit comprising the PCR primers comprising or consisting (essentially) of the nucleotide sequence of SEQ ID No. 12 and SEQ ID No. 13, or of the nucleotide sequence of SEQ ID No. 18 and SEQ ID No. 19 for use in the EE-GM5 PCR protocol described herein. Said kit comprising the primers comprising or consisting (essentially) of the nucleotide sequence of SEQ ID No. 12 and SEQ ID No. 13 may further comprise a probe comprising or consisting (essentially) of the nucleotide sequence of SEQ ID No. 14, and said kit comprising the primers comprising or consisting (essentially) of the nucleotide sequence of SEQ ID No. 18 and SEQ ID No. 19 may further comprise a probe comprising or consisting (essentially) of the nucleotide sequence of SEQ ID No. 20. Said kit can further comprise buffer and reagents such as anyone or each of the following compounds: dNTPs, (Taq) DNA polymerase, MgCl2, stabilizers, and optionally a dye.

The invention also relates to a kit for identifying elite event EE-GM5 in biological samples, which kit comprises a specific probe comprising or consisting (essentially) of a sequence which corresponds (or is complementary) to a sequence having 80% to 100% sequence identity with a specific region of EE-GM5, wherein such specific region comprises part of the 5' or 3' T-DNA flanking region of EE-GM5 and part of the inserted T-DNA contiguous therewith. In one embodiment, the sequence of the probe corresponds to a specific region comprising part of the 5' or 3' T-DNA flanking region of EE-GM5 and part of the inserted T-DNA contiguous therewith.

Most preferably the specific probe comprises or consists (essentially) of (or is complementary to) a sequence having 80% to 100% sequence identity to the sequence of any one of SEQ ID No. 1, 3 or 5, or a sequence having 80% to 100% sequence identity to the sequence of any one of SEQ ID No. 2, 4 or 6, or the specific probe comprises or consists (essentially) of (or is complementary to) a sequence having 80% to 100% sequence identity to a part of at least 50 contiguous nucleotides of the sequence of SEQ ID No. 5, or a sequence having 80% to 100% sequence identity to a part of at least 50 contiguous nucleotides of the sequence of SEQ ID No. 6, wherein each of said part of SEQ ID No. 5 or 6 comprises sequences of inserted T-DNA and T-DNA flanking sequences of approximately equal length.

According to another aspect of the invention, DNA molecules are disclosed comprising sufficient length of polynucleotides of both the T-DNA flanking sequences and the inserted T-DNA of EE-GM5, so as to be useful as primer or probe for the detection of EE-GM5, or to characterize plants comprising event EE-GM5. Such sequences may comprise any one of at least 9, at least 10, at least 15, at least 20, or at least 30 nucleotides, or may comprise any one of 9, 10, 15, 20 or 30 nucleotides of the T-DNA flanking sequence and a similar number of nucleotides of the inserted T-DNA of EE-GM5, at each side of the junction site respectively, and this at either or both of the 5' and 3' junction site of the EE-GM5 event. Most preferably, such DNA molecules comprise the sequence of any one of SEQ ID No. 1, 3, or 5 or the sequence of any one of SEQ ID No. 2, 4, or 6. In one embodiment, such DNA molecules comprise the sequence of SEQ ID No. 23, 24 or 25. In one aspect of the invention, soybean plants and seeds are provided comprising such specific DNA molecules.

The methods and kits encompassed by the present invention can be used for different purposes such as, but not limited to the following: to identify the presence or determine the (lower) threshold of EE-GM5 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e., percentage pure material) of plant material comprising EE-GM5.

The invention further relates to the 5' and/or 3' T-DNA flanking regions of EE-GM5 as well as to the specific primers and probes developed from the 5' and/or 3' T-DNA flanking sequences of EE-GM5.

The invention also relates to genomic DNA obtained from plants comprising elite event EE-GM5, particularly genomic DNA comprising EE-GM5 event-specific sequences, such as one or both of the EE-GM5 junction sequences (containing a part of T-DNA flanking DNA and inserted T-DNA contiguous therewith, characteristic for EE-GM5), e.g., any one of the sequences of SEQ ID No. 1, 3, 5, or 24 and/or any one of the sequences of SEQ ID No. 2, 4, 6, or 25. Such genomic DNA may be used as reference control material in the identification assays herein described.

Also provided herein is a transgenic nematode resistant and herbicide tolerant soybean plant, or cells, parts, seeds or progeny thereof, each comprising at least one elite event, said elite event comprises an inserted T-DNA comprising:
i) a first chimeric gene which comprises a cry14Ab-1.b gene derived from *Bacillus thuringiensis* encoding a Cry14Ab-1 protein under the control of a plant-expressible promoter, such as a chimeric gene comprising a plant-expressible promoter and the coding sequence of SEQ ID No. 7 and
ii) a second chimeric gene which comprises a modified hppdPf-4 Pa gene from *Pseudomonas* encoding a more tolerant HPPD enzyme under the control of a plant-expressible promoter, such as a chimeric gene comprising a plant-expressible promoter and the coding sequence of SEQ ID No. 9.

In one embodiment, said elite event comprises nucleotides 1 to 166 of SEQ ID No. 5 or 1 to 1113 of SEQ ID No. 24 immediately upstream of and contiguous with said inserted T-DNA and nucleotides 359 to 691 of SEQ ID No. 6 or nucleotides 359 to 1449 of SEQ ID No. 25 immediately downstream of and contiguous with said inserted T-DNA.

In a further embodiment, said elite event is obtainable by breeding with a soybean plant grown from reference seed comprising said event having been deposited at the ATCC under deposit number PTA-123625.

In another embodiment, the genomic DNA of said soybean plant, or cells, parts, seeds or progeny thereof when analyzed using PCR with two primers comprising the nucleotide sequence of SEQ ID No. 12 and SEQ ID No. 13 respectively, yields a DNA fragment of 85 bp, or when analyzed using PCR with two primers comprising the nucleotide sequence of SEQ ID No. 18 and SEQ ID No. 19 respectively, yields a DNA fragment of 84 bp.

Also provided herein is a method for identifying a transgenic soybean plant, or cells, parts, seed or progeny thereof with nematode resistance, such as SCN and/or *Pratylenchus* and/or root-knot and/or reniform nematode resistance, and tolerance to an HPPD inhibitor herbicide, such as isoxaflutole, topramezone or mesotrione, in biological samples, said method comprising amplifying a DNA fragment of between 50 and 150 bp from a nucleic acid present in biological samples using a polymerase chain reaction with at least two primers, one of said primers recognizing the 5' T-DNA flanking region of the elite event EE-GM5, said 5' T-DNA flanking region comprising the nucleotide sequence of SEQ ID No. 5 from nucleotide 1 to nucleotide 166 or of SEQ ID No. 24 from nucleotide 1 to nucleotide 1113, or recognizing the 3' T-DNA flanking region of said elite event, said 3' T-DNA flanking region comprising the nucleotide sequence of the complement of SEQ ID No. 6 from nucleotide 359 to nucleotide 691, or the nucleotide sequence of the complement of SEQ ID No. 25 from nucleotide 359 to nucleotide 1449, the other primer of said primers recognizing a sequence within the inserted T-DNA comprising the nucleotide sequence of the complement of SEQ ID No. 5 from nucleotide 167 to nucleotide 353 or the nucleotide sequence of SEQ ID No. 6 from nucleotide 1 to nucleotide 358, or wherein said inserted T-DNA comprises the nucleotide sequence of SEQ ID No. 11 from nucleotide position 1 to nucleotide position 7459, or the complement thereof.

Also provided herein is a kit for identifying a transgenic soybean plant, or cells, parts, seed or progeny thereof with nematode resistance and tolerance to an HPPD inhibitor herbicide, in biological samples, said kit comprising one primer recognizing the 5' T-DNA flanking region of elite event EE-GM5, said 5' T-DNA flanking region comprising the nucleotide sequence of SEQ ID No. 5 from nucleotide 1 to nucleotide 166, or the nucleotide sequence of SEQ ID No. 24 from nucleotide 1 to nucleotide 1113, or one primer recognizing the 3' T-DNA flanking region of said elite event, said 3' T-DNA flanking region comprising the nucleotide sequence of the complement of SEQ ID No. 6 from nucleotide 359 to nucleotide 691, or the nucleotide sequence of the complement of SEQ ID No. 25 from nucleotide 359 to nucleotide 1449, and one primer recognizing a sequence within the inserted T-DNA, said inserted T-DNA comprising the nucleotide sequence of the complement of SEQ ID No. 5 from nucleotide 167 to nucleotide 353 or the nucleotide sequence of SEQ ID No. 6 from nucleotide 1 to nucleotide 358, or said inserted T-DNA comprising the nucleotide sequence of SEQ ID No. 11 from nucleotide position 1 to nucleotide position 7459, or the complement thereof.

In one embodiment of the invention, the inserted T-DNA of elite event EE-GM5, as used herein, comprises the nucleotide sequence of SEQ ID No. 5 from nucleotide 167 to nucleotide 353 or its complement, and the nucleotide sequence of SEQ ID No. 6 from nucleotide 359 to nucleotide 691 or its complement, or comprises a sequence with at least 95, 98, 99, 99.5, or 99.9% sequence identity to the nucleotide sequence of SEQ ID No. 11 from nucleotide position 7 to nucleotide position 7459, or its complement.

Also provided herein is a soybean plant, plant cell, tissue, or seed, comprising in their genome a nucleic acid molecule comprising the nucleotide sequence of any one of SEQ ID No. 1, 3, 5, or 24 or a nucleotide sequence of 80 to 100% sequence identity thereto and/or SEQ ID No. 2, 4, 6, or 25, or a nucleotide sequence of 80 to 100% sequence identity thereto, and a nucleotide sequence with at least 80, 85, 90, 95, 97, 98, 99, 99.5 or at least 99.9% sequence identity to the nucleotide sequence of SEQ ID No. 11 from nucleotide position 188 to nucleotide position 7101 or the complement thereof.

One embodiment of this invention provides a soybean plant, plant cell, tissue, or seed, comprising in their genome a nucleic acid molecule hybridizing under standard stringency conditions to the nucleotide sequence of any one of SEQ ID No. 1, 3, or 5 or the complement thereof, or hybridizing to the nucleotide sequence of any one of SEQ ID No. 2, 4 or 6 or the complement thereof.

Also provided herein is an isolated nucleic acid molecule comprising a nucleotide sequence with at least 90%, at least 95%, at least 98%, or at least 99% sequence identity to the nucleotide sequence of any one of SEQ ID No. 1, 3, 5, or 24, or the complement thereof, or with at least 90%, at least 95%, at least 98%, or at least 99% sequence identity to the nucleotide sequence of any one of SEQ ID No. 2, 4, 6, or 25, or the complement thereof, or an isolated nucleic acid molecule comprising a nucleotide sequence hybridizing under standard stringency conditions to the nucleotide sequence of any one of SEQ ID No. 1, 3, 5, or 24, or the complement thereof, or to the nucleotide sequence of any one of SEQ ID No. 2, 4, 6, or 25, or the complement thereof.

Also provided herein is an isolated nucleic acid molecule comprising a nucleotide sequence with at least 90%, at least 95%, at least 98%, or at least 99% sequence identity to the nucleotide sequence of SEQ ID No. 7 or the complement thereof, or an isolated nucleic acid molecule comprising a nucleotide sequence hybridizing under standard stringency conditions to the nucleotide sequence of SEQ ID No. 7 or the complement thereof, wherein such nucleic acid molecule encodes a nematicidal toxin active to cyst nematodes and/or lesion nematodes and/or root-knot nematodes and/or reniform nematode, such as *Heterodera glycines* and/or *Pratylenchus brachyurus* and/or *Meloidogyne incognita* and/or *Rotylenchulus reniformis*. In one embodiment, such nucleic acid molecule is operably-linked to a nucleic acid molecule comprising a (heterologous) plant-expressible promoter so as to form a chimeric gene. Also provided herein is the use of said nucleic acid molecule in transformed plants or seeds to control plant-pathogenic nematodes. Further provided herein is a method to control root-knot nematodes such as *Meloidogyne incognita, Meloidogyne arenaria, Meloidogyne hapla*, or *Meloidogyne javanica*, particularly *Meloidogyne incognita*, comprising using a Cry14Ab protein or a DNA encoding a Cry14Ab protein or a plant or seed containing said DNA under the control of a plant-expressible promoter, wherein said Cry14Ab protein is the protein comprising the amino acid sequence of SEQ ID No. 8 or a protein with at least 96% or at least 98 or at least 99% sequence identity thereto, or a protein comprising the amino acid sequence of SEQ ID No. 8 from amino acid position 1 to amino acid position 706, or a protein with at least 96% or at least 98 or at least 99% sequence identity thereto. Further provided herein is a method to control reniform nematodes (*Rotylenchulus reniformis*), comprising using a Cry14Ab protein or a DNA encoding a Cry14Ab protein, or a plant or seed containing said DNA, under the control of a plant-expressible promoter, wherein said Cry14Ab protein is the protein comprising the amino acid sequence of SEQ ID No. 8 or a protein with at least 96% or at least 98% or at least 99% sequence identity thereto, or a protein comprising the amino acid sequence of SEQ ID No. 8 from amino acid position 1 to amino acid position 706, or a protein with at least 96% or at least 98% or at least 99% sequence identity thereto.

Also provided herein is a nucleic acid molecule comprising the nucleotide sequence of SEQ ID No. 11 from nucleotide position 131 to nucleotide position 7941, or a nucleotide sequence having at least 95%, at least 96%, at least 97%, at least 98%, or at least 99% sequence identity thereto, wherein said nucleic acid molecule encodes a nematicidal Cry14Ab protein and an HPPD protein tolerant to HPPD inhibitors. In one embodiment, that nucleic acid molecule encodes the protein of SEQ ID No. 8 or a protein at least 99% identical thereto and the protein of SEQ ID No. 10, or a protein at least 99% identical thereto.

Also provided herein is a soybean plant cell comprising in its genome elite event EE-GM5 which is a foreign DNA or an inserted T-DNA at a defined locus, wherein the elite event EE-GM5 is as contained in reference seed deposited at the ATCC under deposit number PTA-123625, wherein said inserted T-DNA comprises a chimeric Cry14Ab-1-encoding gene and a chimeric HPPD-4-encoding gene, and wherein said elite event is characterized by the 5' junction sequence of SEQ ID No. 1 or 3 and by the 3' junction sequence of SEQ ID No. 2 or 4; or such cell which is a seed cell, or such cell, wherein the genomic DNA of said cell, when analyzed using PCR with two primers comprising the nucleotide sequence of SEQ ID 12 and SEQ ID 13 respectively, yields a DNA fragment of 85 bp.

The invention provides a nucleic acid molecule comprising the nucleotide sequence of elite event EE-GM5 as contained in reference seed deposited at the ATCC under deposit number PTA-123625, wherein said elite event comprises a chimeric Cry14Ab-1-encoding gene and an HPPD-4-encoding gene, and comprises the sequence of SEQ ID No. 1 or 3 and the sequence of SEQ ID No. 2 or 4.

The invention also provides a nucleic acid molecule comprising in order the following nucleotide sequences: a) the nucleotide sequence of SEQ ID NO. 5 from nucleotide 1 to 166 or a sequence at least 99% identical thereto, b) the nucleotide sequence of SEQ ID No. 11 from nucleotide 188 to nucleotide 7101 or a sequence at least 99% identical thereto, and c) the nucleotide sequence of SEQ ID NO. 6 from nucleotide 359 to nucleotide 691 or a sequence at least 99% identical thereto, such as such nucleic acid molecule comprising a sequence b) that is at least 99.5% or at least 99.9% identical to the nucleotide sequence of SEQ ID No. 11 from nucleotide 188 to nucleotide 7101.

The invention also provides a nucleic acid molecule comprising in order the following nucleotide sequences: a) the nucleotide sequence of SEQ ID NO. 24 from nucleotide 1 to 1113 or a sequence at least 99% identical thereto, b) the nucleotide sequence of SEQ ID No. 23 from nucleotide 1114 to nucleotide 8572 or a sequence at least 99% identical thereto, and c) the nucleotide sequence of SEQ ID NO. 25 from nucleotide 359 to nucleotide 1449 or a sequence at least 99% identical thereto, such as such nucleic acid molecule comprising a sequence b) that is at least 99.5% or at least 99.9% identical to the nucleotide sequence of SEQ ID No. 23. In accordance with the invention is also provided a method for producing a soybean product, comprising obtaining soybean seed comprising elite event EE-GM5 as described above, and producing the soybean product therefrom. In one embodiment, the soybean product in such a method is or comprises soybean meal, ground seeds, flour, or flakes, or soybean oil, soybean protein, lecithin, soybean milk, tofu, margarine, biodiesel, biocomposite, adhesive, solvent, lubricant, cleaner, foam, paint, ink, candle, or a soybean-oil or soybean protein-containing food or feed product. In another embodiment, such soybean product comprises a nucleic acid specific for elite event EE-GM5. In one embodiment, said nucleic acid specific for elite event EE-GM5 comprises the sequence of SEQ ID No. 1 or 3, or the sequence of SEQ ID No. 2 or 4.

Also provided herein is a soybean product produced from the seed comprising elite event EE-GM5 as described above, wherein said soybean product is or comprises soybean meal, ground seeds, flour, or flakes, and comprises nucleic acids specific for elite event EE-GM5, wherein said nucleic acids are detectable using the methods as described herein. In one embodiment, said nucleic acid specific for elite event EE-GM5 comprises the sequence of SEQ ID No. 1 or 3, or the sequence of SEQ ID No. 2 or 4. In another embodiment, said nucleic acid specific for elite event EE-GM5 comprises the sequence of SEQ ID No. 5 or 24, or the sequence of SEQ ID No. 6 or 25. In one embodiment, said nucleic acid specific for elite event EE-GM5 comprises the sequence of SEQ ID No. 5 or 24, and the sequence of SEQ ID No. 6 or 25.

Also provided herein is the use of soybean seed comprising elite event EE-GM5 to obtain a soybean product, wherein said elite event comprises the sequence of any one of SEQ ID NO. 1, 3, 5 or 24 and/or the sequence of any one of SEQ ID No. 2, 4, 6, or 25. In one embodiment, in such use, the soybean product is any one of soybean meal, ground soybean seeds, soybean flour or soybean flakes.

Further, provided herein is a method for producing a soybean plant or seed comprising elite event EE-GM5 combined with another SCN resistance locus/gene, such as by combining elite event EE-GM5 with another SCN resistance locus/gene occurring in the same soybean plant/seed, and planting seed comprising EE-GM5 and said other SCN resistance locus/gene. In one embodiment, the plants, cells or seeds of the invention contain one or more other SCN resistance loci/genes that occur in soybean, to get a combination of different SCN resistance sources in the soybean plants, cells or seeds of the invention. Several soybean SCN resistance loci or genes are known and one or more of those can be combined with EE-GM5 in the same plant, cell or seed, such as any one of the SCN resistance genes/loci from the resistance sources PI 88788, PI 548402 (Peking), PI 437654 (Hartwig or CystX®), or any combination thereof, or one or more of the native SCN resistance loci/genes rhg1, rhg1-b, rhg2, rhg3, Rhg4, Rhg5, qSCN11, cqSCN-003, cqSCN-005, cqSCN-006, cqSCN-007, or any of the SCN resistance loci identified on any one of soybean chromosomes 1, 3, 4, 5, 6, 7, 8, 9, 10, 11, 12, 13, 14, 15, 16, 17, 18, 19, or 20 of any combination thereof (Kim et al. 2016, Theor. Appl. Genet. 129(12):2295-2311; Kim and Diers 2013, Crop Science 53:775-785; Kazi et al. 2010, Theor. Appl. Gen. 120(3):633-644; Glover et al. 2004, Crop Science 44(3):936-941; www.soybase.org; Concibido et al. 2004, Crop Science 44:1121-1131; Webb et al. 1995, Theor. Appl. Genet. 91:574-581). Also, in one embodiment the plants or seeds of the invention contain EE-GM5 when combined with one or more SCN resistance loci in soybean obtained from any one of SCN resistance sources PI 548316, PI 567305, PI 437654, PI 90763, PI 404198B, PI 88788, PI 468916, PI 567516C, PI 209332, PI 438489B, PI 89772, Peking, PI 548402, PI 404198A, PI 561389B, PI 629013, PI 507471, PI 633736, PI 507354, PI 404166, PI 437655, PI 467312, PI 567328, PI 22897, or PI 494182. Table 3 enclosed hereto provides a comprehensive list of soybean accessions reported as SCN resistant, of which the SCN resistance genes/loci (one or several) can be combined with EE-GM5 of the invention in the same soybean plant, cell or seed.

TABLE 3

| | | | | | | |
|---|---|---|---|---|---|---|
| FC 21340 | PI 404192C | PI 438498 | PI 507451 | PI 548974 | PI 567771C | PI 68465 |
| FC 31685 | PI 404198A | PI 438503A | PI 507470 | PI 548975 | PI 567773 | PI 68622 |
| PI 101404A | PI 404198B | PI 458506 | PI 507471 | PI 548981 | PI 603587A | PI 70027 |
| PI 153229 | PI 407022 | PI 458510 | PI 507475 | PI 548982 | PI 605743B | PI 70213 |
| PI 153297 | PI 407221 | PI 458519A | PI 507476 | PI 548988 | PI 606416A | PI 70229 |
| PI 153303 | PI 407729 | PI 458520 | PI 507686C | PI 549031 | PI 606420 | PI 70251 |
| PI 157430 | PI 416762 | PI 461509 | PI 509095 | PI 553040 | PI 606424 | PI 70519 |
| PI 157444 | PI 417091 | PI 464888A | PI 509100 | PI 553047 | PI 606430 | PI 71161 |
| PI 16790 | PI 423927 | PI 464910 | PI 511813 | PI 559370 | PI 606435 | PI 79620 |

TABLE 3-continued

| | | | | | | |
|---|---|---|---|---|---|---|
| PI 17852-B | PI 424387 | PI 464912 | PI 518772 | PI 561389B | PI 606436 | PI 79712 |
| PI 181558 | PI 424595 | PI 464925B | PI 522186 | PI 56563 | PI 606437 | PI 80834-2 |
| PI 200495 | PI 437654 | PI 467312 | PI 522236 | PI 567305 | PI 606439 | PI 82308 |
| PI 209332 | PI 437655 | PI 467327 | PI 533605 | PI 567325B | PI 606441 | PI 84664 |
| PI 22897 | PI 437679 | PI 467332 | PI 540556 | PI 567328 | PI 606443 | PI 84751 |
| PI 232993 | PI 437690 | PI 468903 | PI 543855 | PI 567333A | PI 612610 | PI 84807 |
| PI 303652 | PI 437725 | PI 468915 | PI 54620-2 | PI 567354 | PI 612611 | PI 84896 |
| PI 339868B | PI 437770 | PI 468916 | PI 548316 | PI 567360 | PI 612612A | PI 87631-1 |
| PI 339871A | PI 437793 | PI 468916 | PI 548349 | PI 567387 | PI 612614 | PI 88788 |
| PI 346298 | PI 437844A | PI 494182 | PI 548376 | PI 567488B | PI 612615 | PI 89008 |
| PI 347544A | PI 437904 | PI 495017C | PI 548402 | PI 567491A | PI 612616 | PI 89772 |
| PI 371610 | PI 438342 | PI 506862 | PI 548402S | PI 567516C | PI 612617A | PI 89783 |
| PI 378690 | PI 438489B | PI 507354 | PI 548456 | PI 567676A | PI 62202 | PI 90763 |
| PI 398682 | PI 438491 | PI 507422 | PI 548655 | PI 567726 | PI 629013 | PI 91102 |
| PI 399061 | PI 438496B | PI 507423 | PI 548665 | PI 567737 | PI 633736 | PI 92576 |
| PI 404166 | PI 438497 | PI 507443 | PI 548970 | PI 567741 | PI 63468 | PI 92595 |
| | | | | | | PI 96549 |

Also provided herein is a method for protecting emerging soybean plants from competition by weeds, comprising treating a field in which seeds containing elite event EE-GM5 as described above were sown, with an HPPD inhibitor herbicide, wherein the plants are tolerant to the HPPD inhibitor herbicide. In one embodiment, in such method the HPPD inhibitor herbicide is isoxaflutole, topramezone or mesotrione.

Also provided herein is method for protecting emerging soybean plants from competition by weeds, comprising treating a field to be planted with soybean plants comprising elite event EE-GM5 as described above with an HPPD inhibitor herbicide, before the soybean plants are planted or the seeds are sown, followed by planting or sowing of said soybean plants or seeds in said pre-treated field, wherein the plants are tolerant to the HPPD inhibitor herbicide.

Also provided herein is a method for controlling weeds in a field of soybean plants comprising elite event EE-GM5 as described above, comprising treating said field with an effective amount of an HPPD inhibitor herbicide, wherein the plants are tolerant to such herbicide.

Even further provided herein is the use of a transgenic soybean plant, seed or progeny thereof, to control weeds in a soybean field, wherein each of said plant, seed or progeny comprises elite event EE-GM5 in its genome, wherein EE-GM5 which is a T-DNA at a defined locus, as contained in reference seed deposited at ATCC under deposit number PTA-123625, wherein said T-DNA comprises a chimeric Cry14Ab-1-encoding gene and a chimeric HPPD-4-encoding gene, and wherein said elite event is characterized by the 5' junction sequence of SEQ ID No. 1 or 3 and by the 3' junction sequence of SEQ ID No. 2 or 4. In one embodiment, in such use the transgenic soybean plant, seed or progeny thereof is resistant to nematodes and/or tolerant to an HPPD inhibitor herbicide. In one embodiment, said T-DNA comprises a chimeric Cry14Ab-1-encoding gene and a chimeric HPPD-4-encoding gene, and said elite event is characterized by the 5' junction sequence of SEQ ID No. 5 or 24 and by the 3' junction sequence of SEQ ID No. 6 or 25.

Also provided herein is the use of a soybean plant or seed comprising elite event EE-GM5 in its genome to grow a nematode-resistant and/or herbicide-tolerant plant, wherein said elite event EE-GM5 is an inserted T-DNA at a defined locus, as contained in reference seed deposited at ATCC under deposit number PTA-123625, wherein said inserted T-DNA comprises a chimeric Cry14Ab-1-encoding gene and a chimeric HPPD-4-encoding gene, and wherein said elite event is characterized by the 5' junction sequence of SEQ ID No. 1 or 3 and by the 3' junction sequence of SEQ ID No. 2 or 4. In one embodiment, in such use the soybean plant or seed is resistant to SCN nematodes and/or tolerant to an HPPD inhibitor herbicide. In one embodiment, said T-DNA comprises a chimeric Cry14Ab-1-encoding gene and a chimeric HPPD-4-encoding gene, and said elite event is characterized by the 5' junction sequence of SEQ ID No. 5 or 24 and by the 3' junction sequence of SEQ ID No. 6 or 25.

Also provided herein is the use of a soybean seed comprising elite event EE-GM5 to obtain a soybean product, wherein EE-GM5 is as described above.

Also provided herein is a method for producing a soybean plant or seed comprising elite event EE-GM5, comprising crossing a plant comprising EE-GM5 with another soybean plant, and planting seed comprising EE-GM5 obtained from said cross. In one embodiment, such method includes the step of application of an HPPD inhibitor herbicide on said seed or plant.

In accordance with this invention, also provided is the use of a soybean seed comprising elite event EE-GM5 as described above, and an HPPD inhibitor herbicide, to control weeds in a soybean field, and the use of a soybean seed comprising elite event EE-GM5 in a method of growing soybeans tolerant to HPPD inhibitor herbicides, wherein said seed is as described above.

Further provided herein is the use of elite event EE-GM5 as described above to confer resistance to nematodes and/or tolerance to an HPPD inhibitor herbicide to a soybean plant or seed, or the use of a soybean plant or seed comprising elite event EE-GM5, in combination with an HPPD inhibitor herbicide, for growing soybeans.

Also provided herein is a primer pair specific for EE-GM5, as well as kits or methods using such primer pair, wherein at least one primer of said pair is labeled (such as with a detectable or screenable moiety), or wherein the 5' end of at least one of said primers comprises one or more mismatches or a nucleotide sequence unrelated to the 5' or 3' flanking sequences of EE-GM5 or unrelated to the T-DNA sequence of EE-GM5; or wherein at least one of said primers comprises a nucleotide sequence at their 3' end spanning the joining region between the T-DNA flanking sequences and the T-DNA sequences, said joining region being at nucleotides 166-167 in SEQ ID No. 5, nucleotides 1113-1114 in SEQ ID No. 24, or at nucleotides 358-359 in SEQ ID No. 6 or 25, provided that the 17 consecutive nucleotides at the 3' end are not derived exclusively from either the T-DNA or T-DNA flanking sequences in SEQ ID Nos. 5 or 24, or 6 or 25; or wherein at least one of said primers comprises a sequence which is between 80 and 100% identical to a sequence within the 5' or 3' flanking region of EE-GM5 or within the inserted T-DNA of EE-GM5, respectively, and said primer sequence comprises at least one mismatch with said 5' or 3' flanking region or said T-DNA, provided the at least one mismatch still allows specific identification of the elite event EE-GM5 with these primers under optimized detection conditions (e.g., optimized PCR conditions); or wherein the nucleotide sequence of at least one of said primers comprises the nucleotide sequence of a nucleic acid fused to a nucleic acid from another origin, or its complement.

Other embodiments according to the invention are summarized in the following paragraphs:

1. A method for identifying elite event EE-GM5 in biological samples, which method comprises detection of an EE-GM5 specific region with a specific primer pair or probe which specifically recognize(s) (at least a part of) the 5' or 3' T-DNA flanking region and (at least a part of) the inserted T-DNA contiguous therewith in EE-GM5.
2. The method of paragraph 1, said method comprising amplifying a DNA fragment of between 50 and 1000 bp from a nucleic acid present in said biological samples using a polymerase chain reaction with at least two primers, one of said primers recognizing the 5' T-DNA flanking region in EE-GM5, said 5' T-DNA flanking region comprising the nucleotide sequence of SEQ ID No. 5 from nucleotide 1 to nucleotide 166 or of SEQ ID No. 24 from nucleotide 1 to nucleotide 1113 or recognizing the 3' T-DNA flanking region in EE-GM5, said 3' T-DNA flanking region comprising the nucleotide sequence of the complement of SEQ ID No. 6 from nucleotide 359 to nucleotide 691 or the nucleotide sequence of the complement of SEQ ID No. 25 from nucleotide 359 to nucleotide 1449, the other primer of said primers recognizing a sequence within the inserted T-DNA comprising the nucleotide sequence of SEQ ID No. 5 from nucleotide 167 to nucleotide 353 or the complement thereof, or the nucleotide sequence of SEQ ID No. 6 from nucleotide 1 to nucleotide 358 or the complement thereof, or the nucleotide sequence of SEQ ID No. 23 from nucleotide 1114 to nucleotide 8572, or the complement thereof.
3. The method of paragraph 2, wherein said primer recognizing the 5' T-DNA flanking region comprises a nucleotide sequence of 17 to 200 consecutive nucleotides selected from the nucleotide sequence of SEQ ID No. 5 from nucleotide 1 to nucleotide 166 or of SEQ ID No. 24 from nucleotide 1 to nucleotide 1113, or said primer recognizing the 3' T-DNA flanking region of EE-GM5 comprises a nucleotide sequence of 17 to 200 consecutive nucleotides selected from the nucleotide sequence of the complement of SEQ ID No. 6 from nucleotide 359 to nucleotide 691 or the nucleotide sequence of the complement of SEQ ID No. 25 from nucleotide 359 to nucleotide 1449, and said primer recognizing a sequence within the inserted T-DNA comprises 17 to 200 consecutive nucleotides selected from the nucleotide sequence of SEQ ID No. 5 from nucleotide 167 to nucleotide 353 or the complement thereof, or the nucleotide sequence of SEQ ID No. 6 from nucleotide 1 to nucleotide 358 or the complement thereof, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof.
4. The method of paragraph 2, wherein said primer recognizing the 5' T-DNA flanking region comprises at its extreme 3' end a nucleotide sequence of at least 17 consecutive nucleotides selected from the nucleotide sequence of SEQ ID No. 5 from nucleotide 1 to nucleotide 166 or of SEQ ID No. 24 from nucleotide 1 to nucleotide 1113, or said primer recognizing the 3' T-DNA flanking region of EE-GM5 comprises at its extreme 3' end a nucleotide sequence of at least 17 consecutive nucleotides selected from the nucleotide sequence of the complement of SEQ ID No. 6 from nucleotide 359 to nucleotide 691 or the nucleotide sequence of the complement of SEQ ID No. 25 from nucleotide 359 to nucleotide 1449, and said primer recognizing a sequence within the inserted T-DNA comprises at its extreme 3' end at least 17 consecutive nucleotides selected from the complement of the nucleotide sequence of SEQ ID No. 5 from nucleotide 167 to nucleotide 353, or the nucleotide sequence of SEQ ID No. 6 from nucleotide 1 to nucleotide 358, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof.
5. The method of paragraph 4, wherein said primers comprise the sequence of SEQ ID No. 12 and SEQ ID No. 13, respectively, or the sequence of SEQ ID No. 18 and SEQ ID No. 19, respectively.
6. The method of paragraph 5, which method comprises amplifying an EE-GM5-specific fragment of 85 or 84 bp using PCR.
7. The method of any one of paragraphs 2 to 6, further comprising the step of hybridizing a probe specific for the DNA fragment amplified with said at least two primers.
8. The method of paragraph 7, wherein said probe recognizes part of said 5' T-DNA flanking region and part of the inserted T-DNA contiguous therewith, or wherein said probe recognizes part of said 3' T-DNA flanking region and part of the inserted T-DNA contiguous therewith, or recognizes part of said 5' T-DNA flanking region and part of the inserted T-DNA contiguous therewith, such as wherein said probe comprises the nucleotide sequence of SEQ ID No. 1 or 3 or SEQ ID No 2 or 4.
9. The method of paragraph 8, wherein said primers comprise the sequence of SEQ ID No. 12 and SEQ ID No. 13, respectively, and wherein said probe comprises the sequence of SEQ ID No. 14, or wherein said primers comprise the sequence of SEQ ID No. 18 and SEQ ID No. 19, respectively, and wherein said probe comprises the sequence of SEQ ID No. 20.
10. A kit comprising one primer recognizing the 5' T-DNA flanking region of EE-GM5, said 5' T-DNA flanking region comprising the nucleotide sequence of SEQ ID No. 5 from nucleotide 1 to nucleotide 166 or of SEQ ID No. 24 from nucleotide 1 to nucleotide 1113, or one primer recognizing the 3' T-DNA flanking region of EE-GM5, said 3' T-DNA flanking region comprising the nucleotide sequence of the complement of SEQ ID No. 6 from nucleotide 359 to nucleotide 691 or the nucleotide sequence of the complement of SEQ ID No. 25 from nucleotide 359 to nucleotide 1449, and one primer recognizing a sequence within the inserted T-DNA, said inserted T-DNA comprising the complement of the nucleotide sequence of SEQ ID No. 5 from nucleotide 167 to nucleotide 353 or the nucleotide sequence of SEQ ID No. 6 from nucleotide 1 to nucleotide 358, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or its complement thereof.

11. The kit of paragraph 10, wherein said primer recognizing the 5' T-DNA flanking region comprises a nucleotide sequence of 17 to 200 consecutive nucleotides selected from the nucleotide sequence of SEQ ID No. 5 from nucleotide 1 to nucleotide 166 or of SEQ ID No. 24 from nucleotide 1 to nucleotide 1113, or said primer recognizing the 3' T-DNA flanking region of EE-GM5 comprises a nucleotide sequence of 17 to 200 consecutive nucleotides selected from the nucleotide sequence of the complement of SEQ ID No. 6 from nucleotide 359 to nucleotide 691 or the nucleotide sequence of the complement of SEQ ID No. 25 from nucleotide 359 to nucleotide 1449, and said primer recognizing a sequence within the inserted T-DNA comprises 17 to 200 consecutive nucleotides selected from the complement of the nucleotide sequence of SEQ ID No. 5 from nucleotide 167 to nucleotide 353 or the nucleotide sequence of SEQ ID No. 6 from nucleotide 1 to nucleotide 358, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof.

12. The kit of paragraph 10, wherein said primer recognizing the 5' T-DNA flanking region comprises at its extreme 3' end a nucleotide sequence of at least 17 consecutive nucleotides selected from the nucleotide sequence of SEQ ID No. 5 from nucleotide 1 to nucleotide 166 or of SEQ ID No. 24 from nucleotide 1 to nucleotide 1113, or said primer recognizing the 3' T-DNA flanking region of EE-GM5 comprises at its extreme 3' end a nucleotide sequence of at least 17 consecutive nucleotides selected from the nucleotide sequence of the complement of SEQ ID No. 6 from nucleotide 359 to nucleotide 691 or the nucleotide sequence of the complement of SEQ ID No. 25 from nucleotide 359 to nucleotide 1449, and said primer recognizing a sequence within the inserted T-DNA comprises at its 3' end at least 17 consecutive nucleotides selected from the complement of the nucleotide sequence of SEQ ID No. 5 from nucleotide 167 to nucleotide 353 or the nucleotide sequence of SEQ ID No. 6 from nucleotide 1 to nucleotide 358, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof.

13. The kit of paragraph 10, comprising a primer comprising the sequence of SEQ ID No. 12 and a primer comprising the sequence of SEQ ID No. 13 or comprising a primer comprising the sequence of SEQ ID No. 18 and a primer comprising the sequence of SEQ ID No. 19.

14. The kit of paragraph 10, further comprising a probe recognizing a sequence between the primer recognizing the 5' T-DNA flanking region and the primer recognizing the sequence within the inserted T-DNA, or recognizing a sequence between the primer recognizing the 3' T-DNA flanking region and the primer recognizing the sequence within the inserted T-DNA.

15. The kit of paragraph 14, wherein said probe recognizes part of said 5' T-DNA flanking region and part of the inserted T-DNA contiguous therewith, or wherein said probe recognizes part of said 3' T-DNA flanking region and part of the inserted T-DNA contiguous therewith.

16. The kit of paragraph 15, wherein said primers comprise the sequence of SEQ ID No. 12 and SEQ ID No. 13, and wherein said probe comprises the sequence of SEQ ID No. 14, or wherein said primers comprise the sequence of SEQ ID No. 18 and SEQ ID No. 19, and wherein said probe comprises the sequence of SEQ ID No. 20.

17. A primer pair suitable for use in an EE-GM5 specific detection, comprising a first primer comprising a sequence which, under optimized detection conditions specifically recognizes a sequence within the 5' or 3' T-DNA flanking region of the inserted T-DNA in EE-GM5, and a second primer comprising a sequence which, under optimized detection conditions specifically recognizes a sequence within the inserted T-DNA in EE-GM5 contiguous with said flanking 5' or 3' region, said 5' T-DNA flanking region comprising the nucleotide sequence of SEQ ID No. 5 from nucleotide 1 to nucleotide 166 or of SEQ ID No. 24 from nucleotide 1 to nucleotide 1113, said 3' T-DNA flanking region comprising the nucleotide sequence of the complement of SEQ ID No. 6 from nucleotide 359 to nucleotide 691 or the nucleotide sequence of the complement of SEQ ID No. 25 from nucleotide 359 to nucleotide 1449, said inserted T-DNA comprising the nucleotide sequence of SEQ ID No. 5 from nucleotide 167 to nucleotide 353, or the nucleotide sequence of SEQ ID No. 6 from nucleotide 1 to nucleotide 358, or the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof.

18. A primer comprising at its extreme 3' end the sequence of SEQ ID No. 12, or the sequence of SEQ ID No. 13, or the sequence of SEQ ID No. 18, or the sequence of SEQ ID No. 19.

19. A primer pair comprising a first primer comprising at its extreme 3' end the sequence of SEQ ID No. 12 and a second primer comprising at its extreme 3' end the sequence of SEQ ID No. 13, or comprising a first primer comprising at its extreme 3' end the sequence of SEQ ID No. 18 and a second primer comprising at its extreme 3' end the sequence of SEQ ID No. 19.

20. The method of paragraph 1, which method comprises hybridizing a nucleic acid of biological samples with a specific probe for EE-GM5.

21. The method of paragraph 20, wherein the sequence of said specific probe has at least 80% sequence identity with a sequence comprising part of the 5' T-DNA flanking sequence or the 3' T-DNA flanking sequence of EE-GM5 and the sequence of the inserted T-DNA contiguous therewith.

22. The method of paragraph 21, wherein the sequence of said specific probe comprises a sequence with at least 80% sequence identity to the sequence of any one of SEQ ID No. 1, 3, or 5 or the sequence of any one of SEQ ID No. 2, 4, or 6, or the complement of said sequences.

23. The method of paragraph 22, wherein said probe comprises the sequence of any one of SEQ ID No. 1 or 3 or the sequence of any one of SEQ ID No. 2 or 4.

24. A kit for identifying elite event EE-GM5 in biological samples, said kit comprising a specific probe, capable of hybridizing specifically to a specific region of EE-GM5.

25. The kit of paragraph 24, wherein the sequence of said specific probe has at least 80% sequence identity with a sequence comprising part of the 5' T-DNA flanking sequence or part of the 3' T-DNA flanking sequence of EE-GM5 and part of the sequence of the inserted T-DNA contiguous therewith.

26. The kit of paragraph 25, wherein the sequence of said specific probe comprises a nucleotide sequence having at least 80% sequence identity with any one of SEQ ID No.

1, 3 or 5 or any one of SEQ ID No. 2, 4 or 6, or the complement of said sequences.

27. A specific probe for the identification of elite event EE-GM5 in biological samples.

28. The probe of paragraph 27, which comprises a nucleotide sequence having at least 80% sequence identity with a sequence comprising part of the 5' T-DNA flanking sequence or part of the 3' T-DNA flanking sequence of EE-GM5 and part of the sequence of the inserted T-DNA contiguous therewith, or the complement thereof.

29. The probe of paragraph 28 which has at least 80% sequence identity with the sequence of any one of SEQ ID No. 1, 3 or 5 or the sequence of any one of SEQ ID No. 2, 4, or 6, or the complement of said sequences.

30. A specific probe comprising a nucleotide sequence being essentially similar to any one of SEQ ID No. 1, 3, or 5 or any one of SEQ ID No. 2, 4, or 6, or the complement of said sequences.

31. A specific probe comprising the sequence of SEQ ID No. 1 or 3 or the sequence of SEQ ID No. 2 or 4.

32. A method for confirming seed purity, which method comprises detection of an EE-GM5 specific region with a specific primer pair or probe which specifically recognize (s) the 5' or 3' T-DNA flanking region and the inserted T-DNA contiguous therewith in EE-GM5, in seed samples.

33. The method of paragraph 32, comprising amplifying a DNA fragment of between 50 and 1000 bp from a nucleic acid present in said biological samples using a polymerase chain reaction with at least two primers, one of said primers recognizing the 5' T-DNA flanking region of EE-GM5, said 5' T-DNA flanking region comprising the nucleotide sequence of SEQ ID No. 5 from nucleotide 1 to nucleotide 166 or of SEQ ID No. 24 from nucleotide 1 to nucleotide 1113, or the 3' T-DNA flanking region of EE-GM5, said 3' T-DNA flanking region comprising the nucleotide sequence of the complement of SEQ ID No. 6 from nucleotide 359 to nucleotide 691 or the nucleotide sequence of the complement of SEQ ID No. 25 from nucleotide 359 to nucleotide 1449, the other primer of said primers recognizing a sequence within the inserted T-DNA comprising the complement of the nucleotide sequence of SEQ ID No. 5 from nucleotide 167 to nucleotide 353 or the nucleotide sequence of SEQ ID No. 6 from nucleotide 1 to nucleotide 358, or within the nucleotide sequence of SEQ ID No. 11 from nucleotide 1 to nucleotide 7459, or the complement thereof, or within the nucleotide sequence of SEQ ID No. 23 from nucleotide 1114 to nucleotide 8572, or the complement thereof, and hybridizing a probe specific for the DNA fragment amplified with said at least two primers.

34. The method of paragraph 33, comprising amplifying a DNA fragment of 85 bp and wherein said primers comprise the sequence of SEQ ID No. 12 and SEQ ID No. 13, respectively, and wherein said probe comprises the sequence of SEQ ID No. 14, or amplifying a DNA fragment of 84 bp and wherein said primers comprise the sequence of SEQ ID No. 18 and SEQ ID No. 19, respectively, and wherein said probe comprises the sequence of SEQ ID No. 20.

35. A method for screening seeds for the presence of EE-GM5, which method comprises detection of an EE-GM5 specific region with a specific primer pair or probe which specifically recognize(s) the 5' or 3' T-DNA flanking region and the inserted T-DNA contiguous therewith in EE-GM5, in samples of seed lots.

36. The method of paragraph 35, comprising amplifying a DNA fragment of between 50 and 1000 bp from a nucleic acid present in said biological samples using a polymerase chain reaction with at least two primers, one of said primers recognizing the 5' T-DNA flanking region of the inserted T-DNA in EE-GM5, said 5' T-DNA flanking region comprising the nucleotide sequence of SEQ ID No. 5 from nucleotide 1 to nucleotide 166 or of SEQ ID No. 24 from nucleotide 1 to nucleotide 1113, or the 3' T-DNA flanking region of the inserted T-DNA in EE-GM5, said 3' T-DNA flanking region comprising the nucleotide sequence of the complement of SEQ ID No. 6 from nucleotide 359 to nucleotide 691 or the nucleotide sequence of the complement of SEQ ID No. 25 from nucleotide 359 to nucleotide 1449, the other primer of said primers recognizing a sequence within the inserted T-DNA comprising the complement of the nucleotide sequence of SEQ ID No. 5 from nucleotide 167 to nucleotide 353 or the nucleotide sequence of SEQ ID No. 6 from nucleotide 1 to nucleotide 358, or comprising the nucleotide sequence of SEQ ID No. 11 from nucleotide 1 to nucleotide 7459, or the complement thereof, or the nucleotide sequence of SEQ ID No. 23 from nucleotide 1114 to nucleotide 8572, or the complement thereof, and hybridizing a probe specific for the DNA fragment amplified with said at least two primers, such as a probe comprising the sequence of SEQ ID No. 1 or 3, or SEQ ID No. 2 or 4, or the complement thereof.

37. The method of paragraph 36, comprising amplifying a DNA fragment of 85 bp and wherein said primers comprise the sequence of SEQ ID No. 12 and SEQ ID No. 13, respectively, and wherein said probe comprises the sequence of SEQ ID No. 14.

38. A method for determining the zygosity status of a plant, plant material or seed comprising elite event EE-GM5, said method comprising amplifying DNA fragments of between 50 and 1000 bp from a nucleic acid present in said biological samples using a polymerase chain reaction with at least three primers, two of said primers specifically recognizing pre-insertion plant DNA, such as a primer comprising the nucleotide sequence of SEQ ID No. 21 and a primer comprising the nucleotide sequence of SEQ ID No. 19, the third of said primers recognizing a sequence within the inserted T-DNA, such as the nucleotide sequence of SEQ ID No. 18, such as said method using said primers wherein DNA fragments of 84 and 72 bp are amplified.

39. A method of detecting the presence of elite event EE-GM5 in biological samples through hybridization with a substantially complementary labeled nucleic acid probe in which the probe:target nucleic acid ratio is amplified through recycling of the target nucleic acid sequence, said method comprising:
a) hybridizing said target nucleic acid sequence to a first nucleic acid oligonucleotide comprising the nucleotide sequence of SEQ ID No. 5 from nucleotide position 167 to nucleotide position 184 or its complement or said first nucleic acid oligonucleotide comprising the nucleotide sequence of SEQ ID No. 6 from nucleotide position 341 to nucleotide position 358 or its complement;
b) hybridizing said target nucleic acid sequence to a second nucleic acid oligonucleotide comprising the nucleotide sequence of SEQ ID No. 5 from nucleotide 149 to nucleotide 166 or its complement or said nucleic acid oligonucleotide comprising the nucleotide sequence of SEQ ID No. 6 from nucleotide 359 to nucleotide 376 or its complement, wherein said first and second oligonucleotide overlap by at least one nucleotide and wherein either said first or said second oligonucleotide is labeled to be said labeled nucleic acid probe;
c) cleaving only the labeled probe within the probe:target nucleic acid sequence duplex with an enzyme which causes selective probe cleavage resulting in duplex disassociation, leaving the target sequence intact;
d) recycling of the target nucleic acid sequence by repeating steps (a) to (c); and
e) detecting cleaved labeled probe, thereby determining the presence of said target nucleic acid sequence, and detecting the presence of elite event EE-GM5 in said biological sample 40. A transgenic soybean plant, or cells, parts, seed or progeny thereof, each comprising elite event EE-GM5 in its genome, reference seed comprising said event having been deposited at the ATCC under deposit number PTA-123625.

41. The transgenic soybean plant, seed, cells, parts or progeny of paragraph 40, the genomic DNA of which, when analyzed using PCR for EE-GM5 with two primers comprising the nucleotide sequence of SEQ ID 12 and SEQ ID 13 respectively, yields a DNA fragment of 85 bp.

42. Seed comprising elite event EE-GM5, which is an inserted T-DNA at a specific position in the soybean genome, as is contained in the seed deposited at the ATCC under deposit number PTA-123625 or in derivatives therefrom.

43. A soybean plant, plant part, cell or tissue, or seed comprising elite event EE-GM5 obtainable from the seed of paragraph 42.

44. A soybean plant, or seed, cells or tissues thereof, each comprising elite event EE-GM5 in its genome, obtainable by propagation of and/or breeding with a soybean plant grown from the seed deposited at the ATCC under deposit number PTA-123625.

45. A soybean seed comprising elite event EE-GM5, reference seed comprising said event having been deposited at the ATCC under deposit number PTA-123625.

46. A transgenic soybean plant, cell or tissue, comprising elite event EE-GM5, obtainable from the seed of paragraph 45.

47. The soybean plant cell according to any one of paragraphs 40, 41, 43, 44 and 46, which is a non-propagating plant cell.

48. A method for producing a soybean plant or seed comprising elite event EE-GM5 comprising crossing a plant according to any one of paragraphs 40, 41, 43, 44 and 46 with another soybean plant, and planting the seed obtained from said cross.

49. Soybean genomic DNA comprising elite event EE-GM5.

50. A nucleic acid molecule comprising a nucleotide sequence essentially similar to the sequence of any one of SEQ ID No. 1, 3 or 5 or the sequence of any one of SEQ ID No. 2, 4, or 6, or the complement of said sequences, such as a nucleic acid molecule comprising a nucleotide sequence with at least 99% or at least 99.5% sequence identity to the nucleotide sequence of SEQ ID No. 5 or 24 or 6 or 25, or the complement thereof, such as said nucleic acid which confers tolerance to an HPPD inhibitor herbicide and/or SCN resistance in soybean.

51. The nucleic acid molecule of paragraph 50 comprising the nucleotide sequence of any one of SEQ ID No. 1 or 3 or SEQ ID No. 2 or 4, or the complement of said sequences, such as such nucleic acid molecule which also comprises the nucleotide sequence of SEQ ID No. 7 and 9 or a nucleotide sequence having at least 98% sequence identity thereto, or the complement thereof, or such nucleic acid molecule which comprises the nucleotide sequence of SEQ ID No. 11 from nucleotide position 188 to nucleotide position 7101, or a nucleotide sequence having at least 98% sequence identity thereto.

52. A soybean plant, cell, plant part, seed or progeny thereof comprising a nucleic acid molecule of any one of these paragraphs, such as a soybean plant, cell, plant part, seed or progeny thereof comprising a nucleic acid molecule comprising the nucleotide sequence of SEQ ID No. 1, 3 or 5 or the nucleotide sequence of SEQ ID No. 2, 4, or 6, or a soybean plant, cell, plant part, seed or progeny thereof, comprising in its genome the nucleotide sequence of SEQ ID No. 3 and the nucleotide sequence of SEQ ID No. 4, or a soybean plant, cell, plant part, seed or progeny thereof, comprising in its genome the nucleotide sequence of SEQ ID No. 5 and the nucleotide sequence of SEQ ID No. 6, or a soybean plant, cell, plant part, seed or progeny thereof, comprising in its genome the nucleotide sequence of SEQ ID No. 24 and the nucleotide sequence of SEQ ID No. 25, such as such a soybean plant also comprising a Cry14Ab-1-encoding chimeric and an HPPD-4-encoding chimeric gene, particularly such chimeric genes comprising the nucleotide sequence of SEQ ID No. 7 and 9, respectively.

53. A nucleic acid molecule comprising the nucleotide sequence of any one of SEQ ID No. 1, 3, or 5 or SEQ ID No. 2, 4, or 6, such as a nucleic acid molecule, which comprises the nucleotide sequence of SEQ ID No. 5 and SEQ ID No. 6, or the complement thereof, or such as a nucleic acid molecule, which comprises the nucleotide sequence of SEQ ID No. 24 and SEQ ID No. 25, or the complement thereof.

54. A transgenic soybean plant, plant cell, tissue, or seed, comprising in their genome event EE-GM5 characterized by a nucleic acid molecule comprising a nucleotide sequence essentially similar to the sequence of any one of SEQ ID No. 1, 3, 5, or 24 or the sequence of any one of SEQ ID No. 2, 4, 6, or 25, or the complement of said sequences, wherein said soybean plant also comprising a Cry14Ab-1-encoding chimeric and an HPPD-4-encoding chimeric gene.

55. A soybean plant, cell, tissue or seed, comprising EE-GM5 and comprising in the genome of its cells a nucleic acid sequence with at least 80%, 90%, 95% or 100% sequence identity to a sequence of any one of SEQ ID No. 1, 3 or 5 or a sequence of any one of SEQ ID No. 2, 4, or 6, or the complement of said sequences, such as a soybean plant also comprising a Cry14Ab-1-encoding chimeric and an HPPD-4-encoding chimeric gene, or such soybean plant, cell, tissue or seed, comprising in the genome of its cells a nucleic acid sequence with at least 80%, 90%, 95% or 100% sequence identity to the sequence of SEQ ID No. 24 or SEQ ID No. 25.

56. A soybean plant, plant cell, tissue, or seed, comprising in its genome a nucleic acid molecule comprising a nucleotide sequence with at least 99% sequence identity to the nucleotide sequence of SEQ ID No. 5 or 24 or SEQ ID No. 6 or 25, or the complement thereof, or such soybean plant, plant cell, tissue, or seed, comprising in its genome a nucleic acid molecule comprising a nucleotide sequence with at least 99% sequence identity to the nucleotide sequence of SEQ ID No. 5 or 24 and SEQ ID No. 6 or 25, or the complement thereof.

57. A soybean plant, plant cell, tissue, or seed, comprising in its genome a nucleic acid molecule hybridizing under standard stringency conditions to the nucleotide sequence of SEQ ID No. 5 or 6, or the complement thereof.
58. A nucleic acid molecule comprising a nucleotide sequence with at least 99% sequence identity to the nucleotide sequence of SEQ ID No. 5 or 24 or SEQ ID No. 6 or 25, or the complement thereof, such as a nucleic acid molecule comprising a nucleotide sequence with at least 99% sequence identity to the nucleotide sequence of SEQ ID No. 5 or 24 and SEQ ID No. 6 or 25, or the complement thereof.
59. A nucleic acid molecule comprising a nucleotide sequence hybridizing under standard stringency conditions to the nucleotide sequence of SEQ ID No. 5 or 6, or the complement thereof.
60. The nucleic acid molecule of any one of paragraphs 50, 51, 58 and 59, which also comprises the nucleotide sequence of SEQ ID No. 7 and 9.
61. A chimeric DNA comprising a T-DNA 5' flanking region, an inserted T-DNA, and a T-DNA 3' flanking region, wherein the sequence of said inserted T-DNA comprises the sequence of SEQ ID No. 11 from nucleotide 188 to nucleotide 7101 or a sequence at least 95, 96, 97, 98, 99, or at least 99.5% identical thereto, or wherein the sequence of said inserted T-DNA comprises the sequence of SEQ ID No. 7 and 9, and wherein said T-DNA 5' flanking region is located immediately upstream of and contiguous with said inserted T-DNA and comprises the sequence of SEQ ID No. 5 from nucleotide 1 to nucleotide 166 or a sequence at least 95, 96, 97, 98, 99, or at least 99.5% identical thereto, or of SEQ ID No. 24 from nucleotide 1 to nucleotide 1113, or a sequence at least 95, 96, 97, 98, 99, or at least 99.5% identical thereto, and wherein said T-DNA 3' flanking region is located immediately downstream of and contiguous with said inserted T-DNA and comprises the sequence of SEQ ID No. 6 from nucleotide 359 to nucleotide 691 or a sequence at least 95, 96, 97, 98, 99, or at least 99.5% identical thereto, or the nucleotide sequence of the complement of SEQ ID No. 25 from nucleotide 359 to nucleotide 1449, or a sequence at least 95, 96, 97, 98, 99, or at least 99.5% identical thereto.
62. A nucleic acid molecule comprising a nucleotide sequence with at least 98% sequence identity to the nucleotide sequence of SEQ ID No. 7 or the complement thereof, such as the nucleotide sequence of SEQ ID No.7, such as a DNA molecule comprising the nucleotide sequence of SEQ ID No. 11 from nucleotide 131 to 5276 or the complement thereof, or a sequence encoding a nematicidal Cry14Ab protein having at least 95, 96, 97, 98, or at least 99% sequence identity to SEQ ID No.7 or to the sequence of SEQ ID No. 11 from nucleotide position 131 to nucleotide position 5276, or the complement thereof.
63. A nucleic acid molecule comprising a nucleotide sequence with at least 98% sequence identity to the nucleotide sequence of SEQ ID No. 9 or the complement thereof, such as the nucleotide sequence of SEQ ID No.9, such as a DNA molecule comprising the nucleotide sequence of SEQ ID No. 11 from nucleotide 5382 to 7459, or the complement thereof, or a sequence having at least 95, 96, 97, 98, or at least 99% sequence identity to SEQ ID No. 9, or to the sequence of SEQ ID No. 11 from nucleotide position 5382 to nucleotide position 7459, or its complement, wherein said sequence encodes an HPPD protein providing tolerance to HPPD inhibitor herbicides when expressed in a plant.
64. A method for producing a soybean product, comprising obtaining soybean seed comprising elite event EE-GM5 as described above, and producing the soybean product therefrom.
65. The method of paragraph 64, wherein the soybean product is or comprises soybean meal, ground seeds, flour, or flakes.
66. The method of paragraph 4 or 65, wherein such soybean product comprises a nucleic acid specific for elite event EE-GM5, such as such product that comprises a nucleic acid that produces an amplicon diagnostic or specific for eventEE-GM5, such as the sequence of SEQ ID No. 1 or 3, or the sequence of SEQ ID No. 2 or 4.
67. A soybean product, comprising elite event EE-GM5 as described above, such as a soybean product produced from the soybean plant, cell, part, seed or progeny of any one of these paragraphs.
68. The soybean product of paragraph 67, wherein the soybean product is or comprises soybean meal, ground seeds, flour, or flakes.
69. The soybean product of paragraph 67 or 68, wherein said soybean product comprises a nucleic acid specific for elite event EE-GM5, such as such product that comprises a nucleic acid that produces an amplicon diagnostic or specific for event EE-GM5, such as the sequence of SEQ ID No. 1 or 3, or the sequence of SEQ ID No. 2 or 4, or their complement.
70. A method for protecting emerging soybean plants from competition by weeds, comprising treating a field in which seeds containing elite event EE-GM5 as described in any of these paragraphs were sown, with an HPPD inhibitor herbicide, wherein the plants are tolerant to the HPPD inhibitor herbicide.
71. A method for protecting emerging soybean plants from competition by weeds, comprising treating a field to be planted with soybean plants comprising elite event EE-GM5 as described above with an HPPD inhibitor herbicide, before the soybean plants are planted or the seeds are sown, followed by planting or sowing of said soybean plants or seeds in said pre-treated field, wherein the plants are tolerant to the HPPD inhibitor herbicide.
72. A method for controlling weeds in a field of soybean plants comprising elite event EE-GM5 as described above, comprising treating said field with an effective amount of an HPPD inhibitor herbicide, wherein the plants are tolerant to the HPPD inhibitor herbicide.
73. The method of any one of paragraphs 70 to 72, wherein the HPPD inhibitor herbicide is isoxaflutole, topramezone or mesotrione.
74. Use of a transgenic soybean plant, seed or progeny thereof, comprising elite event EE-GM5 as described above to produce soybean grain or seed.
75. Use of a soybean plant or seed comprising elite event EE-GM5 as described above in its genome to grow a nematode-resistant and/or HPPD inhibitor herbicide-tolerant plant.
76. Use of a soybean seed comprising elite event EE-GM5 to obtain a soybean product, wherein EE-GM5 is as described above, such as wherein such soybean product is or comprises ground soybean grain, soybean flour, soybean meal, or soybean flakes.

77. Use of a soybean plant or seed comprising elite event EE-GM5 as defined above, in combination with an HPPD inhibitor herbicide, for growing a field of soybean, or for growing a soybean crop.
78. A nucleic acid molecule obtainable from the seed deposited at the ATCC under accession number PTA-123625, wherein said nucleic acid molecule comprises the nucleotide sequence of any one of SEQ ID No. 1, 3, or 5 and the nucleotide sequence of any one of SEQ ID No. 2, 4, or 6.
79. A soybean plant, cell, part, or seed, each comprising in its genome elite event EE-GM5, wherein said elite event is the genetic locus comprising an inserted T-DNA containing a chimeric HPPD-4 protein-encoding gene and a chimeric Cry14Ab-1 protein-encoding gene, and 5' and 3' flanking sequences immediately surrounding said inserted T-DNA, as found in reference seed deposited at the ATCC under deposit number PTA-123625.
80. A progeny plant, cell, plant part or seed of the plant, cell, plant part or seed of paragraph 79, wherein said progeny plant, cell, plant part or seed comprises the nucleotide sequence of SEQ ID No. 3 and the nucleotide sequence of SEQ ID No. 4.
81. The soybean plant, cell, part, seed or progeny of paragraph 79, the genomic DNA of which, when analyzed using PCR with two primers comprising the nucleotide sequence of SEQ ID No. 18 and SEQ ID No. 19 respectively, yields a DNA fragment of 84 bp.
82. The plant of any one of the above paragraphs which is tolerant to isoxaflutole and/or topramezone and/or mesotrione, such as such a plant tolerant to isoxaflutole, topramezone and mesotrione.
83. A method for producing a soybean plant resistant to SCN and tolerant to HPPD inhibitor herbicides, comprising introducing resistance to SCN and tolerance to HPPD inhibitor herbicides into the genome of a soybean plant by crossing a first soybean plant lacking a Cry14Ab-1-encoding gene and lacking an HPPD-4-encoding gene with the soybean plant of any one of the above paragraphs, and selecting a progeny plant resistant to SCN and tolerant to HPPD inhibitor herbicides.
84. Use of a soybean plant or seed comprising elite event EE-GM5 as defined above to obtain a soybean crop, such as a soybean crop yielding better when infested by nematodes or Sudden Death Syndrome.
85. A method of producing a soybean crop with improved resistance to nematodes or Sudden Death Syndrome, comprising the steps (a) planting a field using the seed as described in any of the above paragraphs; and (b) harvesting the soybean seed produced on the plants grown from said seed, and optionally (c) applying to the field planted with said seeds before or after seed emergence, or on said soybean plants one or more doses of an HPPD inhibitor herbicide sufficient to kill weeds but which is tolerated by said soybean seeds or plants, such as wherein said nematodes are SCN or *Pratylenchus* species or root-knot nematode or reniform nematode species nematodes.
86. Use of the soybean seed described in the above paragraphs to prepare a processed food or feed commodity, wherein said processed food or feed commodity comprises a detectable amount of a nucleic acid comprising the nucleotide sequence of SEQ ID No. 1 and/or SEQ ID NO: 2, or the complement thereof.
87. The use of paragraph 86, wherein (i) said food or said feed commodity comprises soybean meal, soybean flour, soybean flakes, or soybean oil; (ii) said nucleic acid comprises the nucleotide sequence of SEQ ID NO: 3 and/or SEQ ID NO: 4, or the complement thereof; or (iii) said nucleic acid further comprises the nucleotide sequence contained in SEQ ID NO:7 and SEQ ID No. 9.
88. A soybean plant, seed or cell comprising in its genome elite event EE-GM5, wherein elite event EE-GM5 comprises a nucleotide sequence which is at least 90% identical to the sequence set forth in SEQ ID NO. 23, wherein said elite event comprises a chimeric HPPD-4-encoding gene and a chimeric Cry14Ab-1-encoding gene, wherein said plant, seed or cell is tolerant to an HPPD inhibitor herbicide and has SCN resistance.
89. The plant of paragraph 88, wherein elite event EE-GM5 comprises a nucleotide sequence which is at least 95% identical to the sequence set forth in SEQ ID NO. 23.
90. The plant of paragraph 88, wherein elite event EE-GM5 comprises a nucleotide sequence which is at least 99%, at least 99.5% or at least 99.9% identical to the sequence set forth in SEQ ID NO. 23.
91. A nucleic acid molecule comprising the nucleotide sequence of SEQ ID NO. 23 or a nucleotide sequence with at least 99% sequence identity to SEQ ID NO. 23, which confers tolerance to an HPPD inhibitor herbicide and/or nematode resistance, such as wherein said nematode is an SCN or *Pratylenchus* species or root-knot nematode or reniform nematode species nematode.
92. A nucleic acid molecule comprising the nucleotide sequence of SEQ ID No. 11 from nucleotide position 131 to nucleotide position 7941, or a nucleotide sequence having at least 95%, at least 96%, at least 97%, at least 98%, or at least 99% sequence identity thereto.
93. The nucleic acid molecule of paragraph 92, which encodes an HPPD protein tolerant to an HPPD inhibitor and a protein negatively affecting plant pest nematodes, such as SCN, RKN or *Pratylenchus* spp. nematodes.
94. The nucleic acid molecule of paragraph 93, which encodes the protein of SEQ ID No. 8 or a protein at least 99% identical thereto and the protein of SEQ ID No. 10, or a protein at least 99% identical thereto.
95. A method for controlling weeds and/or nematodes in a field to be planted with soybean plants, comprising the steps of: 1) treating said field with an HPPD inhibitor herbicide such as isoxaflutole, topramezone or mesotrione, and 2) planting or sowing of soybean plants or seeds comprising elite transformation event EE-GM5 as described above in said treated field, wherein reference seed comprising said elite event is deposited at the at the ATCC under deposit number PTA-123625.
96. A method of weed control, characterized in that it comprises the steps of: 1) planting of soybean plants or seeds tolerant to an HPPD inhibitor herbicide such as isoxaflutole, topramezone or mesotrione, in a field, and 2) application of an HPPD inhibitor herbicide, such as isoxaflutole, topramezone or mesotrione, in said field before planting said plants or seeds, or on said soybean plants or seeds after planting (can be before or after seed germination), wherein said plants or seeds comprise soybean elite transformation event EE-GM5 in their genome, reference seed comprising said elite event being deposited at the ATCC under deposit number PTA-123625.
97. A process for weed control, characterized in that it comprises the steps of: 1) treating a field to be planted with soybean plants or a field to be sown with soybean seeds with an HPPD inhibitor herbicide, such as isoxaflutole, topramezone or mesotrione, before the soybean plants are planted or the seeds are sown, and 2) planting soybean plants comprising soybean elite transformation event EE-GM5 or sowing soybean seeds comprising soybean elite transformation event EE-GM5 in said pretreated field, wherein reference seed comprising said soybean elite transformation event EE-GM5 is deposited at the ATCC under deposit number PTA-123625.

98. A method for reducing yield loss in a field to be planted with soybean plants, particularly a field that contains or is expected to contain nematodes such as SCN, RKN or *Pratylenchus* or reniform nematodes or a combination thereof, comprising the step of 1) obtaining plants or seed comprising elite transformation event EE-GM5 as described above, and 2) planting or sowing of soybean plants or seeds, wherein reference seed comprising said elite event is deposited at the at the ATCC under deposit number PTA-123625.

99. A method for increasing yield of soybean plants when planted in a field containing nematodes such as SCN, RKN or *Pratylenchus* or or reniform nematodes a combination thereof, comprising the step of 1) obtaining plants or seed comprising elite transformation event EE-GM5 as described above, and 2) planting or sowing of soybean plants or seeds, wherein reference seed comprising said elite event is deposited at the at the ATCC under deposit number PTA-123625.

100. A method for producing a soybean plant or seed tolerant to an HPPD inhibitor herbicide, such as isoxaflutole, topramezone or mesotrione, or for producing a soybean plant or seed tolerant to nematodes, such as SCN, RKN or *Pratylenchus* or reniform nematodes, or for producing a soybean plant or seed tolerant to an HPPD inhibitor herbicide, such as isoxaflutole, topramezone or mesotrione, and tolerant to nematodes, such as SCN, RKN or *Pratylenchus* or reniform nematodes, characterized by the step of introducing into the genome of a soybean plant or seed elite soybean transformation event EE-GM5 as described above, and optionally treating said plant or seed with an HPPD inhibitor herbicide, such as isoxaflutole, topramezone or mesotrione, or optionally treating the field in which said plant or seed will be planted with an HPPD inhibitor herbicide, such as isoxaflutole, topramezone or mesotrione, and planting said plant or seed in said pre-treated field.

101. A nucleic acid molecule that specifically characterizes soybean elite transformation event EE-GM5, characterized in that it comprises the nucleotide sequence of any one of SEQ ID No. 1, 3 or 5, which contains a part of soybean plant genomic DNA and a part of inserted foreign DNA of EE-GM5 downstream thereof and contiguous therewith, and/or characterized in that it comprises the nucleotide sequence of SEQ ID No. 2, 4, or 6, which contains a part of inserted foreign DNA of EE-GM5 and a part of soybean plant genomic DNA downstream thereof and contiguous therewith.

102. A plant or seed comprising EE-GM5 as described above, and also comprising tolerance or resistance to SCN, RKN or *Pratylenchus* or reniform nematodes, or a combination thereof, as provided by soybean resistance loci/genes.

103. The plant or seed of paragraph 102, wherein said plant or seed comprises EE-GM5 and any one or a combination of the SCN resistance alleles/loci of PI 548316, PI 567305, PI 437654, PI 90763, PI 404198B, PI 88788, PI 468916, PI 567516C, PI 209332, PI 438489B, PI 89772, Peking, PI 548402, PI 404198A, PI 561389B, PI 629013, PI 507471, PI 633736, PI 507354, PI 404166, PI 437655, PI 467312, PI 567328, PI 22897, or PI 494182.

104. A plant or seed comprising EE-GM5 as described above, also comprising tolerance to other herbicides, as provided by herbicide tolerance genes (either native or mutated soybean genes or transgenes), such as tolerance to glyphosate-. glufosinate-, sulfonylurea-, imidazolinone-, HPPD inhibitor-, dicamba-, 2,4-D-, or PPO inhibitor-based herbicides, or any combination thereof.

105. The plant or seed of paragraph 103 wherein said plant or seed comprises EE-GM5 as described above and one or more of the following soybean transformation events conferring herbicide tolerance: MST-FGØ72-3, SYN-ØØØH2-5, DAS-68416-4, DAS-444Ø6-6, MON-877Ø8-9, MON89788, MON-Ø4Ø32-6, ACS-GMØØ5-3, BPS-CV127-9, ACS-GMØØ6-4, MON-877Ø5-6, or event DP-3Ø5423-1.

106. A method to reduce severity of effects of Sudden Death Syndrome or Iron Deficiency Chlorosis on soybean plants in the presence of SCN infestation, or to increase yield of soybean plants in SCN-containing fields infested with Sudden Death Syndrome or in SCN-containing fields causing Iron Deficiency Chlorosis in soybean, which method comprises planting soybean plants or sowing soybean seeds comprising elite event EE-GM5, wherein reference seed comprising said elite event is deposited at the at the ATCC under deposit number PTA-123625.

BRIEF DESCRIPTION OF THE DRAWINGS

The following Examples, not intended to limit the invention to the specific embodiments described, may be understood in conjunction with the accompanying Figures, incorporated herein by reference, in which:

FIG. 2 shows an example of the result of the method described in Example 2.1 for a series of soybean samples containing EE-GM5 and conventional soybean samples. For each sample the S/B ratios for both the EE-GM5 specific reaction and the endogenous reaction are displayed. In this figure, samples within the lines marked with "a" are soybean samples not containing EE-GM5, samples within the lines marked with "b" are soybean samples containing EE-GM5, and samples within the box formed by the lines marked with "c" are inconclusive samples.

FIG. 3 shows an example of the result of the method described in Example 2.2 for a series of soybean samples containing EE-GM5 in a homozygous state, soybean samples containing EE-GM5 in a hemizygous state and conventional soybean samples. In this figure, samples within the lines marked with "a" are soybean samples containing EE-GM5 in a homozygous state, samples within the lines marked with "b" are soybean samples containing EE-GM5 in a hemizygous state, samples within the lines marked with "c" are soybean samples not containing EE-GM5, and samples within the box formed by the lines marked with "d" are inconclusive samples.

FIG. 4 shows an example of the results of the RT-PCR method described in Example 2.4 for low level presence analysis as performed on the calibration samples. "a", "b", "c", "d", "e" indicate the Ct values for calibration samples "A", "B", "C", "D", "E", respectively. Calibration samples "A", "B", "C", "D", "E" have decreasing amounts of EE-GM5 DNA.

FIG. 5 shows the average of the maximum plant phytotoxicity data recorded for herbicide treatment in several field trials across 2 years, for soybean plants containing event EE-GM5 as compared to untransformed/conventional soybean plants (Thorne). Numbers in ( ) below a treatment give the number of trials included in the bar, the number on top of each bar gives the average maximum phytotoxicity value for that treatment. Treatments applied were: IFT=isoxaflutole, MST=mesotrione, PE=pre-emergence, PO=post-emergence (at V2-V3 stage, with adjuvants crop oil concentrate and ammonium sulfate added to increase herbicide activity). Rates shown are in gram active ingredient/hectare (4× dose in pre-emergence, 2× dose in post-emergence).

EE-GM5 in original transformant background (Thorne) was tested in 9 different locations throughout Iowa, Illinois, Indiana, Missouri and Tennessee in 2015 and 2016, in SCN infested fields (ranging from low to high SCN infestation). The dot is the estimated yield of the homozygous event for each trial (as percent difference to the null), the horizontal lines represent the 95% confidence limits of the contrast between the homozygous event and the null segregate (if the line does not overlap the vertical line at 100 percent yield of null segregate, then the event was significantly different from the null segregate). "Across Locs" is the estimated yield of a combined analysis across all 9 locations.

Figure 7:
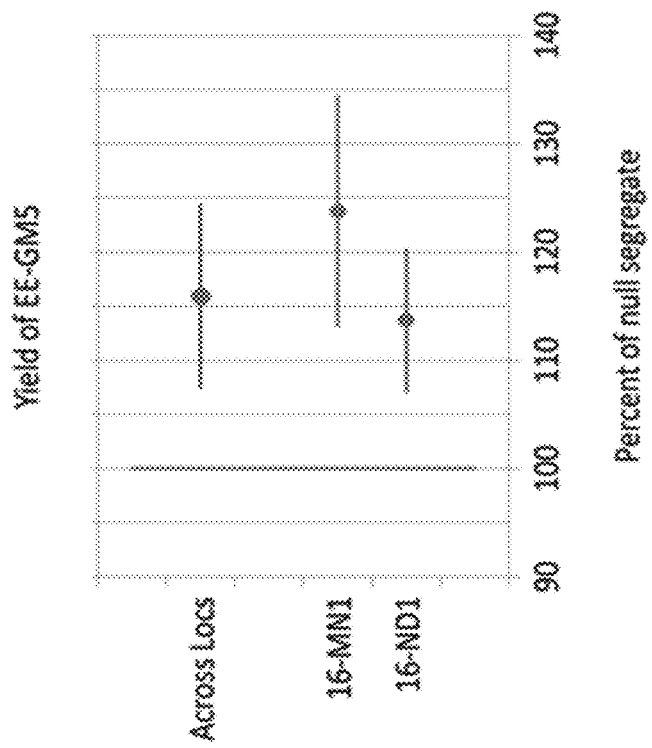

FIG. 7. Grain yield of EE-GM5 in SCN-susceptible elite background in SCN infested fields.

EE-GM5 was introgressed (BC2F3) into an elite MG I (maturity group I) line that is susceptible to SCN and was tested at one location in Minnesota and one location in North Dakota in 2016 (each with high SCN infestation levels). The dot is the estimated yield of the homozygous event for each trial (as percent difference to the null), the horizontal line around the dot represents the 95% confidence limits of the contrast between the homozygous event and the null segregant (if the line does not overlap the vertical line at 100 percent yield of null segregant, then the event was significantly different from the null segregant). "Across Locs" is the estimated yield of a combined analysis across both locations.

Figure 8:
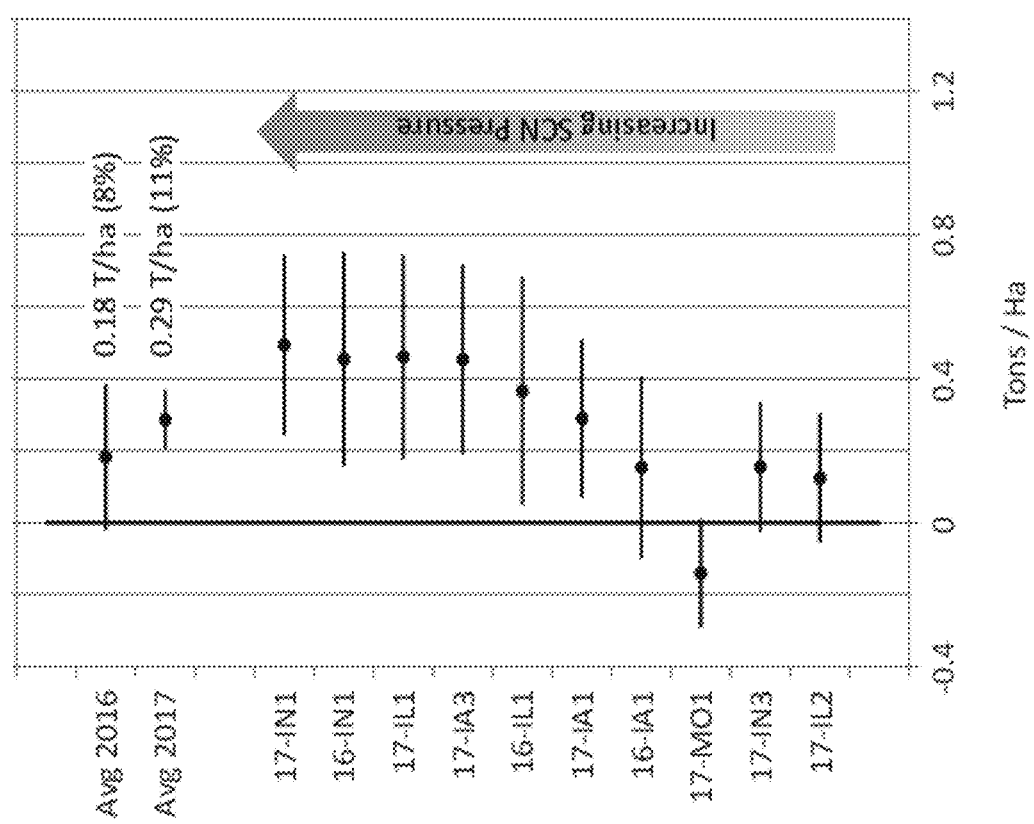

FIG. 8. Grain yield of EE-GM5 in elite SCN-resistant background in SCN infested fields.

EE-GM5 was crossed into an elite MG III (maturity group III) line that is resistant to SCN (due to the rhg1 locus from PI 88788) and was tested at 3 locations in 2016 (trials starting with "16" such as 16-IN1) and at 7 locations in 2017 (trials starting with "17", such as 17-IN1), ranging from low to high SCN infestation levels (see arrow, locations with low SCN pressure are at the bottom of the figure (e.g., 17-IL2) and locations with high SCN pressure at the top (e.g., 17-IN1)). SCN pressure was assigned by considering several factors including known field history, SCN populations in the soil, relative yields of resistant and susceptible control varieties, soil characteristics (pH and % sand) and a visual evaluation of root infestation in susceptible entries. The dot is the average yield difference (in tons per hectare) of the homozygous event in each trial compared to the null segregant, the horizontal line around the dot represents the 95% confidence limits of the contrast between the homozygous event and the null segregant (if the line does not overlap the vertical line at 0 difference with the null segregant, then the yield for the event was significantly different from the null segregant). "Avg" is the average yield across all locations in each year.

Figure 9:
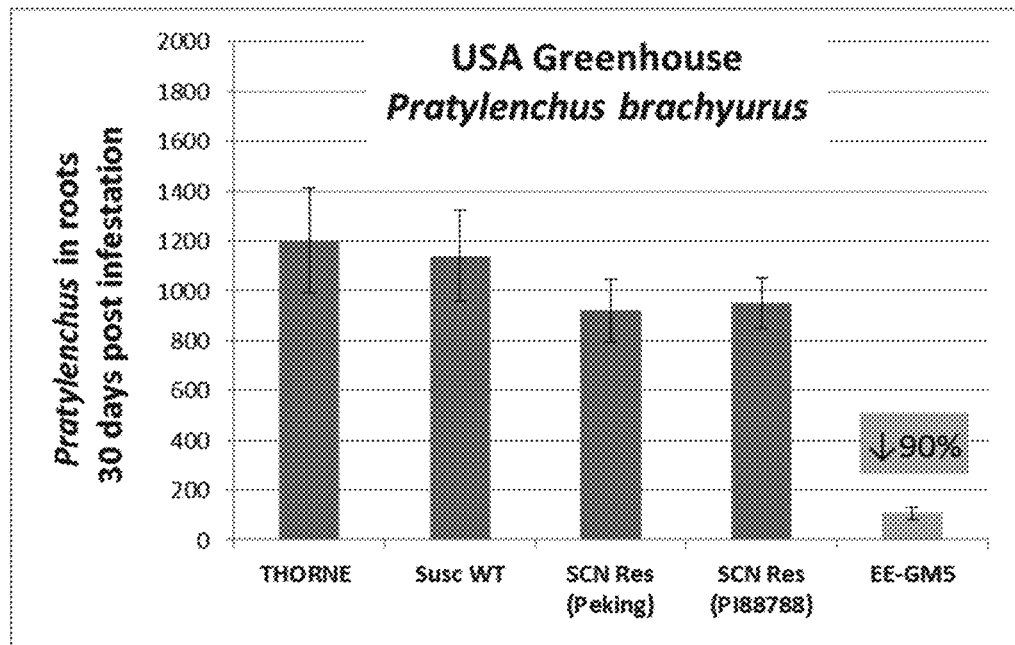

FIG. 9. *Pratylenchus* resistance greenhouse assay in the USA

Elite soybean plants with EE-GM5 control *Pratylenchus brachyurus* in US greenhouse assays. Plants with EE-GM5 ("EE-GM5") were compared to other elite soybean lines: one SCN susceptible Maturity Group (MG)3 line ("THORNE"), one MG3 SCN susceptible line, one MG 6.2 SCN susceptible line and one MG9 SCN susceptible line ("Susc WT" shows the average for these 3 lines), one MG3 SCN resistant line (with the rhg1 resistance allele from PI 88788, "SCN Res (PI 88788)"), and one MG 6.2 SCN resistant line with the rhg1 and Rhg4 SCN resistance from Peking ("SCN Res (Peking)"). Plotted are the average numbers of *Pratylenchus* in roots 30 days after infestation (5 plants per entry), also showing the variation observed across varieties (as typically seen in greenhouse assays). Results show ~90% control of *Pratylenchus* across EE-GM5 lines. Soybean lines with native SCN resistance (from Peking or PI 88788) do not control *Pratylenchus brachyurus*.

Figure 10:
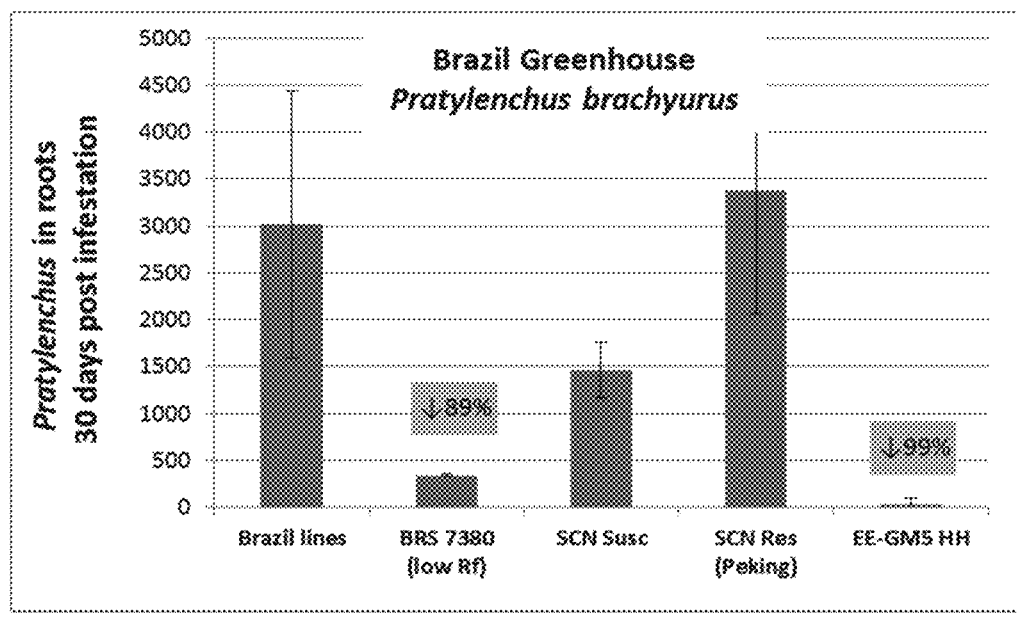

FIG. 10. *Pratylenchus* resistance greenhouse assay in Brazil

Soybean plants homozygous for EE-GM5 ("EE-GM5 HH") significantly reduce *Pratylenchus brachyurus* in soybean roots. *Pratylenchus brachyurus* were isolated from local fields in Brazil. EE-GM5 plants (in two different US elite lines (both maturity group 6.2, one SCN-susceptible and one with Peking SCN-resistance ("EE-GM5")) and five Brazilian soybean lines, with limited *Pratylenchus* control ("Brazil lines"), one Brazilian line labeled as low Rf (reproductive factor) for *Pratylenchus* ("BRS 7380 (low Rf)"), one US elite line (maturity group 6.2) that is SCN-susceptible ("SCN Susc") and one US elite line (MG 6.2) with Peking SCN-resistance ("SCN Res (Peking)") were evaluated for *Pratylenchus* control in a greenhouse assay in Brazil. Plotted are the averages of those entries, also showing the variation observed across varieties (as typically seen in greenhouse assays). One Brazilian soybean line (BRS 7380), showed ~89% reduction of *Pratylenchus*. EE-GM5 lines gave ~99% control of *Pratylenchus*. Soybean lines that carry Peking native resistance to SCN do not control *Pratylenchus brachyurus*.

Figure 11:
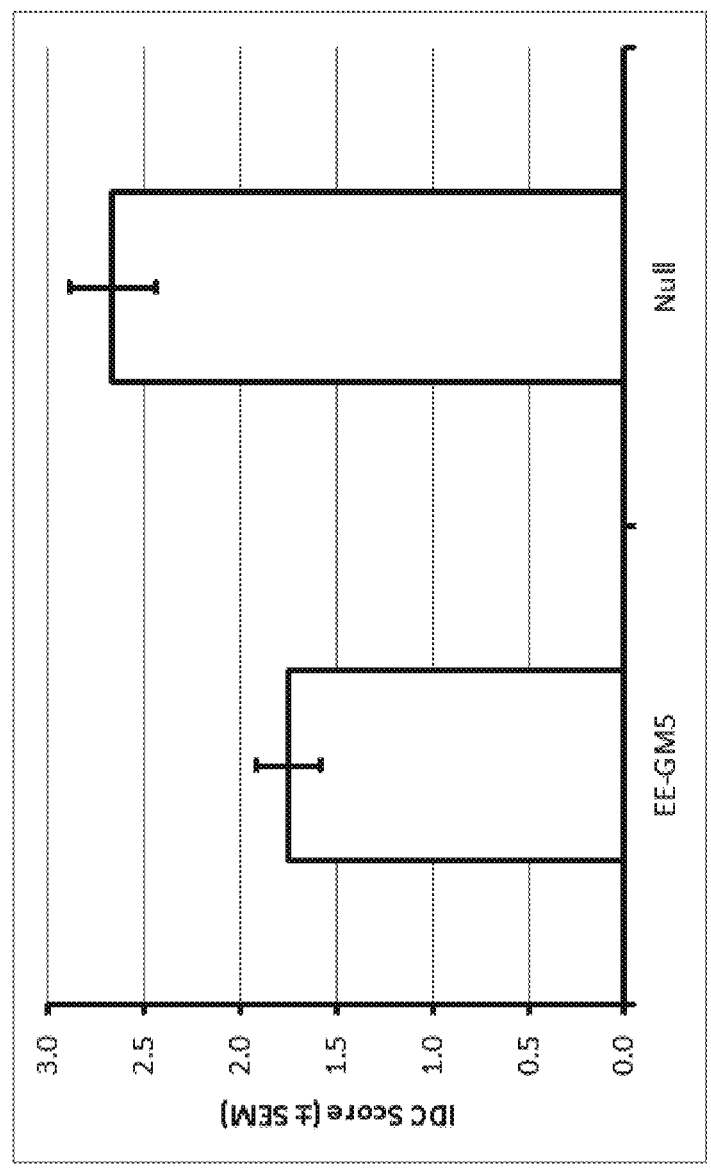

FIG. 11. Iron Deficiency Chlorosis (IDC) scores for EE-GM5 plants compared to nulls FIG. 11 shows the IDC scores of soybean plants with EE-GM5 at one location (with high SCN infestation). The trial was a split-plot design (4 plots per entry) looking at the effect of the event in 3 different backgrounds (2 susceptible soybean lines and 1 with SCN resistance from PI 88788). Shown are the averages of IDC scores for plants with event EE-GM5 ("EE-GM5") and the corresponding null segregant ("Null", lacking EE-GM5) across three genetic backgrounds (1 SCN-resistant, 1 SCN-susceptible, and the SCN-susceptible Thorne background). One bar represents 12 total plots. The vertical lines indicate the standard error ("SEM" is the Standard Error of the Mean).

DETAILED DESCRIPTION OF A PREFERRED EMBODIMENT

In this invention, EE-GM5 has been identified as an elite event from a population of transgenic soybean plants in the development of nematode resistant soybean (*Glycine max*) comprising a gene coding for 4-hydroxy phenylpyruvate dioxygenase (HPPD) inhibitor tolerance combined with a gene conferring resistance to nematodes, each under control of a plant-expressible promoter. Specific tools for use in the identification of elite event EE-GM5 in biological samples are described herein.

The incorporation of a recombinant DNA molecule in the plant genome typically results from transformation of a cell or tissue. The particular site of incorporation is usually due to random integration.

The DNA introduced into the plant genome as a result of transformation of a plant cell or tissue with a recombinant DNA or "transforming DNA", and originating from such transforming DNA is hereinafter referred to as "inserted T-DNA" comprising one or more "transgenes". The transgenes of EE-GM5 are a nematode resistance and an HPPD inhibitor herbicide tolerance gene. "Plant DNA" in the context of the present invention will refer to DNA originating from the plant which is transformed. Plant DNA will usually be found in the same genetic locus in the corresponding wild-type plant. The inserted T-DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the region of the plant genome referred to as "pre-insertion plant DNA" (or "pre-insertion locus") can be associated with a deletion of plant DNA, referred to as "target site deletion". A "flanking region" or "flanking sequence" as used herein refers to a sequence of at least 10 bp, at least 20 bp, at least 50 bp, and up to 5000 bp of DNA different from the introduced T-DNA, preferably DNA from the plant genome which is located either immediately upstream of and contiguous with or immediately downstream of and contiguous with the inserted T-DNA. Transformation procedures leading to random integration of the inserted T-DNA will result in transformants with different flanking regions, which are characteristic and unique for each transformant. When the recombinant DNA is introduced into a plant through traditional crossing, its insertion site in the plant genome, or its flanking regions, will generally not be changed.

An "isolated nucleic acid (sequence/molecule)" or "isolated DNA (sequence/molecule)", as used herein, refers to a nucleic acid or DNA (sequence/molecule) which is no longer in the natural environment it was isolated from, e.g., the nucleic acid sequence in another (bacterial) host or in a plant genome, or a nucleic acid or DNA (sequence/molecule) fused to DNA or nucleic acid (sequence/molecule) from another origin, such as when contained in a chimeric gene under the control of a (heterologous) plant-expressible promoter. Any nucleic acid or DNA of this invention, including any primer, can also be non-naturally-occurring, such as a nucleic acid or DNA with a sequence identical to a sequence occurring in nature, but having a label (missing from the naturally-occurring counterpart), or with a sequence having at least one nucleotide addition or replacement or at least one internal nucleotide deletion compared to a naturally-existing nucleotide, or with a sequence having a sequence identity below 100% (not identical) to a naturally-existing nucleic acid or DNA or a fragment thereof, or a nucleic acid or DNA with a sequence consisting of nucleotide sequences from different origins that do not occur together in nature (a chimeric or hybrid DNA), or a man-made synthetic nucleic acid or DNA with a sequence different from the natural nucleic acid or DNA or a fragment thereof.

An event is defined as a (artificial) genetic locus that, as a result of genetic engineering, carries an inserted T-DNA or transgene comprising at least one copy of a gene of interest or of the genes of interest. The typical allelic states of an event are the presence or absence of the inserted T-DNA.

An event is characterized phenotypically by the expression of the transgene or transgenes. At the genetic level, an event is part of the genetic make-up of a plant. At the molecular level, an event can be characterized by the restriction map (e.g., as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique. An event is characterized by the inserted T-DNA and at least one of the flanking sequences.

An elite event, as used herein, is an event which is selected from a group of events, obtained by transformation with the same transforming DNA, based on an optimal trait efficacy and superior expression, stability of the transgene(s) and its compatibility with optimal agronomic characteristics of the plant comprising it. Thus the criteria for elite event selection are one or more, preferably two or more, advantageously all of the following:
  a) trait efficacy;
  b) that the presence of the inserted T-DNA does not compromise other desired characteristics of the plant, such as those relating to agronomic performance or commercial value;
  c) that the event is characterized by a well-defined molecular configuration which is stably inherited and for which appropriate tools for identity control can be developed;
  d) that the gene(s) of interest show(s) a correct, appropriate and stable spatial and temporal phenotypic expression, at a commercially acceptable level in a range of environmental conditions in which the plants carrying the event are likely to be exposed in normal agronomic use.

It is preferred that the inserted T-DNA is associated with a position in the plant genome that allows easy introgression into desired commercial genetic backgrounds.

The status of an event as an elite event is confirmed by introgression of the elite event in different relevant genetic backgrounds and observing compliance with one, two, three or all of the criteria e.g. a), b), c) and d) above.

An "elite event" thus refers to a genetic locus comprising an inserted T-DNA, which meets the above-described criteria. A plant, plant material or progeny such as seeds can comprise one or more different elite events in its genome.

The tools developed to identify an elite event or the plant or plant material comprising an elite event, or products which comprise plant material comprising the elite event, are based on the specific genomic characteristics of the elite event, such as, a specific restriction map of the genomic region comprising the inserted T-DNA, molecular markers or the sequence of the flanking region(s) of the inserted T-DNA.

Once one or both of the flanking regions of the inserted T-DNA have been sequenced, primers and/or probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers", one recognizing a sequence within the 5' or 3' T-DNA flanking region of the elite event and the other recognizing a sequence within the inserted T-DNA. The primers preferably have a sequence of between 15 and 35 nucleotides which under optimized PCR conditions "specifically recognize" a sequence within the 5' or 3' T-DNA flanking region of the elite event and the inserted T-DNA of the elite event respectively, so that a specific fragment ("integration fragment" or discriminating amplicon) is amplified from a nucleic acid sample comprising the elite event. This means that only the targeted integration fragment, and no other sequence in the plant genome or inserted T-DNA, is amplified under optimized PCR conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides, selected from the 5' T-DNA flanking sequence (SEQ ID No. 5 from nucleotide 1 to nucleotide 166 or SEQ ID No. 24 from nucleotide 1 to nucleotide 1113 or plant genomic sequences upstream thereof and contiguous therewith) at their 3' end (primers recognizing 5' T-DNA flanking sequences); or oligonucleotides ranging in length from 17 nt to about 200 nt, comprising a nucleotide sequence of at least 17 consecutive nucleotides, preferably 20 consecutive nucleotides, selected from the 3' T-DNA flanking sequence (complement of SEQ ID No. 6 from nucleotide 359 to nucleotide 691 or the nucleotide sequence of the complement of SEQ ID No. 25 from nucleotide 359 to nucleotide 1449 or plant genomic sequences downstream thereof and contiguous therewith) at their 3' end (primers recognizing 3' T-DNA flanking sequences); or oligonucleotides ranging in length from 17 nt to about 200 nt, comprising a nucleotide sequence of at least 17 consecutive nucleotides, preferably 20 consecutive nucleotides, selected from the inserted T-DNA sequences (complement of SEQ ID No. 5 from nucleotide 167 to nucleotide 353 or sequence of SEQ ID No. 6 from nucleotide 1 to nucleotide 358, or the sequence of SEQ ID No. 11 from nucleotide 1 to nucleotide 7459 or the sequence of SEQ ID No. 23 from nucleotide 1114 to nucleotide 8572, or its complement) at their 3' end (primers recognizing inserted T-DNA).

It will be understood that primers recognizing the 5' T-DNA flanking sequences can be used in a PCR reaction together with primers recognizing the inserted T-DNA which are selected from the complement of SEQ ID No. 5 from nucleotide 167 to nucleotide 353 or T-DNA sequences downstream thereof and contiguous therewith, whereas primers recognizing the 3' T-DNA flanking sequences can be used in a PCR reaction together with primers recognizing the inserted T-DNA which are selected from the sequence of SEQ ID No. 6 from nucleotide 1 to nucleotide 358, or T-DNA upstream thereof and contiguous therewith. Primers recognizing inserted T-DNA can also be selected from the sequence of SEQ ID No. 11 from nucleotide 1 to nucleotide 7459, or the sequence of SEQ ID No. 23 from nucleotide 1114 to nucleotide 8572, or the complement thereof.

The primers may of course be longer than the mentioned 17 consecutive nucleotides, and may, e.g., be 20, 21, 30, 35, 50, 75, 100, 150, 200 nt long or even longer. The primers may entirely consist of nucleotide sequence selected from the mentioned nucleotide sequences of flanking sequences and inserted T-DNA sequences. However, the nucleotide sequence of the primers at their 5' end (i.e., outside of the 17 consecutive nucleotides at the 3' end) is less critical. Thus, the 5' sequence of the primers may comprise or consist of a nucleotide sequence selected from the flanking sequences or inserted T-DNA, as appropriate, but may contain several (e.g., 1, 2, 5, or 10) mismatches in comparison with the T-DNA or T-DNA flanking DNA. The 5' sequence of the primers may even entirely be a nucleotide sequence unrelated to the flanking sequences or inserted T-DNA, such as, e.g., a nucleotide sequence representing one or more restriction enzyme recognition sites, or such as nucleotide sequences capable of binding other oligonucleotides, such as labelled oligonucleotides, such as FRET cassettes (LGC genomics; see Semagn et al., 2014, Mol Breeding 33:1-14, and U.S. Pat. No. 7,615,620). Such unrelated sequences or flanking DNA sequences with mismatches should preferably not be longer than 100, more preferably not longer than 50 or even 25 nucleotides. The primers can also be modified with a label, such as a fluorescent label.

Moreover, suitable primers may comprise or consist (essentially) of a nucleotide sequence at their 3' end spanning the joining region between the 5' or 3' T-DNA flanking region-derived sequences and the inserted T-DNA sequences (located at nucleotides 166 and 167 in SEQ ID No. 5 and nucleotides 358 and 359 in SEQ ID No. 6, or nucleotides 1113 and 1114 in SEQ ID No. 24 and nucleotides 358 and 359 in SEQ ID No. 25) provided the mentioned 3'-located 17 consecutive nucleotides are not derived exclusively from either the inserted T-DNA or the T-DNA flanking sequences in SEQ ID No. 5 or 6 or SEQ ID No. 24 or 25.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides with their complementary nucleotide according to Chargaff's rules (A⇔T; G⇔C) and reading the sequence in the 5' to 3' direction, i.e., in opposite direction of the represented nucleotide sequence.

Examples of suitable primers are the oligonucleotide sequences of SEQ ID no. 13 or SEQ ID No. 19 or SEQ ID No. 26 or 27 (3' or 5' T-DNA flanking sequence recognizing primer), or SEQ ID No. 12 or SEQ ID No. 18 or SEQ ID No. 28 or 29 (inserted T-DNA recognizing primer for use with the 3' or 5' T-DNA flanking sequence recognizing primers).

Preferably, the amplified fragment has a length of between 50 and 500 nucleotides, such as a length between 50 and 150 nucleotides. The specific primers may have a sequence which is between 80 and 100% identical to a sequence within the 5' or 3' T-DNA flanking region of the elite event and the inserted T-DNA of the elite event, respectively, provided the mismatches still allow specific identification of the elite event with these primers under optimized PCR conditions. The range of allowable mismatches however, can easily be determined experimentally and are known to a person skilled in the art.

Detection of integration fragments can occur in various ways, e.g., via size estimation after gel analysis. The integration fragments may also be directly sequenced. Other sequence specific methods for detection of amplified DNA fragments are also known in the art. Amplified DNA fragments can also be detected using labelled sequences and detection of the label. For example, a labelled probe can be included in the reaction mixture which specifically binds to the amplified fragment. In one embodiment, the labelled probe (FRET hybridization probe) can comprise a fluorescent label and a quencher, such that the FRET cassette is no longer quenched and emits fluorescence when bound to the PCR product. Alternatively, a labelled FRET cassette, i.e., an oligonucleotide labeled with a fluorescent label and a quencher, can be included in the reaction mixture which specifically binds one of the primers in the reaction mixture, such as a FRET cassette directed to a 5' extension of the primer used in the reaction mixture (see, e.g., Semagn et al., 2014, Mol Breeding 33:1-14, and U.S. Pat. No. 7,615,620). Fluorescence can be measured using methods known in the art. Fluorescence can be measured real-time, i.e., during each cycle of the PCR reaction. Fluorescence can also be measured at the end of the PCR reaction.

As the sequence of the primers and their relative location in the genome are unique for the elite event, amplification of the integration fragment will occur only in biological samples comprising (the nucleic acid of) the elite event. Preferably when performing a PCR to identify the presence of EE-GM5 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in "PCR Applications Manual" (Roche Molecular Biochemicals, 2nd Edition, 1999, or 3$^{rd}$ Edition, 2006) and other references. The optimal conditions for the PCR, including the sequence of the specific primers, are specified in a "PCR (or Polymerase Chain Reaction) Identification Protocol" for each elite event. It is however understood that a number of parameters in the PCR Identification Protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR Identification Protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying EE-GM5 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g., via labeling of the nucleic acid or probe), whereby the formation of this hybrid indicates the presence of EE-GM5. Such identification methods based on hybridization with a specific probe (either on a solid phase carrier or in solution) have been described in the art. The specific probe is preferably a sequence which, under optimized conditions, hybridizes specifically to a region comprising part of the 5' or 3' T-DNA flanking region of the elite event and part of the inserted T-DNA contiguous therewith (hereinafter referred to as "specific region"). Preferably, the specific probe comprises a sequence of between 50 and 500 bp, or of 100 to 350 bp which is at least 80%, or between 80 and 85%, or between 85 and 90%, or between 90 and 95%, or between 95% and 100% identical (or complementary), or is identical (or complementary) to the nucleotide sequence of a specific region of EE-GM5. Preferably, the specific probe will comprise a sequence of about 15 to about 100 contiguous nucleotides identical (or complementary) to a specific region of the elite event.

Oligonucleotides suitable as PCR primers for detection of the elite event EE-GM5 can also be used to develop a PCR-based protocol to determine the zygosity status of plants containing the elite event. To this end, two primers recognizing the wild-type locus before integration are designed in such a way that they are directed towards each other and have the insertion site located in between the primers. These primers may contain primers specifically recognizing the 5' and/or 3' T-DNA flanking sequences of EE-GM5. This set of primers recognizing the wild-type locus before integration, together with a third primer complementary to transforming DNA sequences (inserted T-DNA) allows simultaneous diagnostic PCR amplification of the EE-GM5 specific locus, as well as of the wild type locus. If the plant is homozygous for the transgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic and wild type locus.

Alternatively, to determine the zygosity status of plants containing the elite event, two primers recognizing the wild-type locus before integration are designed in such a way that they are directed towards each other, and that one primer specifically recognizes the 5' or the 3' T-DNA flanking sequences contained in SEQ ID No. 5 or 6 or in SEQ ID No. 24 or 25, and that one primer specifically recognizes the 3' or the 5' T-DNA flanking sequences contained within SEQ ID No. 6 or 5 or SEQ ID No. 24 or 25, or specifically recognizes the pre-insertion locus. For the current invention, a suitable primer pair recognizing the wild type locus before integration is a primer pair containing one primer comprising or consisting (essentially) of the nucleotide sequence of SEQ ID No. 21, and one primer comprising or consisting (essentially) of the nucleotide sequence of SEQ ID No. 19. This set of primers, together with a third primer complementary to transforming DNA sequences (inserted T-DNA), or complementary to transforming DNA sequences and the 5' or 3' T-DNA flanking sequences contiguous therewith, and in a direction towards the primer which specifically recognizes the 5' or the 3' T-DNA flanking sequences (such as a primer comprising or consisting (essentially) of the nucleotide sequence of SEQ ID No. 18, which is in a direction towards the primer comprising or consisting (essentially) of the nucleotide sequence of SEQ ID No. 19) allow simultaneous diagnostic PCR amplification of the EE-GM5 specific locus, as well as of the wild type locus. If the plant is homozygous for the transgenic locus or the corresponding wild type locus, the diagnostic PCR will give rise to a single PCR product typical for either the transgenic or wild type locus. If the plant is hemizygous for the transgenic locus, two locus-specific PCR products will appear, reflecting both the amplification of the transgenic and wild type locus.

Detection of the PCR products typical for the wild-type and transgenic locus can be based on determination of the length of the PCR products which can be typical for the wild-type and transgenic locus. Alternatively, detection of the PCR products typical for the wild-type and transgenic locus can be performed by modification of the primer specific for the pre-insertion locus and by modification of the primer specific for the inserted T-DNA, and detection of incorporation into a PCR product of the modified primers. For example, the primer specific for the pre-insertion locus and the primer specific for the inserted T-DNA can be labeled using a fluorescent label, wherein the labels are different for the two primers. Fluorescence can be detected when the primer is incorporated into a PCR product. If the plant is homozygous for the transgenic locus or the corresponding wild type locus, fluorescence can be detected of the label of the primer specific for the inserted T-DNA only or of the primer specific for the pre-insertion locus only. If the plant is hemizygous for the transgenic locus, fluorescence can be detected of both the label of the primer specific for the inserted T-DNA and of the primer specific for the pre-insertion locus, reflecting both the amplification of the transgenic and wild type locus.

Alternatively, the primer specific for the pre-insertion locus and the primer specific for the inserted T-DNA can have a 5' extension which specifically binds a labeled FRET cassette, i.e. an oligonucleotide labelled with a fluorescent label and a quencher, wherein the 5' extension and the corresponding FRET cassettes are different for the two primers (see, e.g., Semagn et al., 2014, Mol Breeding 33:1-14, and U.S. Pat. No. 7,615,620). Fluorescence can be detected when the primer is incorporated into a PCR product and, subsequently, the FRET cassette is incorporated in the PCR product. If the plant is homozygous for the transgenic locus or the corresponding wild type locus, fluorescence can be detected of the FRET cassette specifically binding to the primer specific for the inserted T-DNA only or of the FRET cassette specifically binding to the primer specific for the pre-insertion locus only. If the plant is hemizygous for the transgenic locus, fluorescence can be detected of both of the FRET cassette specifically binding to the primer specific for the inserted T-DNA and of the FRET cassette specifically binding to the primer specific for the pre-insertion locus, reflecting both the amplification of the transgenic and wild type locus.

If the plant is homozygous for the transgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic and wild type locus.

Alternatively, to determine the zygosity status of plants containing the elite event, presence of the event can be determined in a PCR reaction in a quantitative way as described in the Examples. To this end, two primers recognizing the event EE-GM5 are designed in such a way that they are directed towards each other, wherein one primer specifically recognizes the 5' or 3' T-DNA flanking sequence contained within SEQ ID No. 5 or 6 or within SEQ ID No. 24 or 25, and wherein one primer specifically recognizes the inserted T-DNA within SEQ ID no. 5 or 6 or within SEQ ID No. 24 or 25 or within SEQ ID No. 11 or 23. This set of primers allows PCR amplification of the EE-GM5 specific locus. The amplified DNA fragment can quantitatively be detected using a labeled probe which is included in the reaction mixture which specifically binds to the amplified fragment. The labeled probe can comprise a fluorescent label and a quencher, such that label is no longer quenched and emits fluorescence when bound to the PCR product. Fluorescence can be measured real-time, i.e. during each cycle of the PCR reaction, using methods known in the art. The PCR cycle at which the fluorescence exceeds a certain threshold level is a measure for the amount of EE-GM5 specific locus in the biological sample which is analyzed, and the zygosity status can be calculated based on reference homozygous and heterozygous samples.

Alternatively, zygosity status of plants comprising EE-GM5 can also be determined based on copy number analysis, using the Taqman chemistry and principles of Real-Time PCR. The alternative method will typically include a EE-GM5 specific reaction to quantify the EE-GM5 copy number, and a endogenous gene-specific reaction for normalization of the EE-GM5 copy number. Samples containing the EE-GM5 event in a homozygous state will have a relative copy number that is two-fold higher than hemizygous samples. Azygous samples will not amplify the EE-GM5 sequence in such a method.

Furthermore, detection methods specific for elite event EE-GM5 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage", incorporated herein by reference). To this end, the target sequence is hybridized with a labeled first nucleic acid oligonucleotide comprising the nucleotide sequence of SEQ ID No. 5 from nucleotide position 167 to nucleotide position 184 or its complement or comprising the nucleotide sequence of SEQ ID No. 6 from nucleotide position 341 to nucleotide position 358 or its complement, and is further hybridized with a second nucleic acid oligonucleotide comprising the nucleotide sequence of SEQ ID No. 5 from nucleotide 149 to nucleotide 166 or its complement or said nucleic acid oligonucleotide comprising the nucleotide sequence of SEQ ID No. 6 from nucleotide 359 to nucleotide 376 or its complement, wherein said first and second oligonucleotide overlap by at least one nucleotide.

The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

In one embodiment is provided a method of detecting the presence of elite event EE-GM5 in biological samples through hybridization with a substantially complementary labeled nucleic acid probe in which the probe:target nucleic acid ratio is amplified through recycling of the target nucleic acid sequence, said method comprising:

a) hybridizing said target nucleic acid sequence to a first nucleic acid oligonucleotide comprising the nucleotide sequence of SEQ ID No. 5 from nucleotide position 167 to nucleotide position 184 or its complement or said first nucleic acid oligonucleotide comprising the nucleotide sequence of SEQ ID No. 6 from nucleotide position 341 to nucleotide position 358 or its complement;

b) hybridizing said target nucleic acid sequence to a second nucleic acid oligonucleotide comprising the nucleotide sequence of SEQ ID No. 5 from nucleotide 149 to nucleotide 166 or its complement or said second nucleic acid oligonucleotide comprising the nucleotide sequence of SEQ ID No. 6 from nucleotide 359 to nucleotide 376 or its complement, wherein said first and second oligonucleotide overlap by at least one nucleotide and wherein either said first or said second oligonucleotide is labeled to be said labeled nucleic acid probe;

c) cleaving only the labeled probe within the probe:target nucleic acid sequence duplex with an enzyme which causes selective probe cleavage resulting in duplex disassociation, leaving the target sequence intact;

d) recycling of the target nucleic acid sequence by repeating steps (a) to (c); and e) detecting cleaved labeled probe, thereby determining the presence of said target nucleic acid sequence, and detecting the presence of elite event EE-GM5 in said biological samples.

Two nucleic acids are "substantially complementary" as used herein, when they are not the full complement of each other (as defined herein), such as when their sequences are at least 80%, at least 85%, at least 90%, at least 95%, or at least 99% complementary to each other.

A "kit" as used herein refers to a set of reagents for the purpose of performing the method of the invention, more particularly, the identification of the elite event EE-GM5 in biological samples or the determination of the zygosity status of EE-GM5 containing plant material. More particularly, a preferred embodiment of the kit of the invention comprises at least one or two specific primers, as described above for identification of the elite event, or three specific primers, or two specific primers and one specific probe, as described above for the determination of the zygosity status. Optionally, the kit can further comprise any other reagent described herein in the PCR Identification Protocol or any of the other protocols as described herein for EE-GM5 detection. Alternatively, according to another embodiment of this invention, the kit can comprise a specific probe, as described above, which specifically hybridizes with nucleic acid of biological samples to identify the presence of EE-GM5 therein. Optionally, the kit can further comprise any other reagent (such as but not limited to hybridizing buffer, label) for identification of EE-GM5 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed or industrial products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4.

Computer-assisted analysis and interpretation of sequence data, including sequence alignment as described above, can, e.g., be conveniently performed using the sequence analysis software package of the Genetics Computer Group (GCG, University of Wisconsin Biotechnology Center). Sequences are indicated as "essentially similar" when such sequences have a sequence identity of at least about 75%, at least about 80%, at least about 85%, at least about 90%, at least about 95%, at least about 98%, or at least about 99%, or at least 95%, at least 96%, at least 97%, at least 98%, at least 99%, at least 99.5% or at least 99.9%. It is clear that when RNA sequences are said to be essentially similar or have a certain degree of sequence identity with DNA sequences, thymidine (T) in the DNA sequence is considered equal to uracil (U) in the RNA sequence. Also, it is clear that small differences or mutations may appear in DNA sequences over time and that some mismatches can be allowed for the event-specific primers or probes of the invention, so any DNA sequence indicated herein in any embodiment of this invention for any 3' or 5' T-DNA flanking DNA or for any insert or inserted T-DNA or any primer or probe of this invention, also includes sequences essentially similar to the sequences provided herein, such as sequences hybridizing to or with at least 90%, 95%, 96%, 97%, 98%, or at least 99% sequence identity to the sequence given for any 3' or 5' T-DNA flanking DNA, for any primer or probe or for any insert or inserted T-DNA of this invention, such as a nucleotide sequence differing in 1 to 200, 1 to 150, 1 to 100, 1 to 75, 1 to 50, 1 to 30, 1 to 20, 1 to 10, 1 to 5, or 1 to 3 nucleotides from any given sequence.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers or probes, refers to the fact that the specific primers or probes specifically hybridize to a nucleic acid sequence in the elite event under the conditions set forth in the method (such as the conditions of the PCR Identification Protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological sample is a sample of a plant, plant material or products comprising plant material. The term "plant" is intended to encompass soybean (*Glycine max*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for EE-GM5, implying the presence of nucleic acids in the samples. Thus the methods referred to herein for identifying elite event EE-GM5 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, such as promoter, leader, trailer, and/or transcript termination sequences (possibly also including a DNA encoding a targeting or transit peptide).

The present invention also relates to the development of an elite event EE-GM5 in soybean plants comprising this event, the progeny plants and seeds comprising elite event EE-GM5 obtained from these plants and to the plant cells, or plant material derived from plants comprising this event. Plants comprising elite event EE-GM5 can be obtained as described in the Examples. This invention also relates to seed comprising elite event EE-GM5 deposited at the ATCC under deposit number PTA-123625 or derivatives therefrom comprising elite event EE-GM5. "Derivatives (of seed)" as used herein, refers to plants which can be grown from such seed, progeny resulting from selfing, crossing or backcrossing, as well as plant cells, organs, parts, tissue, cell cultures, protoplasts, and plant material of same.

Soybean plants or plant material comprising EE-GM5 can be identified according to any one of the identification protocols for EE-GM5 as described in the Examples, including the End-Point method for EE-GM5 identity analysis in Example 2.1, the End-Point method for EE-GM5 identity and zygosity analysis as described in Example 2.2, the Real-Time PCR method for EE-GM5 Low Level Presence analysis as described in Example 2.3, or the Real-Time PCR for EE-GM5 low level presence analysis as described in Example 2.4. Briefly, soybean genomic DNA present in the biological sample is amplified by PCR using a primer which specifically recognizes a sequence within the 5' or 3' T-DNA flanking sequence of EE-GM5 such as the primer with the sequence of SEQ ID NO: 13 or SEQ ID No. 19, and a primer which recognizes a sequence in the inserted T-DNA, such as the primer with the sequence of SEQ ID No. 12 or SEQ ID No. 18, or with a primer which recognizes the 5' or 3' T-DNA flanking sequence of EE-GM5 and the inserted T-DNA contiguous therewith. DNA primers which amplify part of an endogenous soybean sequence are used as positive control for the PCR amplification. If upon PCR amplification, the material yields a fragment of the expected size or gives rise to fluorescence of the expected fluorescent label, the material contains plant material from a soybean plant harboring elite event EE-GM5.

Plants harboring EE-GM5 are characterized by their nematode resistance, particularly SCN, lesion nematode and/or root-knot nematode ("RKN") and/or reniform nematode resistance, as well as by their tolerance to HPPD inhibitors such as isoxaflutole, topramezone or mesotrione. Soybean plants in different commercially available varieties harboring EE-GM5 are also characterized by having agronomical characteristics that are comparable to the corresponding non-transgenic isogenic commercially available varieties, in the absence of HPPD inhibitor herbicide application and SCN infestation. It has been observed that the presence of an inserted T-DNA in the insertion region of the soybean plant genome described herein, confers particularly interesting phenotypic and molecular characteristics to the plants comprising this event.

Also provided herein is a method for producing a soybean plant resistant to SCN and tolerant to HPPD inhibitor herbicides, comprising introducing resistance to SCN and tolerance to HPPD inhibitor herbicides into the genome of a soybean plant by crossing a first soybean plant lacking a Cry14Ab-1-encoding gene and lacking an HPPD-4-encoding gene with an EE-GM5-containing soybean plant, and selecting a progeny plant resistant to SCN and tolerant to HPPD inhibitor herbicides. Resistance to SCN can be measured using a standard SCN greenhouse assay, e.g., www-.plantpath.iastate.edu/tylkalab/greenhouse-resistance-screening and www.plantmanagementnetwork.org/pub/php/review/2009/sce08/.

One embodiment of this invention provides an elite event in soybean plants, obtainable by insertion of 2 transgenes at a specific location in the soybean genome, which elite event confers resistance to nematodes and tolerance to an HPPD inhibitor herbicide such as isoxaflutole, topramezone or mesotrione on such soybean plants, and wherein such elite event has an agronomic performance essentially similar to isogenic lines (as used herein, "isogenic lines" or "near-isogenic lines" are soybean lines of the same genetic background but lacking the transgenes, such as plants of the same genetic background as the plant used for transformation, or segregating sister lines ("nulls") having lost the transgenes). Particularly, the current invention provides an elite event in soybean plants, wherein the insertion or presence of said elite event in the genome of such soybean plants does not appear to cause an increased susceptibility to disease, does not cause a yield penalty, or does not cause increased lodging, as compared to isogenic lines or to commercial soybean cultivars. Hence, the current invention provides an elite event in soybean plants, designated as EE-GM5, which results in soybean plants that have improved resistance to nematodes and can tolerate the application of an HPPD inhibitor herbicide such as isoxaflutole, topramezone or mesotrione without negatively affecting the yield of said soybean plants compared to isogenic lines, which soybean plants are not statistically significantly different in their disease susceptibility, or lodging, from isogenic soybean plants or from commercial soybean cultivars. These characteristics make the current elite event a valuable tool in a nematode control and weed resistance management program. In one embodiment, event EE-GM5 is combined with one or more soybean GM events providing tolerance to any one or a combination of glyphosate-based, glufosinate-based, HPPD inhibitor-based, sulfonylurea- or imidazolinone-based, AHAS- or ALS-inhibiting and/or auxin-type (e.g., dicamba, 2,4-D) herbicides, such as Event EE-GM3 (aka FG-072, MST-FGØ72-3, described in WO2011063411, USDA-APHIS Petition 09-328-01p), Event SYHTOH2 (aka 0H2, SYN-ØØØH2-5, described in WO2012/082548 and 12-215-01p), Event DAS-68416-4 (aka Enlist Soybean, described in WO2011/066384 and WO2011/066360, USDA-APHIS Petition 09-349-01p), Event DAS-44406-6 (aka Enlist E3, DAS-44406-6, described in WO2012/075426 and USDA-APHIS 11-234-01p), Event MON87708 (dicamba-tolerant event of Roundup Ready 2 Xtend Soybeans, described in WO2011/034704 and USDA-APHIS Petition 10-188-01p, MON-87708-9), Event MON89788 (aka Genuity Roundup Ready 2 Yield, described in WO2006/130436 and USDA-APHIS Petition 06-178-01p), Event 40-3-2 (aka Roundup Ready, GTS 40-3-2, MON-04032-6, described in USDA-APHIS Petition 93-258-01), Event A2704-12 (aka LL27, ACS-GM005-3, described in WO2006108674 and USDA-APHIS Petition 96-068-01p), Event 127 (aka BPS-CV127-9, described in WO2010/080829), Event A5547-127 (aka LL55, ACS-GM006-4, described in WO2006108675 and in USDA-APHIS Petition 96-068-01p), event MON87705 (MON-87705-6, Vistive Gold, published PCT patent application WO2010/037016, USDA-APHIS Petition 09-201-01p), or event DP305423 (aka DP-305423-1, published PCT patent application WO2008/054747, USDA-APHIS Petition 06-354-01p), or EE-GM5 is combined with a combination of the following events: Event MON98788×MON87708 (aka Roundup Ready 2 Xtend Soybeans, MON-87708-9×MON-89788-1), Event HOS×Event 40-3-2 (aka Plenish High Oleic Soybeans×Roundup Ready Soybeans), Event EE-GM3×EE-GM2 (aka FG-072xLL55, described in WO2011063413), Event MON 87701×MON 89788 (aka Intacta RR2 Pro Soybean, MON-87701-2×MON-89788-1), DAS-81419-2× DAS-44406-6 (aka Conkesta™ Enlist E3™ Soybean, DAS-81419-2×DAS-44406-6), Event DAS-68416-4×Event MON 89788 (aka Enlist™ RoundUp Ready® 2 Soybean, DAS-68416-4×MON-89788-1), Event MON-87769-7× Event MON-89788-1 (aka Omega-3×Genuity Roundup Ready 2 Yield Soybeans), Event MON 87705×Event MON 89788 (aka Vistive Gold, MON-87705-6×MON-89788-1), or Event MON87769×Event MON89788 (aka Omega-3× Genuity Roundup Ready 2 Yield Soybeans, MON-87769-7×MON-89788-1).

Provided herein is also a soybean plant or part thereof comprising event EE-GM5, wherein representative soybean seed comprising event EE-GM5 has been deposited under ATCC accession number PTA-123625. Further provided herein are seeds of such plants, comprising such event, as well as a soybean product produced from such seeds, wherein said soybean product comprises event EE-GM5. Such soybean product can be or can comprise soybean meal, ground soybean grain, soybean flakes, or a product comprising any of these processed soybean products. Particularly, such soybean product comprises a nucleic acid that produces an amplicon diagnostic of or specific for event EE-GM5, such amplicon comprising the sequence of any one of SEQ ID No. 1 or 3 or SEQ ID No. 2 or 4. Also provided herein is a method for producing a soybean product, comprising obtaining a soybean seed or grain comprising event EE-GM5, and producing such soybean product therefrom. Also provided herein is a method of obtaining processed food, feed or industrial products derived from soybean grain, such as soybean oil, soybean protein, lecithin, soybean milk, tofu, margarine, biodiesel, biocomposites, adhesives, solvents, lubricants, cleaners, foam, paint, ink, candles, soybean-oil or soybean protein-containing food or (animal) feed products, said method comprising obtaining grain comprising EE-GM5 and producing said processed food, feed or industrial product from said grain. In one embodiment, this process can also include the step of a obtaining a soybean seed or plant comprising event EE-GM5, growing said seed or plant in a field, and harvesting soybean grain. Optionally, this method includes application of an HPPD inhibitor herbicide such as IFT, topramezone or mesotrione before planting, before emergence, after emergence or over the top of plants comprising EE-GM5. In one embodiment, the above soybean-derived processed food, feed or industrial products are included in this invention, such as such processed products that produce an EE-GM5 event-specific amplicon using the methods described herein, or that comprise the nucleotide sequence of any one of SEQ ID No. 1, 3 or 5, or SEQ ID No. 2, 4, or 6.

Also provided herein is a soybean plant, which is progeny of any of the above soybean plants, and which comprises event EE-GM5, such as a progeny plant or seed of any one of the above soybean plants that comprises the sequence of SEQ ID No. 1 or 3 or the sequence of SEQ ID No. 2 or 4, or a progeny plant or seed of any one of the above soybean plants that comprises the sequence of SEQ ID No. 1 or 3 and the sequence of SEQ ID No. 2 or 4, or a progeny plant or seed of any one of the above soybean plants that comprises the sequence of SEQ ID No. 5 or SEQ ID No. 24 or the sequence of SEQ ID No. 6 or SEQ ID No. 25, or a progeny plant or seed of any one of the above soybean plants that comprises the sequence of SEQ ID No. 5 or SEQ ID No. 24 and the sequence of SEQ ID No. 6 or SEQ ID No. 25.

Further provided herein is a method for producing a soybean plant resistant to nematodes and tolerant to isoxaflutole and/or topramezone and/or mesotrione herbicide, comprising introducing into the genome of such plant event EE-GM5, particularly by crossing a first soybean plant lacking event EE-GM5 with a soybean plant comprising EE-GM5, and selecting a progeny plant resistant to nematodes and tolerant to isoxaflutole and/or topramezone and/or mesotrione herbicide.

Also provided herein is a soybean plant resistant to nematodes and tolerant to isoxaflutole, topramezone or mesotrione herbicide with acceptable agronomical characteristics, comprising a Cry14Ab-1-encoding gene and HPPD-4-encoding gene, and capable of producing an amplicon diagnostic for event EE-GM5. Also provided herein are the specific isolated amplicons (DNA sequence fragments) as such, that can be obtained using the specific detection tools described herein, particularly amplicons including in their sequence a DNA fragment originating from 5' or 3' T-DNA flanking DNA and the DNA inserted in the plant genome by transformation, as defined herein.

Further provided herein is a method for controlling weeds in a field of soybean plants comprising event EE-GM5, or a field to be planted with such soybean plants (wherein said plants are planted in said field after treatment), comprising treating the field with an effective amount of an HPPD inhibitor herbicide such as an isoxaflutole-based or topramezone-based or mesotrione-based herbicide, wherein such plants are tolerant to such herbicide.

Further provided herein is a DNA comprising the sequence of SEQ ID No. 5 or 6 or a sequence essentially similar thereto, and any plant, cell, tissue or seed, particularly of soybean, comprising such DNA sequence, such as a plant, cell, tissue, or seed comprising EE-GM5. Also included herein is any soybean plant, cell, tissue or seed, comprising the DNA sequence (heterologous or foreign to a conventional soybean plant, seed, tissue or cell) of SEQ ID No. 5 or 6, or comprising a DNA sequence with at least 99% or 99.5% sequence identity to the sequence of SEQ ID No. 5 or 24 or SEQ ID No. 6 or 25.

Also described is a chimeric DNA comprising an inserted T-DNA, wherein the sequence of said inserted T-DNA comprises the sequence of SEQ ID No. 11 from nucleotide 1 to nucleotide 7459, or SEQ ID No. 23 from nucleotide 1114 to nucleotide 8572, or a sequence with at least 97, 98, 99, 99.5 or at least 99.9% sequence identity thereto, flanked by a 5' and a 3' T-DNA flanking region, wherein the 5' T-DNA flanking region immediately upstream of and contiguous with said inserted T-DNA is characterized by a sequence comprising the sequence of SEQ ID No. 5 from nucleotide 1 to nucleotide 166 or of SEQ ID No. 24 from nucleotide 1 to nucleotide 1113, and wherein the 3' T-DNA flanking region immediately downstream of and contiguous with said inserted T-DNA is characterized by a sequence comprising the sequence of SEQ ID No. 6 from nucleotide 359 to nucleotide 691, or the nucleotide sequence of the complement of SEQ ID No. 25 from nucleotide 359 to nucleotide 1449. In one embodiment, the sequence of said inserted T-DNA consists of the sequence of SEQ ID No. 11 from nucleotide 1 to nucleotide 7459, or SEQ ID No. 23 from nucleotide 1114 to nucleotide 8572, or a sequence with at least 97, 98, 99, 99.5 or at least 99.9% sequence identity thereto, flanked by part of a 5' and a 3' T-DNA flanking region, wherein the part of said 5' T-DNA flanking region immediately upstream of and contiguous with said inserted T-DNA is characterized by a sequence consisting of the sequence of SEQ ID No. 5 from nucleotide 1 to nucleotide 166 or of SEQ ID No. 24 from nucleotide 1 to nucleotide 1113, or a sequence with at least 97, 98, 99, 99.5 or at least 99.9% sequence identity thereto, and wherein the part of the 3' T-DNA flanking region immediately downstream of and contiguous with said inserted T-DNA is characterized by a sequence consisting of the sequence of SEQ ID No. 6 from nucleotide 359 to nucleotide 691 or the nucleotide sequence of the complement of SEQ ID No. 25 from nucleotide 359 to nucleotide 1449, or a sequence with at least 97, 98, 99, 99.5 or at least 99.9% sequence identity thereto.

Chimeric DNA refers to DNA sequences, including regulatory and coding sequences that are not found together in nature. Accordingly, a chimeric DNA may comprise DNA regions adjacent to each other that are derived from different sources, or which are arranged in a manner different from that found in nature. Examples of a chimeric DNA are the sequences of SEQ ID No. 5 or 6.

Also provided herein is a transgenic soybean plant, plant cell, tissue, or seed, comprising in their genome event EE-GM5 characterized by a nucleic acid molecule comprising a nucleotide sequence essentially similar to SEQ ID No. 1 or 3 and a nucleic acid molecule comprising a nucleotide sequence essentially similar to SEQ ID No. 2 or 4, or the complement of said sequences, as well as a soybean plant, plant cell, tissue, or seed, comprising in their genome event EE-GM5 characterized by a nucleic acid molecule comprising a nucleotide sequence essentially similar to SEQ ID No. 5 or 24 and SEQ ID No. 6 or 25, or the complement of said sequences.

Even further provided herein is a soybean plant, cell, tissue or seed, comprising EE-GM5, characterized by comprising in the genome of its cells a nucleic acid sequence with at least 80%, at least 85%, at least 90%, at least 95%, at least 96%, at least 97%, at least 98%, at least 99% or 100% sequence identity to any one of SEQ ID No. 1, 3, 5 or 24 and a nucleic acid sequence with at least 80%, at least 85%, at least 90%, at least 95%, at least 96%, at least 97%, at least 98%, at least 99% or 100% sequence identity to any one of SEQ ID No. 2, 4, 6, or 25, or the complement of said sequences.

The term "isoxaflutole", as used herein, refers to the herbicide isoxaflutole [i.e. (5-cyclopropyl-4-isoxazolyl)[2-(methylsulfonyl)-4-(trifluoromethyl)phenyl]methanone], the active metabolite thereof, diketonitrile, and any mixtures or solutions comprising said compound. HPPD inhibiting herbicides useful for application on the event of this invention are the diketonitriles, e.g., 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1, 3-fione; other isoxazoles; and the pyrazolinates, e.g. topramezone [i.e. [3-(4,5-dihydro-3-isoxazolyl)-2-methyl-4-(methylsulfonyl) phenyl](5-hydroxy-1-methyl-1H-pyrazol-4-yl)methanone], and pyrasulfotole [(5-hydroxy-1,3-dimethylpyrazol-4-yl(2-mesyl-4-trifluaromethylphenyl) methanone]; or mesotrione [2-[4-(Methylsulfonyl)-2-nitrobenzoyl]cyclohexane-1,3-dione]; or 2-chloro-3-(methylsulfanyl)-N-(1-methyl-1H-tetrazol-5-yl)-4-(trifluoromethyl) benzamide]; or 2-methyl-N-(5-methyl-1,3,4-oxadiazol-2-yl)-3-(methylsulfonyl)-4-(trifluoromethyl)benzamide; or pyrazofen [2-[4-(2,4-dichlorobenzoyl)-1,3-dimethylpyrazol-5-yloxy]acetophenone].

In one embodiment of this invention, a field to be planted with soybean plants containing the EE-GM5 event, can be treated with an HPPD inhibitor herbicide, such as isoxaflutole ('IFT'), topramezone or mesotrione, or with both an HPPD inhibitor herbicide and glyphosate, before the soybean is sown, which cleans the field of weeds that are killed by the HPPD inhibitor and/or glyphosate, allowing for no-till practices, followed by planting or sowing of the soybeans in that same pre-treated field later on (burn-down application using an HPPD inhibitor herbicide). The residual activity of IFT will also protect the emerging and growing soybean plants from competition by weeds in the early growth stages. Once the soybean plants have a certain size, and weeds tend to re-appear, an HPPD inhibitor or a mixture of an HPPD inhibitor with a selective (conventional) soybean herbicide or a mixture of an HPPD inhibitor with a herbicide that is non-selective in soybean (e.g., glyphosate or glufosinate) but for which the plants contain a tolerance gene/locus so that said plants are tolerant to said herbicide, can be applied as post-emergent herbicide over the top of the plants.

In another embodiment of this invention, a field in which seeds containing the EE-GM5 event were sown, can be treated with an HPPD inhibitor herbicide, such as IFT, topramezone or mesotrione, before the soybean plants emerge but after the seeds are sown (the field can be made weed-free before sowing using other means, including conventional tillage practices such as ploughing, chisel ploughing, or seed bed preparation), where residual activity will keep the field free of weeds killed by the herbicide so that the emerging and growing soybean plants have no competition by weeds (pre-emergence application of an HPPD inhibitor herbicide). Once the soybean plants have a certain size, and weeds tend to re-appear, an HPPD inhibitor—or an HPPD inhibitor-soybean selective (conventional) herbicide mixture or a mixture of an HPPD inhibitor with a herbicide that is non-selective in soybean (e.g., glyphosate or glufosinate) but for which the plants contain a tolerance gene/locus so that said plants are tolerant to said herbicide—can be applied as post-emergent herbicide over the top of the plants. In one embodiment of the invention is provided a process for weed control comprising sowing in a field EE-GM5-containing soybean seeds, and treating said field with an HPPD inhibitor herbicide before plants emerge from said seed, but after the seeds are sown.

In another embodiment of this invention, plants containing the EE-GM5 event can be treated with an HPPD inhibitor herbicide, such as IFT, topramezone or mesotrione, over the top of the soybean plants that have emerged from the seeds that were sown, which cleans the field of weeds killed by the HPPD inhibitor, which application can be together with (e.g., in a spray tank mix), followed by or preceded by a treatment with a selective soybean post-emergent herbicide, or a herbicide that is non-selective in soybean (e.g., glyphosate or glufosinate) for which the plants contain a tolerance gene/locus so that said plants are tolerant to said herbicide, over the top of the plants (post-emergence application of an HPPD inhibitor herbicide (with or without said soybean selective or non-selective herbicide)).

Also, in accordance with the current invention, soybean plants harboring EE-GM5 (which may also contain another herbicide tolerance soybean event/trait as described herein) may be treated with, or soybean seeds harboring EE-GM5 may be coated with, any soybean insecticide, herbicide or fungicide.

The following examples describe the development and identification of elite event EE-GM5, the development of different soybean lines comprising this event, and the development of tools for the specific identification of elite event EE-GM5 in biological samples.

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown TA, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

In the description and examples, reference is made to the following sequences in the enclosed Sequence Listing:
SEQ ID No. 1: 5' junction EE-GM5
SEQ ID No. 2: 3' junction EE-GM5
SEQ ID No. 3: EE-GM5 5' junction
SEQ ID No. 4: EE-GM5 3' junction
SEQ ID No. 5: EE-GM5 5' region
SEQ ID No. 6: EE-GM5 3' region
SEQ ID No. 7: cry14Ab-1.b coding sequence
SEQ ID No. 8: Cry14Ab-1 protein amino acid sequence
SEQ ID No. 9: hppdPf-4 Pa coding sequence
SEQ ID No. 10: HPPD-4 protein amino acid sequence SEQ ID No. 11: transformation plasmid pSZ8832—sequence between T-DNA borders
SEQ ID No. 12: primer PRIM1038
SEQ ID No. 13: primer PRIM1039
SEQ ID No. 14: probe TM1788
SEQ ID No. 15: primer KVM164
SEQ ID No. 16: primer KVM165
SEQ ID No. 17: probe TM1242
SEQ ID No. 18: primer PRIM1041
SEQ ID No. 19: primer PRIM1040
SEQ ID No. 20: probe TM1789
SEQ ID No. 21: primer PRIM1629
SEQ ID No. 22: probe TM2083
SEQ ID No. 23: soybean event EE-GM5
SEQ ID No. 24: EE-GM5 5' junction sequence
SEQ ID No. 25: EE-GM5 3' junction sequence
SEQ ID No. 26: primer GLPA210
SEQ ID No. 27: primer GLPA212
SEQ ID No. 28: primer GLPB167
SEQ ID No. 29: primer GLPB170
SEQ ID No. 30: primer PRIM2123
SEQ ID No. 31: primer PRIM2122
SEQ ID No. 32: probe TM2327
SEQ ID No. 33: pre-insertion locus sequence

EXAMPLES

1. Transformation of *Glycine max* with a Nematode Resistance and an Herbicide Tolerance Gene 1.1. Description of the Inserted T-DNA Comprising the cry14Ab-1.b and hppdPf-4 Pa Chimeric Genes EE-GM5 soybean was developed through *Agrobacterium*-mediated transformation using the vector pSZ8832 containing hppdPf-4 Pa and cry14Ab-1.b expression cassettes:

(i) The mutant hppdPf-4 Pa gene that encodes for the HPPD-4 protein (the amino acid sequence of which is shown in SEQ ID No. 10). The hppdPf-4 Pa coding sequence was developed by introducing point mutations at position 335 (substitution of Glu by Pro), at position 336 (substitution of Gly by Trp), at position 339 (substitution of Lys by Ala) and at position 340 (substitution of Ala by Gln) in a DNA encoding the HPPD protein derived from *Pseudomonas fluorescens* strain A32. Expression of the HPPD-4 protein confers tolerance to HPPD inhibitor herbicides, such as isoxaflutole, topramezone or mesotrione.

(ii) The cry14Ab-1.b gene encodes for the Cry14Ab-1 protein (the amino acid sequence of which is shown in SEQ ID No. 8). Expression of the Cry14Ab-1 protein confers resistance to nematodes such as the soybean cyst nematode *Heterodera glycines*.

Plasmid pSZ8832 is a plant transformation vector which contains a chimeric cry14Ab-1.b gene and a chimeric hppdPf-4 Pa gene located between the right T-DNA border (RB) and the left T-DNA border (LB). A description of the genetic elements comprised in the T-DNA between the right and the left T-DNA border is given in Table 1 below. Confirmatory sequencing of the T-DNA (between the T-DNA borders) of this plasmid resulted in the sequence of SEQ ID No. 11. The nucleotide sequence of the cry14Ab-1.b and hppdPf-4 Pa coding sequences (showing the coding strand) is represented in SEQ ID No. 7 and 9, respectively.

TABLE 1

Description of the genetic elements between the T-DNA borders in pSZ8832, and nucleotide positions in SEQ ID No. 11.

| Position in SEQ ID No. 11 | Orientation | Description |
|---|---|---|
| 1-130 | | Polylinker sequence: sequence used in cloning |
| 131-400 | Counter clockwise | sequence including the 3' untranslated region of the 35S transcript of the Cauliflower Mosaic Virus (Sanfaçon et al., 1991, Genes & development, 5(1), 141-149) |
| 401-411 | | Polylinker sequence: sequence used in cloning |
| 412-3969 | Counter clockwise | cry14Ab-1.b: coding sequence of the delta-endotoxin gene of *Bacillus thuringiensis* |
| 3970-5276 | Counter clockwise | Pubi10At: sequence including the promoter region of ubiquitin-10 gene of *Arabidopsis thaliana* (Grefen et al., 2010, The Plant journal, 64(2), 355-365) |
| 5277-5381 | | Polylinker sequence: sequence used in cloning |
| 5382-5576 | Counter clockwise | sequence including the 3' untranslated region of the 35S transcript of the Cauliflower Mosaic Virus (Sanfaçon et al., 1991, Genes & development, 5(1), 141-149) |
| 5577-5588 | | Polylinker sequence: sequence used in cloning |
| 5589-6665 | Counter clockwise | hppdPf-4Pa: sequence encoding a variant 4-hydroxyphenylpyruvate dioxygenase derived from *Pseudomonas fluorescens* |
| 6666-7037 | Counter clockwise | TPotpY-1Pf: coding sequence of an optimized transit peptide derivative (position 55 changed into Tyr), containing sequence of the RuBisCO small subunit genes of *Zea mays* and *Helianthus annuus* (U.S. Pat. No. 5,510,471) |
| 7038-7058 | | Polylinker sequence: sequence used in cloning |
| 7059-7185 | Counter clockwise | sequence including the leader sequence of the Tobacco Etch Virus genomic RNA (Allison et al., 1985, Virology, 147(2), 309-316) |
| 7186-7191 | | Polylinker sequence: sequence used in cloning |
| 7192-7941 | Counter clockwise | sequence including the double enhanced promoter region of the Cauliflower Mosaic Virus 35S genome transcript (Kay et al., 1987, Science, 236(4806), 1299-1302) |
| 7942-8068 | | Polylinker sequence: sequence used in cloning |

1.2. Event EE-GM5

The T-DNA vector pSZ8832 was introduced into *Agrobacterium tumefaciens* and transformed soybean plants (var. Thorne) were selected using HPPD inhibitor tolerance according to methods known in the art. The surviving plants were then self-pollinated to generate T1 seed. Subsequent generations were produced through self-pollination, or through crossing into other soybean germplasm.

1.2.1 Identification of Elite Event EE-GM5

Elite event EE-GM5 was selected based on an extensive selection procedure (based on parameters including but not limited to trait efficacy in the greenhouse and the field, molecular characteristics, and agronomic characteristics) from a wide range of different transformation events obtained using the same chimeric genes. Soybean plants containing EE-GM5 were found to have an insertion of the transgenes at a single locus in the soybean plant genome, to have overall agronomy similar to the parent plants used for transformation, to cause no yield penalty by the insertion of the transforming DNA (as compared to a corresponding isogenic line without the event, such as a "null" plant line obtained from a transformed plant in which the transgenes segregated out), to result in a significant reduction of adult females infesting the roots in a standard SCN greenhouse assay, and to have improved yield under SCN nematode pressure in the field compared to the isogenic null line not containing EE-GM5. Additionally, tolerance to HPPD inhibitor herbicide application was measured in field trials, but herbicide tolerance was not a selection criterion for elite event selection.

1.2.1.1 Molecular Analysis of the Event

Southern blot results showed that EE-GM5 contains a single transgenic locus which contains a single copy of the cry14Ab-1.b chimeric gene and a single copy of the hppdPf-4 Pa chimeric gene. EE-GM5 is missing a part of the 35S promoter of the hppdPf-4 Pa chimeric gene (indicating that not the entire T-DNA of SEQ ID No. 11 was inserted in the soybean genome during transformation). No PCR fragments were obtained upon PCR analysis using primers targeting vector backbone sequences that are flanking the left and right border of the T-DNA as well as the aadA sequence. Also, the presence of identical EE-GM5 integration fragments in multiple generations of EE-GM5 demonstrates the structural stability of the event.

1.2.1.2 Inheritance of the Event

Inheritance of the inserted T-DNA insert in subsequent generations by testing the genotype of hppdPf-4 Pa and cry14Ab-1.b genes by PCR analysis shows that the hppdPf-4 Pa and cry14Ab-1.b genes contained within the EE-GM5 insert are inherited in a predictable manner and as expected for a single insertion. These data are consistent with Mendelian principles and support the conclusion that the EE-GM5 event consists of a single insert integrated into a single chromosomal locus within the soybean nuclear genome.

Also, analysis of the segregation patterns of EE-GM5 in subsequent generations upon introgression of EE-GM5 into 5 elite soybean lines confirmed normal Mendelian segregation. Table 2 shows the observed segregation of EE-GM5 in different segregating populations.

TABLE 2

Segregation analysis EE-GM5

| Parent | Generation | Observed | | | | Statistics | | |
|---|---|---|---|---|---|---|---|---|
| | | HH | Hemi | null | Total | Chi-Square | P value | sign |
| Parent 1 | BC2F2 | 481 | 903 | 497 | 1881 | 3.26 | 0.20 | ns |
| Parent 1 | BC3F2 | 108 | 200 | 102 | 410 | 0.42 | 0.81 | ns |
| Parent 2 | BC2F2 | 45 | 101 | 50 | 196 | 0.44 | 0.80 | ns |
| Parent 2 | BC3F2 | 16 | 37 | 25 | 78 | 2.28 | 0.32 | ns |
| Parent 3 | BC2F2 | 57 | 127 | 57 | 241 | 0.70 | 0.70 | ns |
| Parent 3 | BC3F2 | 12 | 39 | 27 | 78 | 5.77 | 0.06 | ns |
| Parent 4 | F2 | 174 | 397 | 197 | 768 | 2.26 | 0.32 | ns |
| Parent 5 | BC2F2 | 72 | 132 | 89 | 293 | 4.84 | 0.09 | ns |

In Table 2, "HH" stands for homozogous plants, "Hemi" for hemizygous plants, and "null" for null-segregants having lost EE-GM5, and "ns" means not statistically significant (as to any variation from normal/expected segregation). In these trials, Parent 1 was a MG VI line with Rhg1 and Rhg4 native SCN resistance, Parent 2 was a MG VI line susceptible to SCN, Parent 3 was a MG IX line susceptible to SCN, Parent 4 was a MG III line with Rhg1 native SCN resistance, and Parent 5 was a MG I line susceptible to SCN.

1.2.1.3 Stability of Protein Expression

Protein expression levels of HPPD-4 and Cry14Ab-1 proteins in greenhouse-grown plants were determined by sandwich enzyme-linked immunosorbent assay (ELISA) in leaf, root and seed samples collected from different generations (e.g., T4, T6 and BC2F3) of EE-GM5 soybean. HPPD-4 and Cry14Ab-1 exhibit similar mean expression levels in leaf, root and seed across all generations tested. Any differences observed in Cry14Ab-1 and HPPD-4 concentrations were attributed to natural plant-to-plant variability.

1.2.1.4 Agronomic Performance and Tolerance to HPPD Inhibitor Herbicides

In agronomic equivalency trials, plants comprising EE-GM5 in the original transformation background (Thorne) were compared to segregating nulls (lacking EE-GM5) and to wild-type Thorne plants when grown in the absence of SCN. Plots were not treated with HPPD herbicides but were maintained as weed free through the use of conventional herbicides and hand weeding where necessary. No differences impacting agronomic performance in a biologically significant way were observed between the plants containing the event and the segregating nulls (lacking EE-GM5) when grown in comparable trials at different locations when checking for qualitative plant characteristics such as flower color, pod color, seed color and pubescence and for quantitative characteristics like yield, height, lodging, stand, and days to maturity. Hence, plants comprising EE-GM5 showed normal agronomic characteristics comparable to the corresponding non-transgenic plants.

Additional trials with EE-GM5 in the original Thorne transformation background were conducted in 2017. Preliminary trials wherein EE-GM5 was in elite MG1 and MG3 genetic backgrounds were also established at a limited number of locations in 2017. When checking for qualitative plant characteristics such as flower color, pod color, seed color and pubescence and for quantitative characteristics like yield, height, lodging, stand, test weight, and days to maturity, no consistent and meaningful differences between the EE-GM5 event and the segregating nulls (lacking EE-GM5) were detected in any of the three genetic backgrounds, confirming that plants comprising EE-GM5 showed normal agronomic characteristics.

Tolerance of plants comprising EE-GM5 to HPPD inhibitor herbicides was tested at different locations in the field over 2 years. In these trials, it was found that plants with EE-GM5 had commercially relevant tolerance to isoxaflutole (IFT) when applied pre-emergence as well as when applied post-emergence, but crop damage was a bit higher for the IFT pre-emergence application. These trials also showed that plants containing event EE-GM5 had commercially relevant tolerance to mesotrione (MST) when applied pre-emergence or when applied post-emergence. All post-emergence treatments were at the V2-V3 stage, with adjuvants crop oil concentrate and ammonium sulfate added to increase herbicide activity.

Figure 5:
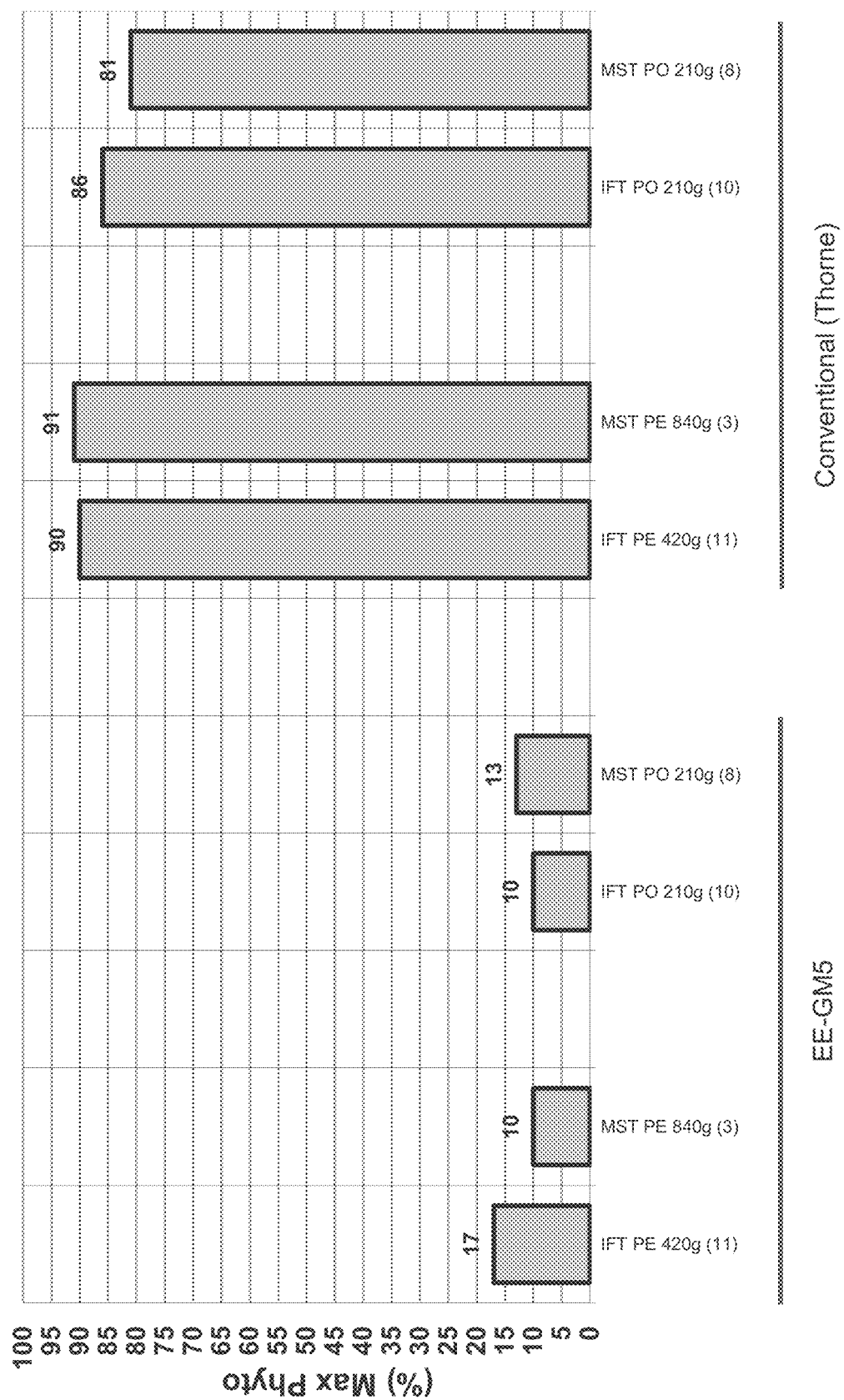
FIG. 5: Average max phyto results for herbicide treatments

FIG. 5 shows the average of the maximum phytotoxicity data (plant damage) recorded for herbicide treatment in several field trials across 2 years, for soybean plants containing event EE-GM5 as compared to untransformed/conventional soybean plants. Control untransformed Thorne plants showed average maximum phytotoxicity values of about 80 to 90% in these same trials, showing these HPPD inhibitor herbicides are not tolerated by (non-GM) soybean. The "maximum phytotoxicity" as used herein is the highest phytotoxicity rating recorded at any observation during the duration of a trial (with 3 to 4 observations per trial). In existing weed control applications, a normal (1×) dose for isoxaflutole (IFT) in pre- or post-emergence application and for MST in post-emergence application is 105 gr/ha, and a normal (1×) dose for mesotrione in pre-emergence application is 210 gr/ha. Hence, in these trials reported in FIG. 5, the applications used in pre-emergence in FIG. 5 (420 gr/ha for IFT, 840 gr/ha for mesotrione) were at 4 times the normal dose, and in post-emergence (210 gr/ha for each of IFT and mesotrione) were at 2 times the normal dose.

In a $3^{rd}$ year, plants with EE-GM5 (in Thorne background) when treated with isoxaflutole (IFT, at 410 g/ha) pre-emergence at one field trial location, had 9% maximum phytotoxicity, and when treated with isoxaflutole (IFT) post-emergence (V2-V3 stage, at 210 h/ha) at 4 locations, had an average of 10.9% maximum phytotoxicity, confirming the tolerance observed before.

Also, in several field trials across 2 years, soybean plants with event EE-GM5 had good tolerance towards experimental HPPD inhibitor compound 2-methyl-N-(5-methyl-1,3,4-oxadiazol-2-yl)-3-(methylsulfonyl)-4-(trifluoromethyl)benzamide (U.S. Pat. No. 9,101,141) when applied pre-emergence at 400 gr ai/ha or post-emergence at 200 gr ai/ha, respectively (the average maximum phytotoxicity value for each treatment was below 20%). In these trials, soybean plants with event EE-GM5 also showed good tolerance (average maximum phytotoxicity of 20%) to experimental HPPD inhibitor compound 2-chloro-3-(methylsulfanyl)-N-(1-methyl-1H-tetrazol-5-yl)-4-(trifluoromethyl)benzamide (U.S. Pat. No. 8,481,749) when applied post-emergence at 100-150 gr ai/ha. All post-emergence treatments were at the V2-V3 stage, with adjuvants crop oil concentrate and ammonium sulfate added to increase herbicide activity. In a $3^{rd}$ year, plants with EE-GM5 (in Thorne background) when treated with 2-chloro-3-(methylsulfanyl)-N-(1-methyl-1H-tetrazol-5-yl)-4-(trifluoromethyl)benzamide at 150 g/ha post-emergence at 3 field trial locations, had an average maximum phytotoxicity of 13.3%.

The same or very similar average maximum phytotoxicity ratings as those described in FIG. 5 were obtained for IFT when adding the data obtained from a 3rd season of herbicide tolerance field trials, applying isoxaflutole herbicide at the same dosages in pre or post to EE-GM5 but at another geographic location.

Also, plants with EE-GM5 when treated post-emergent (V2-V3) with topramezone at 36 g ai/ha (+COC and AMS) in 2 field trials in the US gave an average maximum phytotoxicity of 11%, showing EE-GM5 also confers good tolerance to this HPPD inhibitor.

1.2.1.5 Nematode Resistance

Standard SCN assays measuring female index in the greenhouse showed a significant reduction of SCN cysts on roots of plants containing EE-GM5 when compared to Thorne wild-type soybean plants. In addition, standard SCN assays measuring female index in the greenhouse also showed that soybean plants containing event EE-GM5 and native SCN resistance showed a significant reduction of SCN cysts on roots compared to SCN resistant elite soybean lines without EE-GM5. When EE-GM5 was introgressed into an elite soybean line with PI 88788 soybean resistance (maturity group 3), or into an elite soybean line with Peking soybean resistance (maturity group 6.2), consistently a reduced number of SCN cysts was seen on the roots compared to roots with native resistance alone.

Figure 6:
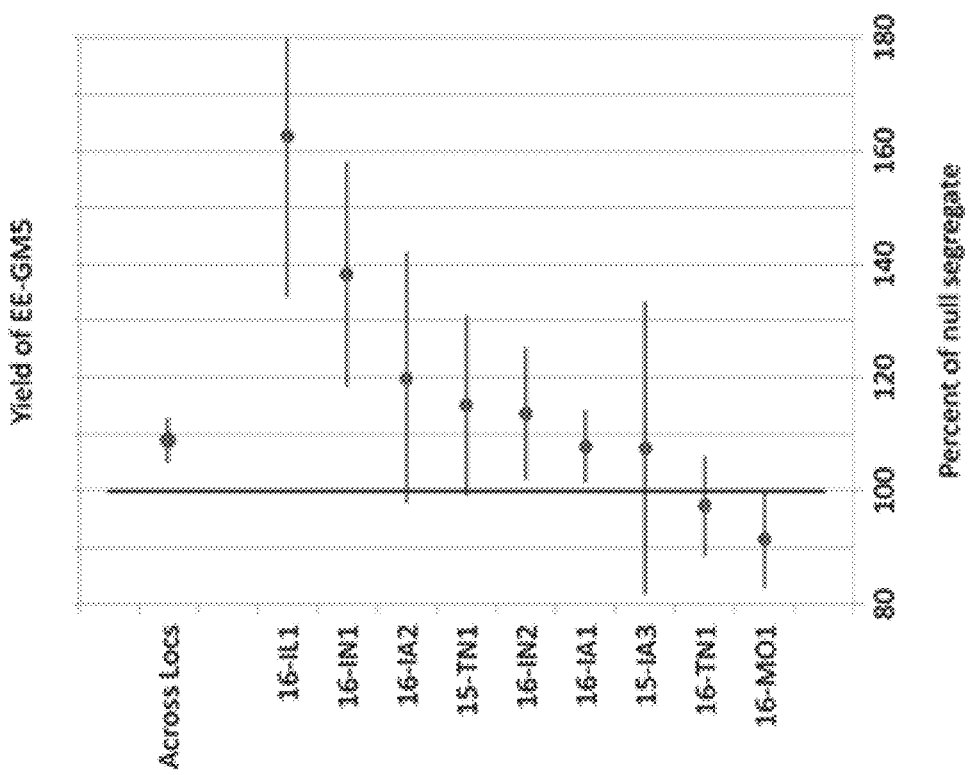
FIG. 6. Grain yield of EE-GM5 in Thorne in SCN infested fields.

In field trials across 2 years at several locations, soybean plants containing EE-GM5 gave a significant yield increase compared to the isogenic null segregants in SCN-infested fields. FIG. 6 shows the grain yield of EE-GM5 in the original transformant background (Thorne) as tested in 9 different locations throughout Iowa, Illinois, Indiana, Missouri and Tennessee in 2015 and 2016, in SCN infested fields (ranging from low to high SCN infestation). Additional trials with EE-GM5 in the original transformant background (Thorne) were conducted in 2017 at a total of 12 locations with varying SCN pressure. Across all these 12 trials, plants containing EE-GM5 produced an average of 10% higher yields than the null segregants lacking EE-GM5 (p=0.003). FIG. 7 shows the grain yield of EE-GM5 when introgressed (BC2F3) into an elite MG I (maturity group I) line that is susceptible to SCN and was tested at one location in Minnesota and one location in North Dakota in 2016 (each with high SCN infestation level). The same MG I line was tested at the same two locations (each again with high SCN infestation) and at an additional site in Wisconsin in 2017 (the latter having moderate SCN pressure), and grain yield of plants containing EE-GM5 was consistently higher than the corresponding null segregants lacking EE-GM5. Finally, preliminary studies across three locations with moderate to high SCN pressure in Brazil in late planted trials in 2017 showed a significant average increase of 31% (p=0.01) in an elite susceptible line for plants with EE-GM5 when compared to the segregating null (lacking EE-GM5). Due to the late planting date, overall yields in these preliminary Brazil trials tended to be low and the variability within one trial was rather high, which may have influenced the magnitude of the yield increase, but a clearly significant and visually observable yield increase was found for plants with EE-GM5. Hence, event EE-GM5 confers a significant yield increase on soybean plants in SCN-infested fields.

In a study to evaluate the effect of event EE-GM5 on yield when combined with native SCN resistance, a series of F3 populations were developed from the single cross of EE-GM5 with an elite MG III conventional line carrying the rhg1 resistance gene from PI 88788. In the F3 populations one 'stacked' population that is homozygous for both event EE-GM5 and the rhg1 allele, was compared to a population homozygous for just the rhg1 allele (lacking EE-GM5). Yield trials were established with these populations in 2016 at three locations with moderate to high infestation of SCN and in 2017 at seven locations ranging from low to high SCN pressure. The results are shown in FIG. 8. All the 2017 trials included three different seed treatments. No significant yield differences or interactions were observed for any of these seed treatments alone, so data was pooled across seed treatments to provide the best statistical estimates of the yield difference between the homozygous (HH) event and the null segregant. As shown in FIG. 8, across all three locations in 2016, the 'stacked' population (plants homozygous for the EE-GM5 event and the rhg1 allele) produced 8% greater yields than the population carrying only the rhg1 allele (p=0.08), and the 2017 trials provided an 11% average yield increase for plants homozygous for the EE-GM5 event and the rhg1 allele (p=1.24-11), compared to the population carrying only the rhg1 allele. For reference, the average yield increase for lines containing EE-GM5 across the 2017 trials with only the base seed treatment (Evergol® Energy+Allegiance® fungicide+Poncho® insecticide) was 0.27 T/ha (10.2% yield increase; p=0.0002). The base seed treatment used in all the 2016 trials was Evergol® Energy+Allegiance® fungicide. As shown in FIG. 8, a close relationship was found across all 10 trials in both years between yield response and SCN pressure with greater yield gains being observed at sites with high SCN pressure (towards the top in FIG. 8). These results show that adding the EE-GM5 event to soybean varieties with conventional SCN resistance can provide a significant yield increase in fields infested by SCN.

Conducting yield trials under moderate to high SCN infestation are challenging due many factors that have an impact on the results. SCN population densities within fields can vary substantially and so the overall impact of SCN on yield can also vary from one plot to the next (see, e.g., www.plantmanagementnetwork.org/pub/php/review/2009/sce08/). Favorable soil types, good fertility and adequate rainfall can mitigate the impact of SCN infestation on the soybean plant and can minimize yield impacts even under high SCN populations. Many fields with very high SCN populations tend to have poor soils and thus lower yield potential, making it difficult to discern statistically significant impacts on yield. Thus, yield data from SCN field trials can be quite variable and one would not expect to see significant improvements in yield in every trial with high SCN populations. The overall trends across trials are the most relevant criteria for judging performance of an event.

SCN field trials that were done with plants containing EE-GM5 were established in field with natural SCN infestation. Experimental units consisted of a field plot containing 2 to 4 rows spaced 0.76 m apart and ranging from 3.8 to 9.1 m long. The number of rows per plot and plot length varied from location to location based on field size and equipment configurations. Plots were seeded at 26 seeds per meter and so each experimental unit contained between 200 and 960 seeds. Plots were randomized in the field using a split-plot or split-split plot design. Split plot designs are well suited to help minimize the effect of high variability in soil type or SCN populations which is common in SCN infested fields. In SCN field trials plants comprising EE-GM5 were planted in a sub plot next to, or very close to, a companion sub plot containing segregating null plants (without EE-GM5). The close proximity of the two plots helps minimize the effect of (SCN) field variability on the estimate of the difference between the plants with and without event EE-GM5. Most trials were replicated four times, but a few were replicated three times and a few were replicated five or six times.

Moderate to severe infestations of Sudden Death Syndrome were observed at two locations (Indiana and Iowa) in 2016. Plots at these two locations were rated for incidence and severity of SDS symptoms and the SDS Disease Index (DX) was calculated using the "SIUC Method of SDS Scoring" (www.scnresearch.info/462.pdf). DX ratings on plants homozygous for EE-GM5 were 61% lower in Indiana and 55% lower in Iowa than on the susceptible null segregate (lacking EE-GM5), indicating that the event was providing protection against SDS infection. SDS and SCN are often closely associated in the field and will show some interactions in the plant (see, e.g., www.soybeanresearchinfo.com/pdf docs/sdsupdate.pdf, and www.apsnet.org/edcenter/intropp/lessons/fungi/ascomycetes/pages/suddendeath-.aspx).

In 2017, Iron Deficiency Chlorosis (IDC) scores were gathered on plants with EE-GM5 (and their null segregants) at one trial location in the US (with high SCN infestation) where IDC symptoms were observed. The trial was a split-plot design looking at the effect of event in three different backgrounds. IDC ratings were taken as described by Cianzio et al. (1979) Crop Science 19: 644-646. FIG. 11 shows the averages of IDC scores for plants with event EE-GM5 and those for the corresponding null segregants (lacking EE-GM5) across three genetic backgrounds (1 SCN-resistant (PI 88788 resistance), 1 SCN-susceptible, and the SCN-susceptible Thorne background). Significantly lower IDC scores were found for plants containing EE-GM5 compared to their null segregants. Hence, EE-GM5 significantly reduced the foliar severity of IDC in a field trial where soybean plants were challenged by both SCN and IDC. This reduction occurred across three soybean lines, one of which included PI 88788-type native SCN resistance.

Also, non-transformed Thorne and EE-GM5 seeds were geminated and planted in the greenhouse to check for control of the lesion nematode, *Pratylenchus brachyurus*. *Pratylenchus brachyurus* nematodes (#1500/plant, different developmental stages) were applied to the plants when 2 weeks old. 30 days after application, *Pratylenchus* nematodes were extracted from the roots and counted. The average number of nematodes found in the roots of plants containing EE-GM5 were compared with the average number of *Pratylenchus* nematodes found in the wild-type Thorne plant roots. On average about 80 to 90% fewer *Pratylenchus* nematodes were found in roots of plants containing EE-GM5 when compared with the Thorne control roots, indicating significant control of lesion nematodes by soybean event EE-GM5.

FIG. 9 show results from a *Pratylenchus brachyurus* greenhouse assay in the US, comparing elite lines with EE-GM5 in 5 elite soybean lines (one SCN susceptible (MG 1), one SCN resistant (PI 88788, MG 3), one SCN susceptible (MG 6.2), one SCN resistant (Peking, MG 6.2), and one SCN susceptible (MG 9)) to SCN-susceptible and SCN-resistant US soybean lines. The soybean plants were grown in small cone pots and kept in greenhouses with temperature varying between 25-32° C. *Pratylenchus brachyurus* nematodes, obtained from South Carolina and increased in the greenhouse were used to inoculate plants in the V2-V3 development stage. Approximately 1500 eggs+adults were inoculated per plant and each entry had 5 plants. 30 days after infestation, nematodes and eggs were extracted from the roots and counted. Each entry was run in two independent experiments. While SCN-susceptible and SCN-resistant US soybean lines did not show control of *Pratylenchus*, plants with EE-GM5 showed about 90% control of *Pratylenchus*.

FIG. 10 shows results from a *Pratylenchus brachyurus* greenhouse assay in Brazil, comparing soybean plants with EE-GM5 to Brazil soybean lines with no resistance and 1 low Rf line, and SCN-susceptible and—resistant plants. The soybean lines were grown in small cone pots and kept in greenhouses with temperature varying between 25-32° C. *Pratylenchus brachyurus* nematodes, obtained from Brazil fields and increased in the greenhouse were used to inoculate plants in the V2-V3 development stage. Approximately 1000 eggs+adults were inoculated per plant and each entry had 5 plants. 30 days after infestation, nematodes and eggs were extracted from the roots and counted. Results shown are from a single experiment. One Brazilian soybean line (BRS 7380), labeled as having a low reproductive factor for *Pratylenchus* showed about 89% reduction of *Pratylenchus*. Plants with EE-GM5 gave ~99% control of *Pratylenchus*. Soybean lines that carry native resistance to SCN (rhg1+rhg4) do not control *Pratylenchus brachyurus*.

Also, plants containing EE-GM5 can be used to control root-knot nematodes (RKN) such as *Meloidogyne incognita*. Even though the population of *Meloidogyne incognita* does not infest Thorne wild-type soybean very well, Thorne plants with EE-GM5 show a further reduction in the number of RKN eggs/root mass on average, as compared to untransformed Thorne plants.

1.2.2 Identification of the Flanking Regions and Inserted T-DNA of Elite Event EE-GM5

The sequence of the regions flanking the inserted T-DNA and the T-DNA contiguous therewith as contained in the EE-GM5 elite event are shown in the enclosed Sequence Listing.

1.2.2.1 5' T-DNA Flanking Region

A fragment identified as comprising the 5' T-DNA flanking region of EE-GM5 was sequenced and its nucleotide sequence is represented in SEQ ID No. 5, nucleotides 1-166. This 5' T-DNA flanking region is made up of soybean genomic sequences corresponding to the pre-insertion locus sequence (SEQ ID No. 5, nucleotides 1-166). The 5' junction region comprising part of the inserted T-DNA sequence and part of the T-DNA 5' flanking sequence contiguous therewith is represented in SEQ ID No. 1 and 3.

1.2.2.2 3' T-DNA Flanking Region

A fragment identified as comprising the 3' T-DNA flanking region of EE-GM5 was sequenced and its nucleotide sequence is represented in SEQ ID No. 6, nucleotides 359-691. This 3' T-DNA flanking region is made up of a 39 nucleotide filler DNA sequence (from position 359 to position 397 in SEQ ID No. 6), followed by soybean genomic sequences corresponding to the pre-insertion locus sequence (from position 398 to position 691 in SEQ ID No. 6). The 3' junction region comprising part of the inserted T-DNA sequence and part of the T-DNA 3' flanking sequence contiguous therewith is represented in SEQ ID No. 2 and 4.

1.2.2.3 Inserted T-DNA of EE-GM5

The inserted T-DNA contiguous with the above 5' T-DNA flanking sequence was sequenced and its nucleotide sequence is represented in SEQ ID No. 5, nucleotides 167-353. Also, the inserted T-DNA contiguous with the above 3' T-DNA flanking sequence was sequenced and its nucleotide sequence is represented in SEQ ID No. 6, nucleotides 1-358. During transformation, 63 bp of genomic DNA were deleted at the pre-insertion locus sequence, and these were replaced by the inserted DNA (made up of T-DNA and a small part of filler DNA).

Sequencing of the T-DNA region in transformation plasmid pSZ8832 (the part between the T-DNA borders) resulted in the sequence reported in SEQ ID No. 11. The chimeric cry14Ab-1.b gene sequence (comprising the Ubi10 promoter and the 35S 3' untranslated region) is represented in SEQ ID No. 11 from nucleotides 131-5276 (counterclockwise). The inserted T-DNA sequence at the 5' flanking region in SEQ ID No. 5 (nucleotide 167-353) is identical to the nucleotide sequence in SEQ ID No. 11 from nucleotide 1 to nucleotide 187, and the inserted T-DNA sequence at the 3' flanking region in SEQ ID No. 6 (nucleotide 1-358) is identical to the nucleotide sequence in SEQ ID No. 11 from nucleotide 7102 to nucleotide 7459. Hence, the 5' end of the T-DNA inserted in EE-GM5 corresponds to nucleotide 1 in the transformation plasmid sequence of SEQ ID No. 11 and the 3' end of the T-DNA inserted in EE-GM5 corresponds to nucleotide 7459 in the transformation plasmid sequence of SEQ ID No. 11. The T-DNA inserted in EE-GM5 between the sequence of SEQ ID No. 5 and the sequence of SEQ ID No. 6 is contained in the seed deposited at the ATCC under accession number PTA-123625, and has a sequence essentially similar or identical to the sequence of SEQ ID No. 11 from nucleotide 188 to nucleotide 7101.

The insertion locus for event EE-GM5 can be determined from wild-type soybean var. Thorne based on the 5' and 3' T-DNA flanking sequences provided herein (SEQ ID No. 5 from nt 1 to nt 166 and SEQ ID No. 6 from nt 359 to nt 691) by methods known in the art. The pre-insertion locus sequence in the soybean genome corresponds to the following sequences in order: nucleotide position 1 to nucleotide position 166 in SEQ ID No. 5, a 63 nt deletion, and nucleotide position 398 to nucleotide position 691 in SEQ ID No. 6. The complete pre-insertion locus sequence is given in SEQ ID No. 33, wherein nt 1-1000 are 5' flanking genomic sequences, nt 1001-1063 are the target site deletion, and 1064-2063 are 3' flanking genomic sequences.

1.2.3 Confirmation of the Flanking Regions and Inserted T-DNA of Elite Event EE-GM5

PCR amplification using primers targeted to the plant DNA upstream and downstream of the inserted T-DNA and to the inserted T-DNA in EE-GM5 confirmed and extended the 5' and 3' flanking sequences of EE-GM5.

1.2.3.1. 5' Junction Sequence EE-GM5-Specific Reaction

Two primers, GLPA210 and GLPB167, were designed to amplify an amplicon of approximately 5118 bp spanning the junction region of the 5' T-DNA flanking sequence with the T-DNA insertion fragment for event EE-GM5. The sequence of primer GLPA210 originates from the soybean reference sequence of *Glycine max* Williams 82.a2.v1.

Forward primer targeted to the EE-GM5 T-DNA 5' flanking sequence:

```
GLPA210
                                        (SEQ ID No. 26)
5'-CTCTCACCCAgATTTCAC-3'
```

Reverse primer targeted to the EE-GM5 inserted T-DNA sequence:
```
GLPB167
                                        (SEQ ID No. 28)
5'-TACAACgTgCTCgCTATTCC-3'
```

Composition of the reaction mixture for the 5' junction sequence reaction:

| | | |
|---|---|---|
| 5 | μl | Expand ™ Buffer (Roche) |
| 1 | μl | dNTPs (10 mM) |
| 2 | μl | forward primer (10 pmol/μl) |
| 2 | μl | reverse primer (10 pmol/μl) |
| 0.75 | μl | Expand ™ High Fidelity enzyme mix (3.5 U/μL; Roche) |
| 50 | ng | template DNA |
| Water up to 50 μl | | |

Thermocycling conditions for the 5' junction sequence reaction:

| | Time | | Temperature |
|---|---|---|---|
| Followed by: | 4 | min. | 94° C. |
| | 1 | min. | 94° C. |
| | 1 | min. | 55° C. |
| | 4 | min. | 68° C. |
| | For 5 cycles | | |
| Followed by: | 15 | sec. | 94° C. |
| | 45 | sec. | 60° C. |
| | 4 | min. + 5 sec/cycli | 68° C. |
| | For 25 cycles | | |
| Followed by: | 10 | min. | 68° C. |
| Followed by: | 10 | min. | 4° C. |
| | Forever | | 10° C. |

The sequence of the extended T-DNA 5' flanking sequence that was obtained and that is contiguous with and upstream of part of the inserted T-DNA as shown in SEQ ID No. 5 is shown in SEQ ID No. 24.

1.2.3.2. 3' Junction Sequence EE-GM5-Specific Reaction

Two primers, GLPB170 and GLPA212, were designed to amplify an amplicon of approximately 4982 bp spanning the junction region of the T-DNA insertion fragment for event EE-GM5 with the 3' T-DNA flanking sequence. The sequence of primer GLPA212 originates from the reference sequence of *Glycine max* Williams 82.a2.v1.

Forward primer targeted to the EE-GM5 inserted T-DNA sequence:

```
GLPB170
                                        (SEQ ID No. 29)
5'-TCTCggTATCAgCgTTCTTg-3'

Reverse primer targeted to the EE-GM5 T-DNA
3' flanking sequence:
GLPA212
                                        (SEQ ID No. 27)
5'-CCCATgCggTATTATgTg-3'
```

Composition of the reaction mixture for the 3' junction sequence reaction:

| | | |
|---|---|---|
| 5 | μl | Expand ™ Buffer (Roche) |
| 1 | μl | dNTPs (10 mM) |
| 2 | μl | forward primer (10 pmol/μl) |
| 2 | μl | reverse primer (10 pmol/μl) |
| 0.75 | μl | Expand ™ High Fidelity enzyme mix (3.5 U/μL; Roche) |
| 50 | ng | template DNA |
| Water up to 50 μl | | |

Thermocycling conditions for the 3' junction sequence reaction:

|  | Time |  | Temperature |
|---|---|---|---|
| Followed by: | 4 | min. | 94° C. |
|  | 1 | min. | 94° C. |
|  | 1 | min. | 54.3° C. |
|  | 4 | min. | 68° C. |
|  | For 5 cycles |  |  |
| Followed by: | 15 | sec. | 94° C. |
|  | 45 | sec. | 60° C. |
|  | 4 | min. + 5 sec/cycle | 68° C. |
|  | For 25 cycles |  |  |
| Followed by: | 10 | min. | 68° C. |
| Followed by: | 10 | min. | 4° C. |
|  | Forever |  | 10° C. |

The sequence of the extended T-DNA 3' flanking sequence that was obtained and is contiguous with and downstream of part of the inserted T-DNA as shown in SEQ ID No. 6 is shown in SEQ ID No. 25.

Since the resulting amplicons in the above 2 reactions overlapped, this allowed a reconstruction of the sequence of the EE-GM5 inserted T-DNA and the extended 5' and 3' flanking sequences, which is shown in SEQ ID No. 23. The 5' T-DNA flanking sequence in SEQ ID No. 23 is from nucleotide position 1 to nucleotide position 1113 (corresponding to pre-insertion locus genomic sequences), the inserted T-DNA sequence is from nucleotide position 1114 to nucleotide position 8572 and the 3' T-DNA flanking sequence in SEQ ID No. 23 is from nucleotide position 8573 to nucleotide position 9663 (corresponding to 39 nt filler DNA (nt 8573-8611 in SEQ ID No. 23) and pre-insertion locus genomic sequences (nt 8612-9663 in SEQ ID No. 23)).

2. Development of Identification Protocols for EE-GM5

2.1. End-Point Method for EE-GM5 Identity Analysis

This method describes a polymerase chain reaction detection method to analyze the presence of event EE-GM5-specific DNA sequences in DNA samples obtained from biological samples, such as plant materials (e.g., leaf or seed) using standard DNA extraction procedures.

The method description outlines the method design, including the oligonucleotide primer and probe sequences, the composition of the reaction mixture, the thermocycling conditions required to perform the reaction, and the fluorescent reader settings found appropriate for amplicon detection. It also provides general recommendations on the nature and use of control samples. In addition, guidance is provided for data analysis and interpretation, including an example of a method result taking into account the recommendations on the use of control materials and the guidance for data analysis.

2.1.1. Method Design

The method uses the Taqman chemistry to amplify and detect two target sequences: a EE-GM5 specific reaction determines the presence of the event, a taxon-specific reaction validates negative results for the event-specific reaction.

2.1.1.1. EE-GM5-Specific Reaction

Two primers, PRIM1038 and PRIM1039, were designed to amplify an amplicon of 85 bp spanning the junction region of the 3' flanking sequence with the T-DNA insertion fragment for event EE-GM5.

A probe, TM1788 using FAM as fluorescent label and BHQ1 as quencher was designed to detected the amplified sequence.

```
Forward primer targeted to the EE-GM5 T-DNA
sequence:
PRIM1038
                                   (SEQ ID No. 12)
5'-gAgCCACCTTCCTTTTCCACTA-3'

Reverse primer targeted to the EE-GM5 T-DNA
3' flanking sequence:
PRIM1039
                                   (SEQ ID No. 13)
5'-ATAgggTTACTgCTTCgTAAAATAAgCA-3'
```

Probe targeted to the junction of the EE-GM5 T-DNA and its' 3' flanking sequence:
TM1788 FAM 5'-CgCgTCCATgATgCTgCgACTATg-3' BHQ1 (SEQ ID No. 14)

2.1.1.2. Taxon-Specific Specific Reaction

Two primers, KVM164 and KVM165, were designed to amplify an amplicon of 102 bp of the soybean endogenous lectin1 gene sequence.

A probe, TM1242 using JOE as fluorescent label and BHQ1 as was designed to detected the amplified sequence

```
Forward primer targeted to the endogenous Lectin
1 gene sequence:
KVM164
                                   (SEQ ID No. 15)
5'-CTTTCTCgCACCAATTgACA-3'

Reverse primer targeted to the endogenous Lectin
1 gene sequence:
KVM165
                                   (SEQ ID No. 16)
5'-TCAAACTCAACAgCgACgAC-3'

Probe targeted to the endogenous Lectin 1 gene
sequence:
TM1242
                                   (SEQ ID No. 17)
JOE 5'-CCACAAACACATgCAggTTATCTTgg-3' BHQ1
```

2.1.2. Composition of the Reaction Mixture

| | | |
|---|---|---|
| 5.0 | µl | 2x PerfeCta qPCR FastMix II, ROX |
| 0.2 | µl | PRIM1038 [10 pmol/µl] |
| 0.2 | µl | PRIM1039 [10 pmol/µl] |
| 0.05 | µl | KVM164 [10 pmol/µl] |
| 0.05 | µl | KVM165 [10 pmol/µl] |
| 0.1 | µl | TM1788 [10 pmol/µl] |
| 0.1 | µl | TM1242 [10 pmol/µl] |
| x | µl | template DNA (20 ng*) |
| Water up to 10 µl | | |

Notes:
The 2x PerfeCta qPCR FastMix II, ROX was supplied by Quanta Bioscience. Other enzyme buffers may be used but performance should be verified.
Primers and labeled probes were ordered with Integrated DNA Technologies
*The amount of template DNA per reaction may vary but should be verified 2.1.3. Thermocycling Conditions

|  | Time | Temperature |
|---|---|---|
| Followed by: | 5 min. | 95° C. |
|  | 3 sec. | 95° C. |
|  | 30 sec. | 60° C. |
|  | For 35 cycles |  |
| Followed by: | Forever | 10° C. |

Notes:
The thermocycling conditions were validated for use on a BIORAD C1000 thermal cycler. Other equipment may be used but performance should be verified

2.1.4. Wavelength and Bandwidth Settings

|     | Excitation      | Emission        |
| --- | --------------- | --------------- |
| FAM | 495 nm ± 5 nm   | 517 nm ± 5 nm   |
| JOE | 530 nm ± 5 nm   | 555 nm ± 5 nm   |
| ROX | 581 nm ± 5 nm   | 607 nm ± 5 nm   |

Notes:
Wavelength and bandwidth settings were validated for use on a Tecan M1000 plate reader. Other equipment and settings may be used but performance should be verified

2.1.5. Control Samples

Following control samples should be included in the experiment to validate the results of test samples:
  Positive control: a DNA sample containing the target and endogenous sequences
  Negative control: a DNA sample containing only the endogenous sequence
  No template control: a water sample (no DNA)

2.1.6. Data Analysis

For all samples, fluorescent Signal to Background ratio's (S/B) are calculated for both the target and endogenous reaction.
Control samples should give the expected result, i.e.:
  The positive control should be scored "detected"
  The negative control should be scored "not detected"
  The no template control should only show fluorescent background levels
A sample is scored as follows:
  Detected: the target S/B and the endogenous S/B exceeds an acceptable threshold ratio, e.g., 2
  Not-detected: the target S/B is below an acceptable threshold ratio, e.g. 1, and, in addition, the endogenous S/B exceeds an acceptable threshold ratio, e.g., 2
  Inconclusive: the target and endogenous S/B are below an acceptable threshold, e.g., 1

Figure 1:
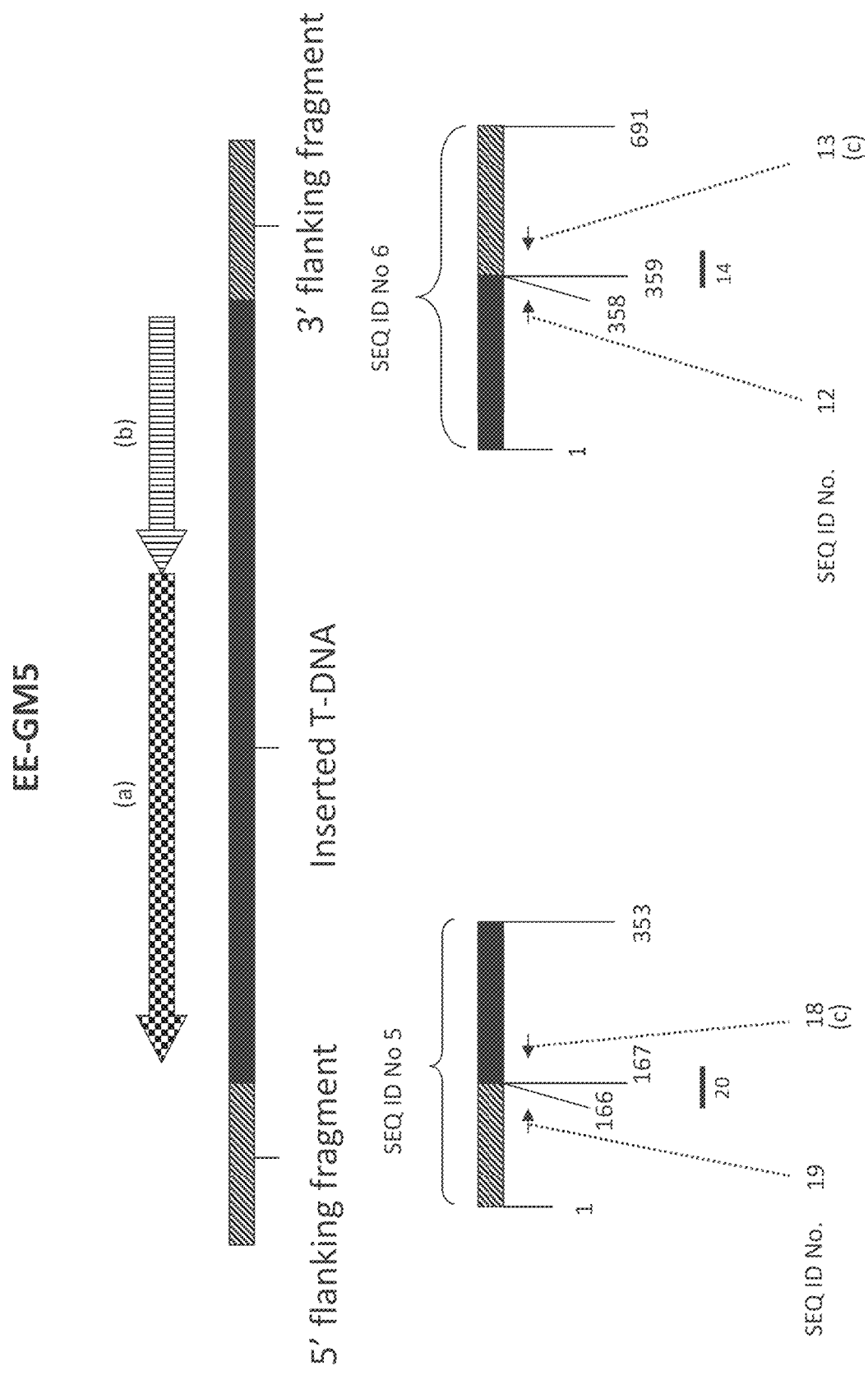
FIG. 1: Schematic representation of the relationship between the cited nucleotide sequences and primers. Black bar: inserted T-DNA; hatched bar: DNA flanking the T-DNA; checkered arrow (a): chimeric cry14Ab-1.b gene (see Table 1 for composition of the chimeric gene); hatched arrow (b): chimeric hppdPf-4 Pa gene (see Table 1 for composition of the chimeric gene); black arrows: oligonucleotide primers; (c) refers to complement of the indicated nucleotide sequence; black line: oligonucleotide probes (the number below is the representative SEQ ID No.). The numbers below the bars representing SEQ ID No. 5 and 6 are the nucleotide positions of the different elements in said sequences. Note: the scheme is not drawn to scale.
Figure 2:
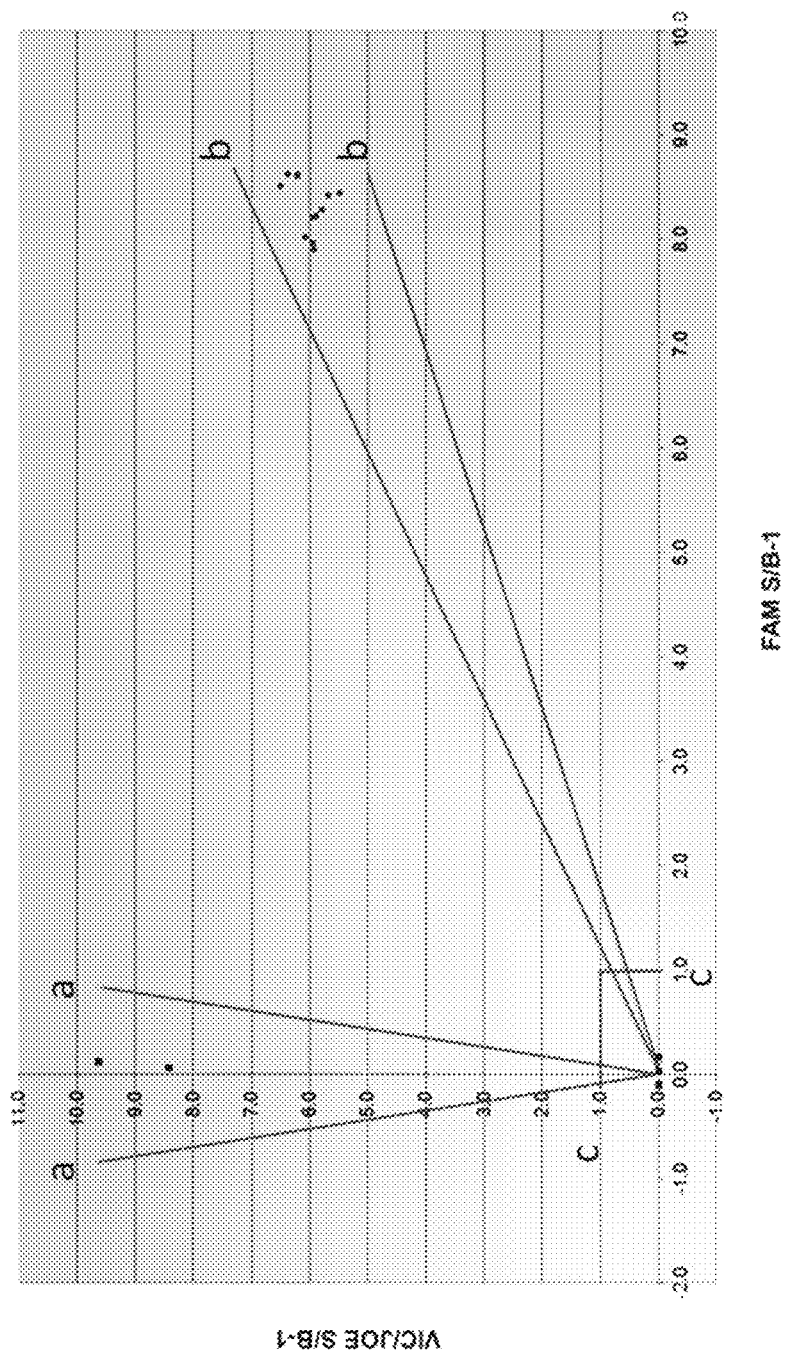
FIG. 2: End-Point method for EE-GM5 identity analysis.

FIG. 2 shows an example of the result of the method for a series of soybean samples containing EE-GM5 and conventional soybean samples. For each sample the S/B ratios for both the EE-GM5 specific reaction and the endogenous reaction are displayed.

2.2. End-Point Method for EE-GM5 Identity and Zygosity Analysis

This method describes a polymerase chain reaction detection method to analyze the presence and the zygosity status of event EE-GM5-specific DNA sequences in DNA samples obtained from biological samples, such as plant materials (e.g., leaf or seed) using standard DNA extraction procedures.

The method description outlines the reaction reagents, the oligonucleotide primer and probe sequences, the thermocycling conditions required to perform the reaction, and the fluorescent reader settings found appropriate for amplicon detection. It also provides general recommendations on the nature and use of control samples. In addition, guidance is provided for data analysis and interpretation, including an example of a method result taking into account the recommendations on the use of control materials and the guidance for data analysis.

It is noted that the method performance for zygosity analysis (of option 1 below) may be variety dependent due to the nature of the pre-insertion locus sequence. Therefore, performance verification is required for each variety in which the event is introgressed. For cases of inadequate performance, an alternative end-point method design for zygosity can be used (as in option 2 below) or an alternative Real-Time PCR method based on copynumber analysis can be used for zygosity determination, such as the one described below in section 2.3.

2.2.1. Method Design

The method uses the Taqman chemistry to amplify and detect two target sequences: a EE-GM5 specific reaction determines the presence of the event, a Pre-Insertion Locus-specific reaction determines the presence of the pre-insertion locus of the event.

Detection of only the EE-GM5 specific sequence indicates the presence of event EE-GM5 in a homozygous zygosity state.

Detection of the EE-GM5 specific and Pre-Insertion Locus specific sequence indicates the presence of event EE-GM5 in a hemizygous zygosity state.

Detection of only the Pre-Insertion Locus specific sequence indicates the absence of event EE-GM5.

2.2.1.1. EE-GM5-Specific Reaction

A. Option 1

Two primers, PRIM1040 and PRIM1041, were designed to amplify an amplicon of 84 bp spanning the junction region of the T-DNA 5' flanking sequence with the T-DNA insertion fragment for event EE-GM5.

A probe, TM1789 using FAM as fluorescent label and BHQ1 as quencher, was designed to detected the amplified sequence.

```
Forward primer targeted to the EE-GM5 T-DNA
sequence:
PRIM1041
                                   (SEQ ID No. 18)
5'-CATTgTgCTgAATAggTTTATAgCTATgAT-3'

Reverse primer targeted to the EE-GM5 T-DNA
5'flanking sequence:
PRIM1040
                                   (SEQ ID No. 19)
5'-TCAAATCAACATgggTgACTAgAAA-3'

Probe targeted to the junction of the EE-GM5
T-DNA and its' 5' flanking sequence:
TM1789
                                   (SEQ ID No. 20)
FAM 5'-CAgTACTgggCCCTTgTggCgCT-3' BHQ-1
```

B. Option 2

Two primers, PRIM2123 and PRIM1041, were designed to amplify an amplicon of 134 bp spanning the junction region of the T-DNA 5' flanking sequence with the T-DNA insertion fragment for event EE-GM5.

A probe, TM1789 using FAM as fluorescent label and BHQ1 as quencher, was designed to detected the amplified sequence.

```
Forward primer targeted to the EE-GM5 T-DNA
sequence:
PRIM1041
                                   (SEQ ID No. 18)
5'-CATTgTgCTgAATAggTTTATAgCTATgAT-3'

Reverse primer targeted to the EE-GM5 T-DNA
5'flanking sequence:
PRIM2123
                                   (SEQ ID No. 30)
5'-gCACTgTTTAACTTTAAATAACTCATTTgAg-3'
```

-continued

```
Probe targeted to the junction of the EE-GM5
T-DNA and its' 5' flanking sequence:
TM1789
                                   (SEQ ID No. 20)
FAM 5'-CAgTACTgggCCCTTgTggCgCT-3' BHQ-1
```

2.2.1.1. Pre-Insertion Locus Specific Reaction

A. Option 1

Two primers, PRIM1629 and PRIM1040, are designed to amplify an amplicon of 72 bp spanning the junction of the pre-insertion locus and the 5'flanking sequence of the EE-GM5 pre-insertion locus.

A MGB probe, TM2083 using VIC as fluorescent label and the MGB-NFQ as quencher, is designed to detect the amplified sequence

```
Forward primer targeted to the EE-GM5 pre-
insertion locus sequence:
PRIM1629
                                   (SEQ ID No. 21)
5'-TTggTgAAAAACAATTTggTgTACA-3'

Reverse primer targeted to the EE-GM5 T-DNA
5'flanking sequence:
PRIM1040
                                   (SEQ ID No. 19)
5'-TCAAATCAACATgggTgACTAgAAA-3'

Wild type probe targeting the junction of pre-
insertion locus and 5' flanking sequence:
TM2083
                                   (SEQ ID No. 22)
VIC 5'-AATCAAATCgACATCAATgT-3' MGB-NFQ
```

B. Option 2

Two primers, PRIM2122 and PRIM2123, are designed to amplify an amplicon of 193 bp spanning the junction of the pre-insertion locus and the 5'flanking sequence of the EE-GM5 pre-insertion locus.

A MGB probe, TM2327 using VIC as fluorescent label and the MGB-NFQ as quencher, is designed to detect the amplified sequence.

```
Forward primer targeted to the EE-GM5 pre-
insertion locus sequence:
PRIM2122
                                   (SEQ ID No. 31)
5' CAAgCAAAATAAgCAACTAgATCTATTgg-3'

Reverse primer targeted to the EE-GM5 T-DNA
5'flanking sequence:
PRIM2123
                                   (SEQ ID No. 30)
5'-gCACTgTTTAACTTTAAATAACTCATTTgAg-3'

Wild type probe targeting the junction of pre-
insertion locus and 5' flanking sequence:
TM2327
                                   (SEQ ID No. 32)
VIC 5'-TTTggTgAAAAACAATTTggTgT-3' MGB-NFQ
```

2.2.2. Composition of the Reaction Mixture

A. Option 1

| | | |
|---|---|---|
| 5.0 | µl | 2x PerfeCta qPCR FastMix II, ROX |
| 0.4 | µl | PRIM1040 [10 pmol/µl] |
| 0.2 | µl | PRIM1041 [10 pmol/µl] |
| 0.2 | µl | PRIM1629 [10 pmol/µl] |
| 0.1 | µl | TM1789 [10 pmol/µl] |
| 0.1 | µl | TM2083 [10 pmol/µl] |
| x | µl | template DNA (20 ng*) |
| Water up to 10 µl | | |

B. Option 2

| | | |
|---|---|---|
| 5.0 | ul | 2x PerfeCta qPCR FastMix II, ROX |
| 0.2 | ul | PRIM1041 [10 pmol/µl] |
| 0.2 | ul | PRIM2122 [10 pmol/µl] |
| 0.2 | ul | PRIM2123 [10 pmol/µl] |
| 0.1 | µl | TM1789 [10 pmol/µl] |
| 0.1 | µl | TM2327 [10 pmol/µl] |
| x | µl | template DNA (20 ng*) |
| Water up to 10 µl | | |

Notes:
The 2x PerfeCta qPCR FastMix II, ROX was supplied by Quanta Bioscience. Other enzyme buffers may be used but performance should be verified.
Primers and labeled probes were ordered with Integrated DNA Technologies
*The amount of template DNA per reaction may vary but should be verified 2.2.3. Thermocycling Conditions (the Same for Option 1 and 2)

| | Time | | Temperature |
|---|---|---|---|
| Followed by: | 5 | min. | 95° C. |
| | 3 | sec. | 95° C. |
| | 30 | sec. | 60° C. |
| | For 35 cycles | | |
| Followed by: | Forever | | 10° C. |

Notes:
The thermocycling conditions were validated for use on a BIORAD C1000 thermal cycler. Other equipment may be used but performance should be verified 2.2.4. Wavelength and Bandwidth Settings (the Same for Option 1 and 2)

| | Excitation | Emission |
|---|---|---|
| FAM | 495 nm ± 5 nm | 517 nm ± 5 nm |
| JOE | 530 nm ± 5 nm | 555 nm ± 5 nm |
| ROX | 581 nm ± 5 nm | 607 nm ± 5 nm |

Notes:
Wavelength and bandwidth settings were validated for use on a Tecan M1000 plate reader. Other equipment and settings may be used but performance should be verified 2.2.5. Control Samples (the Same for Option 1 and 2)

Following control samples should be included in the experiment to validate the results of test samples:

Homozygous control: a DNA sample containing the target sequence in a homozygous state Hemizygous control: a DNA sample containing the target sequence in a hemizygous state Wild type control: a DNA sample not containing the target sequence No template control: a water sample 2.2.6. Data Analysis (the Same for Option 1 and 2)

For all samples, fluorescent Signal to Background ratio's (S/B) are calculated for both the target and pre-insertion locus reaction.

Control samples should give the expected result, i.e.:

The homozygous control should be scored "homozygous"

The hemizygous control should be scored "hemizygous"

The wild type control should be scored "wild type"

The no template control should only show fluorescent background levels

A sample is scored as follows:
- homozygous: the target S/B exceeds an acceptable threshold ratio, e.g. 2, and the pre-insertion locus S/B is below an acceptable threshold ratio, e.g., 1
- hemizygous: both the target and pre-insertion locus S/B exceeds an acceptable threshold ratio, e.g., 2
- wild type: the target S/B is below an acceptable threshold ratio, e.g. 1, and the pre-insertion locus S/B exceeds an acceptable threshold ratio, e.g., 2
- Inconclusive: the target and pre-insertion locus S/B are below an acceptable threshold, e.g., 1

Figure 3:
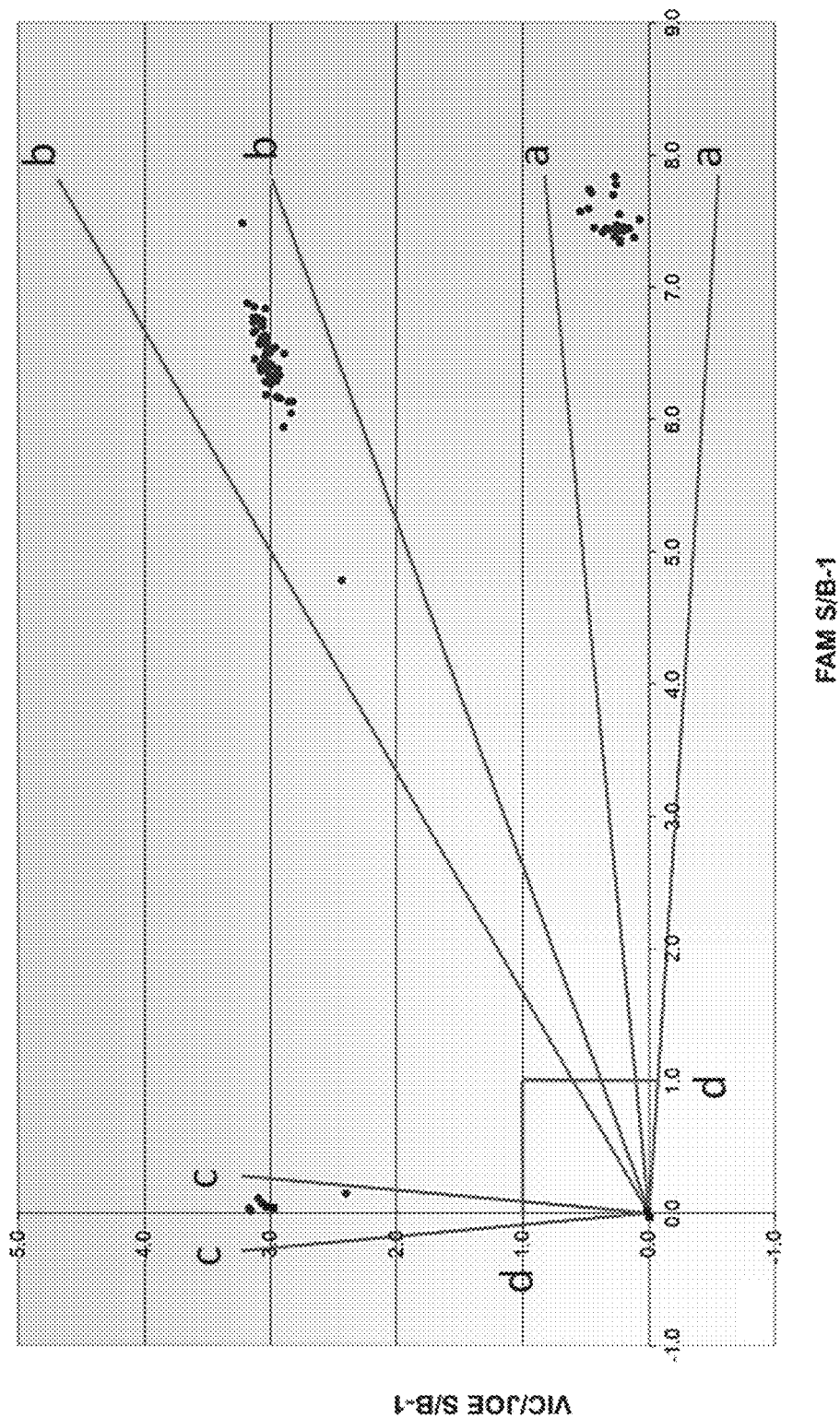
FIG. 3: End Point method for EE-GM5 GM5 identity and zygosity analysis.

FIG. 3 shows an example of the result of the method (of option 1 above) for a series of soybean samples containing EE-GM5 in a homozygous state, soybean samples containing EE-GM5 in a hemizygous state and conventional soybean samples.

2.3. Real-Time PCR Method for EE-GM5 Identity and Zygosity Analysis

The method describes a quantitative Real-Time polymerase chain reaction detection method to analyze the zygosity status of event EE-GM5 DNA sequences in DNA samples obtained from biological samples, such as plant materials (e.g., leaf or seed) using standard DNA extraction procedures.

The method description outlines the reaction reagents, the oligonucleotide primer and probe sequences, the thermocycling conditions required to perform the reaction, incl the fluorescent reader settings found appropriate for amplicon detection. It also provides general recommendations on the nature and use of control samples. In addition, guidance is provided for data analysis and interpretation.

This method is not variety dependent and can be used as alternative zygosity analysis method to the method described in section 2.2 above.

2.3.1. Method Design

The method uses the Taqman chemistry and principles of Real-Time PCR to quantify the relative copy number of a EE-GM5 specific sequence.

The method includes a EE-GM5 specific reaction to quantify the EE-GM5 copy number, and a taxon-specific reaction for normalization of the EE-GM5 copy number.

Samples containing the EE-GM5 insertion sequence in a homozygous state have a relative copy number that is two-fold higher than hemizygous samples. Azygous samples do not amplify the EE-GM5 sequence.

2.3.2. EE-GM5-Specific Reaction

Two primers, PRIM1038 and PRIM1039, were designed to amplify an amplicon of 85 bp spanning the junction region of the 3' flanking sequence with the T-DNA insertion fragment for event EE-GM5.

A probe, TM1788 using FAM as fluorescent label and BHQ1 as quencher, was designed to quantify the amplified sequence.

```
Forward primer targeted to the EE-GM5 T-DNA
sequence:
PRIM1038
                                    (SEQ ID No. 12)
5'-gAgCCACCTTCCTTTTCCACTA-3'

Reverse primer targeted to the EE-GM5
3' flanking sequence:
PRIM1039
                                    (SEQ ID No. 12)
5'-ATAgggTTACTgCTTCgTAAAATAAgCA-3'

Probe targeted to the junction of the EE-GM5
T-DNA and its' 3'flanking sequence:
TM1788
                                    (SEQ ID No. 14)
FAM 5'-CgCgTCCATgATgCTgCgACTATg-3' BHQ-1
```

2.3.3. Taxon-Specific Reaction

Two primers, KVM164 and KVM165, were designed to amplify an amplicon of 102 bp of the soybean endogenous lectin1 gene sequence.

A probe, TM1242 using JOE as fluorescent label and BHQ1 as quencher, was designed to quantify the amplified sequence

```
Forward primer targeted to the endogenous
Lectin 1 gene sequence:
KVM164
                                    (SEQ ID No. 15)
5'-CTTTCTCgCACCAATTgACA-3'

Reverse primer targeted to the endogenous
Lectin 1 gene sequence:
KVM165
                                    (SEQ ID No. 16)
5'-TCAAACTCAACAgCgACgAC-3'

Probe targeted to the endogenous Lectin 1
gene sequence:
TM1242
                                    (SEQ ID No. 17)
JOE 5'-CCACAAACACATgCAggTTATCTTgg-3' BHQ1
```

2.3.4. Composition of the Reaction Mixture

| | | |
|---|---|---|
| 5.0 | μl | 2x PerfeCta qPCR FastMix II, Low ROX |
| 0.2 | μl | PRIM1038 [10 pmol/μl] |
| 0.2 | μl | PRIM1039 [10 pmol/μl] |
| 0.2 | μl | KVM164 [10 pmol/μl] |
| 0.2 | μl | KVM165 [10 pmol/μl] |
| 0.05 | μl | TM1788 [10 pmol/μl] |
| 0.05 | μl | TM1242 [10 pmol/μl] |
| x | μl | template DNA (20 ng*) |
| Water up to 10 μl | | |

Notes:
The 2x PerfeCta qPCR FastMix II, LOW ROX was supplied by Quanta Bioscience. Other enzyme buffers may be used but performance should be verified.
Primer and labeled probes were ordered with Integrated DNA Technologies
*The amount of template DNA per reaction may vary but should be verified

2.3.5. Thermocycling Conditions

| | Time | | Temperature |
|---|---|---|---|
| Followed by: | 5 | min. | 95° C. |
| | 3 | sec. | 95° C. |
| | 30 | sec. | 60° C. ** |
| | For 35 cycles | | |
| Followed by: | Forever | | 10° C. |

Notes:
** Fluorescent read-out is performed at each cycle, upon finalization of the primer elongation step at 60° C.
The thermocycling conditions were validated for use on a ViiA7 and Quantstudio 7 Real-Time PCR apparatus. Other equipment may be used but performance should be verified

2.3.6. Control Samples

Following control samples should be included in the experiment to validate the results of test samples
- Homozygous control: a DNA sample containing the target sequence in a homozygous state
- Hemizygous control: a DNA sample containing the target sequence in a hemizygous state Wild type control: a DNA sample not containing the target sequence No template control: a water sample 2.3.7. Data Analysis Data analysis is performed using the ddCt method. In this method the copynumber is calculated for all samples relative to a chosen reference sample. It is recommended to use the hemizygous control as the reference sample.

Control samples should give the expected result, i.e.:

The homozygous control should be scored "homozygous"

The hemizygous control should be scored "hemizygous"

The wild type control should be scored "wild type"

The no template control should only show fluorescent background levels

A sample is scored as follows:

homozygous: the relative copynumber is 2+/−an acceptable threshold, e.g. 0.5 hemizygous: the relative copynumber is 1+/−an acceptable threshold, e.g. 0.25 wild type: the relative copynumber is 0+an acceptable threshold, e.g. 0.1

Inconclusive: the relative copynumber is outside the acceptable ranges for homozygous, hemizygous and wild type samples 2.4. Real-Time PCR Method for EE-GM5 Low Level Presence Analysis This method describes a detection method to analyze the Low Level Presence of event EE-GM5 DNA sequences obtained from bulked plant materials (e.g., leaf or seed) or processed materials (e.g., food or feed containing processed soybean grain) using standard DNA extraction procedures.

The method description outlines the reaction reagents, the oligonucleotide primer and probe sequences, and the thermocycling conditions required to perform the reaction. It also provides general recommendations on the concurrent use of a taxon-specific method to support data analysis and result interpretation. In addition, recommendations are provided on the nature and use of control samples.

It is noted that alternative methods may be available for the intended purpose, including but not limited to digital droplet PCR methods. Digital droplet PCR methods use End-Point methods for event identity analysis, as described in section 1.1, in combination with principles of subsampling on the extracted DNA sample. In this method the low level presence of the event is determined based on the ratio of DNA subsamples found positive and negative for the event sequence.

2.4.1 Method Design

The method uses the Taqman chemistry and principles of Real-Time PCR to detect or quantify low levels of EE-GM5 in a DNA sample.

Two primers, PRIM1040 and PRIM1041, are designed to amplify an amplicon of 84 bp spanning the junction region of the 5' flanking sequence with the T-DNA insertion fragment for event EE-GM5.

A probe, TM1789 using FAM as fluorescent label and BHQ1 as quencher, is designed to quantify the amplified sequence.

Forward primer targeted to the EE-GM5 T-DNA sequence:
PRIM1041
(SEQ ID No. 18)
5'-CATTgTgCTgAATAggTTTATAgCTATgAT-3'

Reverse primer targeted to the EE-GM5 T-DNA 5' flanking sequence:
PRIM1040
(SEQ ID No. 19)
5'-TCAAATCAACATgggTgACTAgAAA-3'

Probe targeted to the junction of the EE-GM5 T-DNA and its' 5' flanking sequence:
TM1789
(SEQ ID No. 20)
FAM 5'-CAgTACTgggCCCTTgTggCgCT-3' BHQ-1

2.4.2 Composition of the Reaction Mixture

| 10.0 | µl | 2x PerfeCta qPCR Fastmix II, Low ROX |
| 0.5 | µl | PRIM1040 [10 pmol/µl] |
| 0.5 | µl | PRIM1041 [10 pmol/µl] |
| 0.5 | µl | TM1789 [10 pmol/µl] |
| x | µl | template DNA (200 ng*) |
| Water up to 20 µl | | |

Notes:
The 2x PerfeCta qPCR FastMix II, LOW ROX was supplied by Quanta Bioscience. Other enzyme buffers may be used but performance should be verified.
Primer and labeled probes were ordered with Integrated DNA Technologies
*The amount of template DNA per reaction may vary but should be verified 2.4.3 Thermocycling Conditions

| | Time | Temperature |
|---|---|---|
| Followed by: | 5 min. | 95° C. |
| | 3 sec. | 95° C. |
| | 30 sec. | 60° C. ** |
| | For 40 cycles | |
| Followed by: Forever | | 10° C. |

Notes:
**Fluorescent read-out is performed at each cycle, upon finalization of the primer elongation step at 60° C.
The thermocycling conditions were validated for use on a ViiA7 and Quantstudio 7 Real-Time PCR apparatus. Other equipment may be used but performance should be verified 2.4.4 Taxon Specific Method A Real-Time PCR detection method targeting an endogenous sequence should be performed concurrently on an identical amount of template DNA as used in the target specific Real-Time PCR method. The outcome of the taxon specific method should be used to support data analysis and interpretation, i.e. to normalize the amount of input DNA and to validate any negative results for the target specific reaction.

2.4.5 Test Samples, Calibration Samples and Control Samples

It is recommended that all test samples are analyzed in duplicate.

A set of calibration samples is included in the experiment to generate standard curves for both the target and taxon specific method.

In addition the following control samples are included:

Positive control: a DNA sample containing the target sequence at the level of the Limit Of Detection, Negative control: a DNA sample containing only the endogenous sequence No template control: a water sample 2.4.6 Data Analysis For all samples threshold cycle values (i.e., Ct values) are determined for both the target and taxon specific method. A threshold cycle is defined as the cycling number at which the amplification plot for a given sample reaches a defined signal threshold (see FIG. 4)

Standard curve formulas are calculated for both the target and taxon specific method using the Ct values and the amount of genome copies of the calibration samples The standard curve parameters should fulfill acceptance criteria for slope and linearity ($R^2$), e.g.

$-3.2 <$ slope $<-3.6$ $R^2 > 0.98$

For all samples, the genome copy number for the target and endogenous method is calculated using linear regression analysis.

The amount of low level presence relative to the total amount of taxon specific DNA is determined by calculating the % ratio of the genome copy numbers for the target and taxon specific method.

Control samples should give the expected result, i.e.:

The positive control should be scored "detected"

The negative control should be scored "not detected"

The no template control should only show fluorescent background levels

Figure 4:
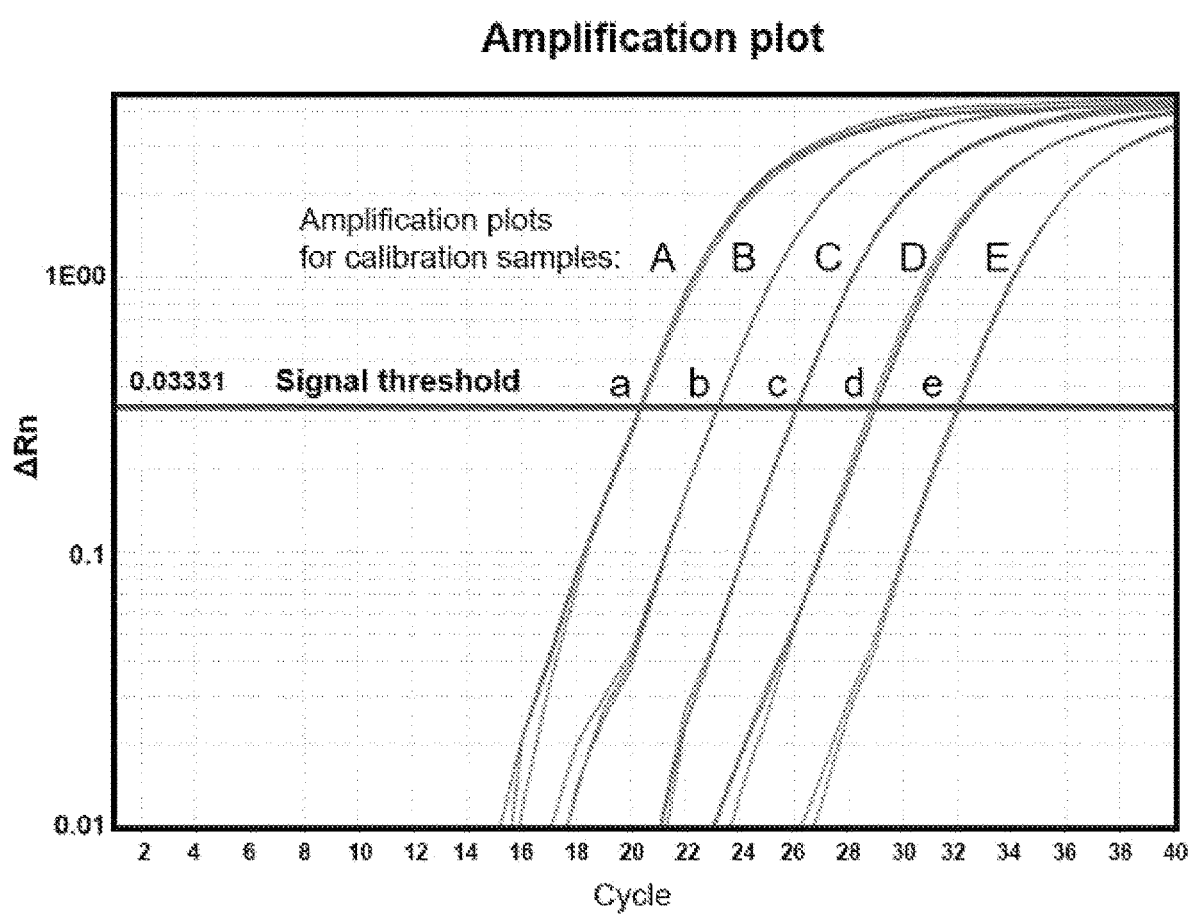
FIG. 4: Real-Time PCR method for EE-GM5 Low Level Presence analysis

A sample is scored as follows:

Detected: the low level presence is above the limit of detection for all replicates, taking into account the measurement uncertainty of the method Not-detected: the low level presence is below the limit of detection for all replicates, taking into account the measurement uncertainty of the method Inconclusive: replicated samples give inconsistent scores FIG. 4 shows an example of the result of the method performed on the calibration samples.

3. Introgression of EE-GM5 into Preferred Cultivars

Elite event EE-GM5 was introduced by repeated backcrossing into six different elite soybean lines. The lines were selected to represent a range of maturities: two lines from MG I, one line from MG III, two lines from MG VI and one line from MG IX. One of the MG I lines and the MG III line contained the Rhg1 native resistance allele from PI 88788, and one of the MG VI lines carried the Rhg1 and Rhg4 native resistance alleles from PI 437654. The other three lines were susceptible to SCN.

Also, in initial testing, in several experiments, no biologically significant differences were observed for Cry14Ab-1 of HPPD-4 protein expression levels measured in leaves of greenhouse-grown plants (as measured with ELISA or Western blot (only normal assay variation was seen)), and no significant differences were seen in the standard greenhouse SCN assay results (measuring % reduction in SCN cysts vs. the Thorne control), when event EE-GM5 was introgressed from Thorne background into other soybean germplasm backgrounds (of different maturity, at different stages of introgression), compared to what was found for EE-GM5 in the Thorne background.

Introgression of the elite event EE-GM5 into other soybean cultivars does not significantly influence any of the desirable phenotypic or agronomic characteristics of these cultivars (no linkage drag) while expression of the transgenes meets commercially acceptable levels. This confirms the status of event EE-GM5 as an elite event.

Furthermore, elite event EE-GM5 is advantageously combined with other soybean elite transformation events. Particularly useful plants according to the invention are plants containing EE-GM5 combined with another soybean transformation event, or a combination of more than one other soybean transformation event, such as those listed in the databases of various national or regional regulatory agencies, including but not limited to Event MON87751 (described in WO2014201235 and USDA-APHIS Petition 13-337-01p), Event pDAB8264.42.32.1 (described in WO2013010094), Event DAS-81419-2 (aka Conkesta™ Soybean, described in WO2013016527 and USDA-APHIS Petition 12-272-01p), Event EE-GM3 (aka FG-072, MST-FG072-3, described in WO2011063411, USDA-APHIS Petition 09-328-01p), Event SYHTOH2 (aka 0H2, SYN-000H2-5, described in WO2012/082548 and 12-215-01p), Event DAS-68416-4 (aka Enlist Soybean, described in WO2011/066384 and WO2011/066360, USDA-APHIS Petition 09-349-01p), Event DAS-81615-9 (described in WO2014004458), Event DAS-44406-6 (aka Enlist E3, DAS-44406-6, described in WO2012/075426 and USDA-APHIS 11-234-01p), Event MON87708 (Xtend Soybeans, described in WO2011/034704 and USDA-APHIS Petition 10-188-01p), Event MON89788 (aka Genuity Roundup Ready 2 Yield, described in WO2006/130436 and USDA-APHIS Petition 06-178-01p), Event DAS-14536-7 (described in WO2012/075429), Event 40-3-2 (aka RoundUp Ready, MON-04032-6, described in USDA-APHIS Petition 93-258-01), Event A2704-12 (aka LL27, ACS-GM005-3, described in WO2006108674 and USDA-APHIS Petition 96-068-01p), Event 127 (aka BPS-CV127-9, described in WO2010/080829), Event A5547-127 (aka LL55, ACS-GM006-4, described in WO2006108675 and in USDA-APHIS Petition 96-068-01p), Event MON87754 (aka Vistive III, MON-87754-1, described in WO2010/024976), Event HOS (aka DP-305423-1, Plenish High Oleic Soybean, described in WO2008054747), Event MON87701 (aka MON-87701-2, described in WO2009064652 and USDA-APHIS Petition 09-082-01p), Event MON 87705 (aka MON-87705-6, described in WO2010/037016 and USDA-APHIS Petition 09-201-01p), Event MON87712 (aka MON-87712-4, described in WO2012/051199), Event pDAB4472-1606 (aka Event 1606, described in WO2012/033794), Event 3560.4.3.5 (aka DP-356043-5, described in WO2008/002872), Event MON87769 (aka MON-87769-7, described in WO2009102873 and in USDA-APHIS Petition 09-183-01p), or any combination of EE-GM5 with several of these other transgenic soybean events, such as a combination of EE-GM5 with any one of the following combinations: Event MON98788×MON87708 (aka Roundup Ready 2 Xtend Soybeans, MON-87708-9×MON-89788-1), Event 5 HOS× Event 40-3-2 (aka Plenish High Oleic Soybeans×Roundup Ready Soybeans), Event EE-GM3×EE-GM2 (aka FG-072×LL55, described in WO2011063413), Event MON 87701×MON 89788 (aka Intacta RR2 Pro Soybean, MON-87701-2×MON-89788-1), DAS-81419-2×DAS-44406-6 (aka Conkesta™ Enlist E3™ Soybean, DAS-81419-2× DAS-44406-6), Event DAS-81419-2×Event DAS-68416-4 (described in WO2013016516), Event DAS-68416-4×Event MON 89788 (aka Enlist™ RoundUp Ready® 2 Soybean, DAS-68416-4×MON-89788-1), Event MON-87769-7× Event MON-89788-1 (aka Omega-3×Genuity Roundup Ready 2 Yield Soybeans), MON 87705×MON 89788 (aka Vistive Gold, MON-87705-6×MON-89788-1), MON 87769×MON 89788 (aka Omega-3×Genuity Roundup Ready 2 Yield Soybeans, MON-87769-7×MON-89788-1).

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GM5 was deposited at the ATCC (10801 University Blvd., Manassas, Va. 20110-2209) on Nov. 9, 2016, under ATCC accession number PTA-123625, and the viability thereof was confirmed. Alternative names for EE-GM5 are event GMB151 or BCS-GM151-6.

The above description of the invention is intended to be illustrative and not limiting.

Various changes or modifications in the embodiments described may occur to those skilled in the art. These can be made without departing from the spirit or scope of the invention.

The invention claimed is:

1. A nucleic acid molecule comprising
   (a) a nucleotide sequence with at least 99% sequence identity to the nucleotide sequence of SEQ ID No. 5, 6, 24 or 25, or to the complement of SEQ ID No. 5, 6, 24 or 25;
   (b) the nucleotide sequence of SEQ ID No. 1, 2, 3, 4, 5, 6, 24, or 25 or the complement of SEQ ID No. 1, 2, 3, 4, 5, 6, 24, or 25; or
   (c) the nucleotide sequence of SEQ ID No. 1 or 3 and the nucleotide sequence of SEQ ID No. 2 or 4, or the complement of SEQ ID No. 1 or 3 and the complement of SEQ ID No. 2 or 4.

2. The nucleic acid molecule of claim 1, further comprising:
   (a) the nucleotide sequence of SEQ ID No. 7 and 9, or the complement of SEQ ID No. 7 and 9;
   (b) the nucleotide sequence of SEQ ID No. 11 from nucleotide position 188 to nucleotide position 7368; or
   (c) a nucleotide sequence having at least 98%, or least 99%, or at least 99.5% or at least 99.9% sequence identity to the nucleotide sequence of (a) or (b).

3. The nucleic acid molecule of claim 2, wherein the molecule comprises the nucleotide sequence of SEQ ID No. 5 or 24 and SEQ ID No. 6 or 25, or the complement of SEQ ID No. 5 or 24 and SEQ ID No. 6 or 25.

4. A nucleic acid molecule obtainable from the seed deposited at the ATCC under accession number PTA-123625, wherein said nucleic acid molecule comprises the nucleotide sequence of any one of SEQ ID No. 1, 3, or 5 and the nucleotide sequence of any one of SEQ ID No. 2, 4, or 6.

5. Soybean genomic DNA comprising the nucleic acid molecule of claim 1.

6. A nucleic acid molecule comprising the nucleotide sequence of SEQ ID No. 11 from nucleotide position 131 to nucleotide position 7941, or a nucleotide sequence having at least 95%, at least 96%, at least 97%, at least 98%, or at least 99% sequence identity to the nucleotide sequence of SEQ ID No. 11 from nucleotide position 131 to nucleotide position 7941.

7. A nucleic acid molecule that specifically characterizes soybean elite transformation event EE-GM5, wherein it comprises (i) the nucleotide sequence of any one of SEQ ID No. 1, 3, or 5, and/or (ii) the nucleotide sequence of SEQ ID No. 2, 4, or 6.

8. A nucleic acid molecule comprising (a) a nucleotide sequence with at least 98% sequence identity to SEQ ID No. 7 or 9; or (b) a nucleotide sequence with at least 95% sequence identity to SEQ ID No. 11.

9. The nucleic acid molecule of claim 1, wherein the nucleic acid molecule comprises a nucleotide sequence with at least 99% sequence identity to the nucleotide sequence of SEQ ID No. 5, 6, 24 or 25, or to the complement of SEQ ID No. 5, 6, 24 or 25.

10. The nucleic acid molecule of claim 1, wherein the nucleic acid molecule comprises the nucleotide sequence of SEQ ID No. 1 or the complement of SEQ ID No. 1.

11. The nucleic acid molecule of claim 1, wherein the nucleic acid molecule comprises the nucleotide sequence of SEQ ID No. 2 or the complement of SEQ ID No. 2.

12. The nucleic acid molecule of claim 1, wherein the nucleic acid molecule comprises the nucleotide sequence of SEQ ID No. 3 or the complement of SEQ ID No. 3.

13. The nucleic acid molecule of claim 1, wherein the nucleic acid molecule comprises the nucleotide sequence of SEQ ID No. 4 or the complement of SEQ ID No. 4.

14. The nucleic acid molecule of claim 1, wherein the nucleic acid molecule comprises the nucleotide sequence of SEQ ID No. 5 or the complement of SEQ ID No. 5.

15. The nucleic acid molecule of claim 1, wherein the nucleic acid molecule comprises the nucleotide sequence of SEQ ID No. 6 or the complement of SEQ ID No. 6.

16. The nucleic acid molecule of claim 1, wherein the nucleic acid molecule comprises the nucleotide sequence of SEQ ID No. 24 or the complement of SEQ ID No. 24.

17. The nucleic acid molecule of claim 1, wherein the nucleic acid molecule comprises the nucleotide sequence of SEQ ID No. 25 or the complement of SEQ ID No. 25.

18. The nucleic acid molecule of claim 1, wherein the nucleic acid molecule comprises the nucleotide sequence of SEQ ID No. 1 or 3 and the nucleotide sequence of SEQ ID No. 2 or 4, or the complement of SEQ ID No. 1 or 3 and the complement of SEQ ID No. 2 or 4.

19. The nucleic acid molecule of claim 6, wherein the nucleic acid molecule comprises the nucleotide sequence of SEQ ID No. 11 from nucleotide position 131 to nucleotide position 7941.

20. The nucleic acid molecule of claim 6, wherein the nucleic acid molecule comprises a nucleotide sequence having at least 95% sequence identity to the nucleotide sequence of SEQ ID No. 11 from nucleotide position 131 to nucleotide position 7941.

21. The nucleic acid molecule of claim 6, wherein the nucleic acid molecule comprises a nucleotide sequence having at least 96% sequence identity to the nucleotide sequence of SEQ ID No. 11 from nucleotide position 131 to nucleotide position 7941.

22. The nucleic acid molecule of claim 6, wherein the nucleic acid molecule comprises a nucleotide sequence having at least 97% sequence identity to the nucleotide sequence of SEQ ID No. 11 from nucleotide position 131 to nucleotide position 7941.

23. The nucleic acid molecule of claim 6, wherein the nucleic acid molecule comprises a nucleotide sequence having at least 98% sequence identity to the nucleotide sequence of SEQ ID No. 11 from nucleotide position 131 to nucleotide position 7941.

24. The nucleic acid molecule of claim 6, wherein the nucleic acid molecule comprises a nucleotide sequence having at least 99% sequence identity to the nucleotide sequence of SEQ ID No. 11 from nucleotide position 131 to nucleotide position 7941.

25. The nucleic acid molecule of claim 8, wherein the nucleic acid molecule comprises a nucleotide sequence with at least 98% sequence identity to SEQ ID No. 7 or 9.

26. The nucleic acid molecule of claim 8, wherein the nucleic acid molecule comprises a nucleotide sequence with at least 95% sequence identity to SEQ ID No. 11.

* * * * *

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: 5' junction EE-GM5
<220> FEATURE:
<221> NAME/KEY: misc_feature
<222> LOCATION: (1)..(10)
<223> OTHER INFORMATION: part of T-DNA 5' flanking region
<220> FEATURE:
<221> NAME/KEY: misc_feature
<222> LOCATION: (11)..(20)
<223> OTHER INFORMATION: part of T-DNA

<400> SEQUENCE: 1
gaaaaaatca gtactgggcc                                              20

<210> SEQ ID NO 2
<211> LENGTH: 20
<212> TYPE: DNA
<213> ORGANISM: Artificial Sequence
<220> FEATURE:
<223> OTHER INFORMATION: 3' junction EE-GM5
<220> FEATURE:
<221> NAME/KEY: misc_feature
<222> LOCATION: (1)..(10)
<223> OTHER INFORMATION: part of T-DNA
<220> FEATURE:
<221> NAME/KEY: misc_feature
<222> LOCATION: (11)..(20)
<223> OTHER INFORMATION: part of T-DNA 3' flanking region

<400> SEQUENCE: 2
ttccactatc gcgtccatga                                              20

<210> SEQ ID NO 3
<211> LENGTH: 40
<212> TYPE: DNA
<213> ORGANISM: Artificial Sequence
<220> FEATURE:
<223> OTHER INFORMATION: EE-GM5 5' junction
<220> FEATURE:
<221> NAME/KEY: misc_feature
<222> LOCATION: (1)..(20)
<223> OTHER INFORMATION: part of T-DNA 5' flanking region
<220> FEATURE:
<221> NAME/KEY: misc_feature
<222> LOCATION: (21)..(40)
<223> OTHER INFORMATION: part of T-DNA

<400> SEQUENCE: 3
tgggtgacta gaaaaaatca gtactgggcc cttgtggcgc                        40

<210> SEQ ID NO 4
<211> LENGTH: 40
<212> TYPE: DNA
<213> ORGANISM: Artificial Sequence
<220> FEATURE:
<223> OTHER INFORMATION: EE-GM5 3' junction
<220> FEATURE:
<221> NAME/KEY: misc_feature
```

```
<222> LOCATION: (1)..(20)
<223> OTHER INFORMATION: part of T-DNA
<220> FEATURE:
<221> NAME/KEY: misc_feature
<222> LOCATION: (21)..(40)
<223> OTHER INFORMATION: part of T-DNA 3' flanking region

<400> SEQUENCE: 4
caccttcctt ttccactatc gcgtccatga tgctgcgact                         40

<210> SEQ ID NO 5
<211> LENGTH: 353
<212> TYPE: DNA
<213> ORGANISM: Artificial Sequence
<220> FEATURE:
<223> OTHER INFORMATION: EE-GM5 5' region
<220> FEATURE:
<221> NAME/KEY: misc_feature
<222> LOCATION: (1)..(166)
<223> OTHER INFORMATION: part of T-DNA 5' flanking region
<220> FEATURE:
<221> NAME/KEY: misc_feature
<222> LOCATION: (167)..(353)
<223> OTHER INFORMATION: T-DNA

<400> SEQUENCE: 5
aaaattataa taatcaatta agtaattcac tcaagaaaca cattaatcaa ataatcaatt    60
ctaataggaa aaaatatttt aaatagcact gtttaacttt aaataactca tttgagatga   120
tatgatgatt cagagtcaaa tcaacatggg tgactagaaa aaatcagtac tgggcccttg   180
tggcgctcta tcatagctat aaacctattc agcacaatgg gctcgagggc gatcgctacg   240
ggaactcgag aaggatcctt aagcttctag ttctagagcg gccgctcgag gaattctgga   300
ttttagtact ggattttggt tttaggaatt agaaatttta ttgatagaag tat          353

<210> SEQ ID NO 6
<211> LENGTH: 691
<212> TYPE: DNA
<213> ORGANISM: Artificial Sequence
<220> FEATURE:
<223> OTHER INFORMATION: EE-GM5 3' region
<220> FEATURE:
<221> NAME/KEY: misc_feature
<222> LOCATION: (1)..(358)
<223> OTHER INFORMATION: part of T-DNA
<220> FEATURE:
<221> NAME/KEY: misc_feature
<222> LOCATION: (359)..(691)
<223> OTHER INFORMATION: part of T-DNA 3' flanking region

<400> SEQUENCE: 6
aaaagaaatg atttaaattg ctgcaataga agtagaatgc ttgattgctt gagattcgtt    60
tgttttgtat atgttgtgtt gagaatttat tgtcctctcc aaatgaaatg aacttcctta   120
tatagaggaa gggtcttgcg aaggatagtg ggattgtgcg tcatccctta cgtcagtgga   180
gatatcacat caatccactt gctttgaaga cgtggttgga acgtcttctt tttccacgat   240
gctcctcgtg ggtgggggtc catctttggg accactgtcg gtagaggcat cttgaacgat   300
agcctttcct ttatcgcaat gatggcattt gtaggagcca ccttcctttt ccactatcgc   360
gtccatgatg ctgcgactat gatctagttg cttattttac gaagcagtaa ccctattcca   420
atagatctag ttgcttattt tgcttgtgct agttgtcgat tgagttattc aaataaaccg   480
gaatggcagt aacaactcca ccagaagacg acgaacaatc attctcagca gcagccggcg   540
gcaccgccac cctgacggag aaattaacga ctctgttttc tctgccatcc caatccctca   600
```

```
acctgtaaca caaagactgc aagctatgat caggcaccga ccctccaaga aaatccgaaa    660
ccgctattct cgccactccg atgtctctca c                                   691

<210> SEQ ID NO 7
<211> LENGTH: 3558
<212> TYPE: DNA
<213> ORGANISM: Artificial Sequence
<220> FEATURE:
<223> OTHER INFORMATION: cry14Ab-1.b coding sequence
<220> FEATURE:
<221> NAME/KEY: CDS
<222> LOCATION: (1)..(3558)

<400> SEQUENCE: 7 atg gat tgc aac ctt cag tcc cag cag aac att cca tac aac gtg ctc       48
Met Asp Cys Asn Leu Gln Ser Gln Gln Asn Ile Pro Tyr Asn Val Leu
1               5                   10                  15 gct att cca gtt tct aac gtg aac tcc ctt act gat acc gtg ggt gat       96
Ala Ile Pro Val Ser Asn Val Asn Ser Leu Thr Asp Thr Val Gly Asp
            20                  25                  30 ctt aag aag gct tgg gaa gag ttc caa aag acc gga tct ttc tct ctt      144
Leu Lys Lys Ala Trp Glu Glu Phe Gln Lys Thr Gly Ser Phe Ser Leu
        35                  40                  45 act gct ctc caa cag gga ttc tct gct tct caa ggt gga acc ttc aac      192
Thr Ala Leu Gln Gln Gly Phe Ser Ala Ser Gln Gly Gly Thr Phe Asn
    50                  55                  60 tac ctt acc ctt ctc cag tct gga att tct ctt gct gga tcc ttc gtt      240
Tyr Leu Thr Leu Leu Gln Ser Gly Ile Ser Leu Ala Gly Ser Phe Val
65                  70                  75                  80 cca ggt gga act ttc gtg gct cca atc atc aac atg gtg att gga tgg      288
Pro Gly Gly Thr Phe Val Ala Pro Ile Ile Asn Met Val Ile Gly Trp
                85                  90                  95 ctt tgg cca cac aag aac aag aac gct gat acc gag aac ctc att aac      336
Leu Trp Pro His Lys Asn Lys Asn Ala Asp Thr Glu Asn Leu Ile Asn
            100                 105                 110 ctc atc gat tcc gag att cag aag cag ctt aac aag gct ctt ctc gat      384
Leu Ile Asp Ser Glu Ile Gln Lys Gln Leu Asn Lys Ala Leu Leu Asp
        115                 120                 125 gct gat agg aac gag tgg tcc tct tac ctt gag tcc atc ttc gat tcc      432
Ala Asp Arg Asn Glu Trp Ser Ser Tyr Leu Glu Ser Ile Phe Asp Ser
    130                 135                 140 tcc aac aac ctc aac ggt gct att gtg gat gct cag tgg agt gga act      480
Ser Asn Asn Leu Asn Gly Ala Ile Val Asp Ala Gln Trp Ser Gly Thr
145                 150                 155                 160 gtt aac act acc aac agg acc ctt aga aac cca acc gag tcc gat tac      528
Val Asn Thr Thr Asn Arg Thr Leu Arg Asn Pro Thr Glu Ser Asp Tyr
                165                 170                 175 acc aac gtt gtg acc aac ttc att gct gct gat ggc gat att gcc aac      576
Thr Asn Val Val Thr Asn Phe Ile Ala Ala Asp Gly Asp Ile Ala Asn
            180                 185                 190 aac gag aac cac atc atg aac gga aac ttc gat gtt gct gct gct cca      624
Asn Glu Asn His Ile Met Asn Gly Asn Phe Asp Val Ala Ala Ala Pro
        195                 200                 205 tac ttc gtt att gga gct acc gct aga ttc gct gct atg caa tcc tac      672
Tyr Phe Val Ile Gly Ala Thr Ala Arg Phe Ala Ala Met Gln Ser Tyr
    210                 215                 220 atc aag ttc tgc aac gct tgg att gac aaa gtg gga ctt tcc gat gct      720
Ile Lys Phe Cys Asn Ala Trp Ile Asp Lys Val Gly Leu Ser Asp Ala
225                 230                 235                 240
```

```
caa ctt act acc cag aag gct aac ctt gat agg acc aag cag aac atg       768
Gln Leu Thr Thr Gln Lys Ala Asn Leu Asp Arg Thr Lys Gln Asn Met
            245                 250                 255 agg aac gct atc ctt aac tac acc cag cag gtt atg aag gtg ttc aag       816
Arg Asn Ala Ile Leu Asn Tyr Thr Gln Gln Val Met Lys Val Phe Lys
        260                 265                 270 gac tcc aag aac atg cca acc att ggc acc aac aag ttc tct gtg gac       864
Asp Ser Lys Asn Met Pro Thr Ile Gly Thr Asn Lys Phe Ser Val Asp
    275                 280                 285 acc tac aac gtg tac atc aag ggc atg acc ttg aac gtg ctc gat att       912
Thr Tyr Asn Val Tyr Ile Lys Gly Met Thr Leu Asn Val Leu Asp Ile
290                 295                 300 gtg gct att tgg cca tcc ctt tac cca gat gat tac acc tct cag act       960
Val Ala Ile Trp Pro Ser Leu Tyr Pro Asp Asp Tyr Thr Ser Gln Thr
305                 310                 315                 320 gct ctt gag caa act agg gtg acc ttc tct aac atg gtg ggt caa gaa      1008
Ala Leu Glu Gln Thr Arg Val Thr Phe Ser Asn Met Val Gly Gln Glu
                325                 330                 335 gaa ggt act gac gga tct ctc agg atc tac aac acc ttc gac tca ttc      1056
Glu Gly Thr Asp Gly Ser Leu Arg Ile Tyr Asn Thr Phe Asp Ser Phe
            340                 345                 350 tct tac cag cac tcc cca atc cca aac aac aac gtg aac ctc atc tcc      1104
Ser Tyr Gln His Ser Pro Ile Pro Asn Asn Asn Val Asn Leu Ile Ser
        355                 360                 365 tac tac aac gac gag ctt cag aac ctt gag ctt gga gtt tac acc cca      1152
Tyr Tyr Asn Asp Glu Leu Gln Asn Leu Glu Leu Gly Val Tyr Thr Pro
    370                 375                 380 cca aag aag gga tct gga tac tct tac cca tac ggc ttc gtg ctt aac      1200
Pro Lys Lys Gly Ser Gly Tyr Ser Tyr Pro Tyr Gly Phe Val Leu Asn
385                 390                 395                 400 tac gcc aac tcc aag tac aag tac ggc gat tct aac gat cca gag tct      1248
Tyr Ala Asn Ser Lys Tyr Lys Tyr Gly Asp Ser Asn Asp Pro Glu Ser
                405                 410                 415 ctt gga gga ctt tct acc ctt tcc gct cca att caa cag gtt aac gct      1296
Leu Gly Gly Leu Ser Thr Leu Ser Ala Pro Ile Gln Gln Val Asn Ala
            420                 425                 430 gct acc cag aac tct aag tac ctc gat ggc gag att ctt aac gga att      1344
Ala Thr Gln Asn Ser Lys Tyr Leu Asp Gly Glu Ile Leu Asn Gly Ile
        435                 440                 445 gga gct tcc ctt cca gga tat tgc act act gga tgc tct cca act gaa      1392
Gly Ala Ser Leu Pro Gly Tyr Cys Thr Thr Gly Cys Ser Pro Thr Glu
    450                 455                 460 cca cca ttc tct tgc act tct acc gct aac gga tac aag gct tct tgc      1440
Pro Pro Phe Ser Cys Thr Ser Thr Ala Asn Gly Tyr Lys Ala Ser Cys
465                 470                 475                 480 aac cca tct gac acc aac cag aag atc aac gct ctt tac cca ttc act      1488
Asn Pro Ser Asp Thr Asn Gln Lys Ile Asn Ala Leu Tyr Pro Phe Thr
                485                 490                 495 cag gct aac gtg aag gga aac acc gga aag ctt gga gtt ctt gct tct      1536
Gln Ala Asn Val Lys Gly Asn Thr Gly Lys Leu Gly Val Leu Ala Ser
            500                 505                 510 ctc gtg tcc tac gat ctc aac cca aag aac gtg ttc gga gag ctt gat      1584
Leu Val Ser Tyr Asp Leu Asn Pro Lys Asn Val Phe Gly Glu Leu Asp
        515                 520                 525 tcc gat acc aac aac gtg att ctc aag gga att cca gct gag aag ggc      1632
Ser Asp Thr Asn Asn Val Ile Leu Lys Gly Ile Pro Ala Glu Lys Gly
    530                 535                 540
```

```
                                                         -continued tat ttc cca aac aac gct agg cca acc gtt gtg aaa gag tgg att aac      1680
Tyr Phe Pro Asn Asn Ala Arg Pro Thr Val Val Lys Glu Trp Ile Asn
545                 550                 555                 560 ggc gct tct gct gtt cca ctt gat tct ggc aac acc ctt ttc atg acc      1728
Gly Ala Ser Ala Val Pro Leu Asp Ser Gly Asn Thr Leu Phe Met Thr
                565                 570                 575 gct act aac ctt act gct acc cag tac agg att agg atc aga tac gcc      1776
Ala Thr Asn Leu Thr Ala Thr Gln Tyr Arg Ile Arg Ile Arg Tyr Ala
            580                 585                 590 aac cca aac tcc aac acc caa atc gga gtt agg att acc cag aac gga      1824
Asn Pro Asn Ser Asn Thr Gln Ile Gly Val Arg Ile Thr Gln Asn Gly
        595                 600                 605 tcc ctt att tct tct tcc aac ctc acc ctt tac tct acc acc gac atg      1872
Ser Leu Ile Ser Ser Ser Asn Leu Thr Leu Tyr Ser Thr Thr Asp Met
    610                 615                 620 aac aac acc ctt cca ctt aac gtg tac gtg att gga gag aac gga aac      1920
Asn Asn Thr Leu Pro Leu Asn Val Tyr Val Ile Gly Glu Asn Gly Asn
625                 630                 635                 640 tac acc ctt cag gac ctt tac aac acc acc aac gtg ctt tct acc ggt      1968
Tyr Thr Leu Gln Asp Leu Tyr Asn Thr Thr Asn Val Leu Ser Thr Gly
                645                 650                 655 gat att acc ctc caa atc acc ggt gga gat cag aag att ttc atc gac      2016
Asp Ile Thr Leu Gln Ile Thr Gly Gly Asp Gln Lys Ile Phe Ile Asp
            660                 665                 670 agg atc gag ttc gtt cca act atg cca gtt cca ggc aac act aac aac      2064
Arg Ile Glu Phe Val Pro Thr Met Pro Val Pro Gly Asn Thr Asn Asn
        675                 680                 685 aac aac gga aac aac aat ggc aac aat aac cca cca cat cat gtg tgt      2112
Asn Asn Gly Asn Asn Asn Gly Asn Asn Asn Pro Pro His His Val Cys
    690                 695                 700 gct att gct gga act cag cag tct tgt tct gga cca cca aag ttc gag      2160
Ala Ile Ala Gly Thr Gln Gln Ser Cys Ser Gly Pro Pro Lys Phe Glu
705                 710                 715                 720 caa gtg tcc gat ctt gag aag att acc acc cag gtg tac atg ctt ttc      2208
Gln Val Ser Asp Leu Glu Lys Ile Thr Thr Gln Val Tyr Met Leu Phe
                725                 730                 735 aag tcc tcc cca tac gaa gaa ctt gct ctt gag gtg tcc tct tac cag      2256
Lys Ser Ser Pro Tyr Glu Glu Leu Ala Leu Glu Val Ser Ser Tyr Gln
            740                 745                 750 att tcc caa gtg gct ctt aag gtg atg gct ctc tcc gat gaa ctt ttc      2304
Ile Ser Gln Val Ala Leu Lys Val Met Ala Leu Ser Asp Glu Leu Phe
        755                 760                 765 tgc gaa gag aag aac gtg ctt agg aag ctt gtg aac aag gcc aag caa      2352
Cys Glu Glu Lys Asn Val Leu Arg Lys Leu Val Asn Lys Ala Lys Gln
    770                 775                 780 ctt ctt gag gct tcc aac ctt ctt gtt gga ggc aac ttc gag act act      2400
Leu Leu Glu Ala Ser Asn Leu Leu Val Gly Gly Asn Phe Glu Thr Thr
785                 790                 795                 800 cag aac tgg gtg ttg gga act aac gcc tac atc aac tac gat tcc ttc      2448
Gln Asn Trp Val Leu Gly Thr Asn Ala Tyr Ile Asn Tyr Asp Ser Phe
                805                 810                 815 ctc ttc aac ggt aac tac ctt tct ctt cag cca gct tct gga ttc ttc      2496
Leu Phe Asn Gly Asn Tyr Leu Ser Leu Gln Pro Ala Ser Gly Phe Phe
            820                 825                 830 acc tcc tac gcc tac caa aag att gat gag tcc acc ctt aag cca tac      2544
Thr Ser Tyr Ala Tyr Gln Lys Ile Asp Glu Ser Thr Leu Lys Pro Tyr
        835                 840                 845
```

```
acc agg tac aag gtg tca gga ttc att gga cag tct aac cag gtg gag    2592
Thr Arg Tyr Lys Val Ser Gly Phe Ile Gly Gln Ser Asn Gln Val Glu
    850                 855                 860 ctt atc att tcc aga tac ggc aaa gag atc gac aag atc ctc aac gtt    2640
Leu Ile Ile Ser Arg Tyr Gly Lys Glu Ile Asp Lys Ile Leu Asn Val
865                 870                 875                 880 cca tat gct gga cca ctt cca att acc gct gat gct tcc att act tgc    2688
Pro Tyr Ala Gly Pro Leu Pro Ile Thr Ala Asp Ala Ser Ile Thr Cys
                885                 890                 895 tgc gct cca gaa att gga caa tgc gac ggc gaa cag tct gat tct cac    2736
Cys Ala Pro Glu Ile Gly Gln Cys Asp Gly Glu Gln Ser Asp Ser His
            900                 905                 910 ttc ttc aac tac tcc atc gat gtg ggt gct ctt cat cca gaa ctc aac    2784
Phe Phe Asn Tyr Ser Ile Asp Val Gly Ala Leu His Pro Glu Leu Asn
        915                 920                 925 cca gga att gag atc gga ctc aag atc gtt cag tcc aac ggt tac atc    2832
Pro Gly Ile Glu Ile Gly Leu Lys Ile Val Gln Ser Asn Gly Tyr Ile
    930                 935                 940 acc att tcc aac ctc gag atc att gag gaa agg cca ctt acc gag atg    2880
Thr Ile Ser Asn Leu Glu Ile Ile Glu Glu Arg Pro Leu Thr Glu Met
945                 950                 955                 960 gaa atc cag gct gtg aat agg aag aac cag aag tgg gag agg gaa aag    2928
Glu Ile Gln Ala Val Asn Arg Lys Asn Gln Lys Trp Glu Arg Glu Lys
                965                 970                 975 ctt ctt gag tgc gct tct att tct gag ctt ctc cag cct atc atc aac    2976
Leu Leu Glu Cys Ala Ser Ile Ser Glu Leu Leu Gln Pro Ile Ile Asn
            980                 985                 990 cag att gac tcc ctc ttc aag gat  gga aac tgg tac aac  gat atc ctt   3024
Gln Ile Asp Ser Leu Phe Lys Asp  Gly Asn Trp Tyr Asn  Asp Ile Leu
        995                 1000                1005 cca cat gtg acc tac cag gac  ctc aag aac att atc  atc cca gag        3069
Pro His Val Thr Tyr Gln Asp  Leu Lys Asn Ile Ile  Ile Pro Glu
    1010                1015                 1020 ctt cca aag ctt aag cac tgg  ttc att gag aac ttg  cct ggt gag        3114
Leu Pro Lys Leu Lys His Trp  Phe Ile Glu Asn Leu  Pro Gly Glu
    1025                1030                 1035 tac cat gag atc gag cag aag  atg aag gaa gct ctc  aag tac gct        3159
Tyr His Glu Ile Glu Gln Lys  Met Lys Glu Ala Leu  Lys Tyr Ala
    1040                1045                 1050 ttc acc cag ctt gat gag aag  aac ctc att cac aac  gga cat ttc        3204
Phe Thr Gln Leu Asp Glu Lys  Asn Leu Ile His Asn  Gly His Phe
    1055                1060                 1065 acc acc aac ctc att gat tgg  caa gtt gag ggt gat  gct cag atg        3249
Thr Thr Asn Leu Ile Asp Trp  Gln Val Glu Gly Asp  Ala Gln Met
    1070                1075                 1080 aag gtg ttg gag aac gat gct  ctt gct ctt cag ctc  ttc aac tgg        3294
Lys Val Leu Glu Asn Asp Ala  Leu Ala Leu Gln Leu  Phe Asn Trp
    1085                1090                 1095 gat gct tct gct tcc cag tcc  att aac atc ctc gag  ttc gat gag        3339
Asp Ala Ser Ala Ser Gln Ser  Ile Asn Ile Leu Glu  Phe Asp Glu
    1100                1105                 1110 gat aag gct tac aag ctt agg  gtt tac gct caa gga  tct gga act        3384
Asp Lys Ala Tyr Lys Leu Arg  Val Tyr Ala Gln Gly  Ser Gly Thr
    1115                1120                 1125 atc cag ttc gga aac tgc gaa  gat gag gcc att cag  ttc aac acc        3429
Ile Gln Phe Gly Asn Cys Glu  Asp Glu Ala Ile Gln  Phe Asn Thr
    1130                1135                 1140
```

```
aac agc ttc atc tac caa gag aag atc gtg tac ttc gat acc cca        3474
Asn Ser Phe Ile Tyr Gln Glu Lys Ile Val Tyr Phe Asp Thr Pro
    1145                1150                1155 tct gtg aac ctt cac att cag tct gag gga tcc gag ttc att gtg        3519
Ser Val Asn Leu His Ile Gln Ser Glu Gly Ser Glu Phe Ile Val
    1160                1165                1170 tcc tcc atc gat ctc att gag ctt tcc gac gac cag tga                3558
Ser Ser Ile Asp Leu Ile Glu Leu Ser Asp Asp Gln
    1175                1180            1185

<210> SEQ ID NO 8
<211> LENGTH: 1185
<212> TYPE: PRT
<213> ORGANISM: Artificial Sequence
<220> FEATURE:
<223> OTHER INFORMATION: Synthetic Construct

<400> SEQUENCE: 8

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300
```

```
Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
            325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Asn Val Asn Leu Ile Ser
            355                 360                 365

Tyr Tyr Asn Asp Glu Leu Gln Asn Leu Glu Leu Gly Val Tyr Thr Pro
        370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
                420                 425                 430

Ala Thr Gln Asn Ser Lys Tyr Leu Asp Gly Glu Ile Leu Asn Gly Ile
            435                 440                 445

Gly Ala Ser Leu Pro Gly Tyr Cys Thr Gly Cys Ser Pro Thr Glu
450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
                500                 505                 510

Leu Val Ser Tyr Asp Leu Asn Pro Lys Asn Val Phe Gly Glu Leu Asp
            515                 520                 525

Ser Asp Thr Asn Asn Val Ile Leu Lys Gly Ile Pro Ala Glu Lys Gly
        530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
                660                 665                 670

Arg Ile Glu Phe Val Pro Thr Met Pro Val Pro Gly Asn Thr Asn Asn
            675                 680                 685

Asn Asn Gly Asn Asn Asn Gly Asn Asn Asn Pro Pro His His Val Cys
            690                 695                 700

Ala Ile Ala Gly Thr Gln Gln Ser Cys Ser Gly Pro Pro Lys Phe Glu
705                 710                 715                 720
```

```
Gln Val Ser Asp Leu Glu Lys Ile Thr Thr Gln Val Tyr Met Leu Phe
                725                 730                 735

Lys Ser Ser Pro Tyr Glu Glu Leu Ala Leu Glu Val Ser Tyr Gln
        740                 745                 750

Ile Ser Gln Val Ala Leu Lys Val Met Ala Leu Ser Asp Glu Leu Phe
            755                 760                 765

Cys Glu Glu Lys Asn Val Leu Arg Lys Leu Val Asn Lys Ala Lys Gln
        770                 775                 780

Leu Leu Glu Ala Ser Asn Leu Val Gly Asn Phe Glu Thr Thr
785                 790                 795                 800

Gln Asn Trp Val Leu Gly Thr Asn Ala Tyr Ile Asn Tyr Asp Ser Phe
            805                 810                 815

Leu Phe Asn Gly Asn Tyr Leu Ser Leu Gln Pro Ala Ser Gly Phe Phe
            820                 825                 830

Thr Ser Tyr Ala Tyr Gln Lys Ile Asp Glu Ser Thr Leu Lys Pro Tyr
            835                 840                 845

Thr Arg Tyr Lys Val Ser Gly Phe Ile Gly Gln Ser Asn Gln Val Glu
        850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
            885                 890                 895

Cys Ala Pro Glu Ile Gly Gln Cys Asp Gly Gln Ser Asp Ser His
            900                 905                 910

Phe Phe Asn Tyr Ser Ile Asp Val Gly Ala Leu His Pro Glu Leu Asn
            915                 920                 925

Pro Gly Ile Glu Ile Gly Leu Lys Ile Val Gln Ser Asn Gly Tyr Ile
            930                 935                 940

Thr Ile Ser Asn Leu Glu Ile Ile Glu Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
            980                 985                 990

Gln Ile Asp Ser Leu Phe Lys Asp Gly Asn Trp Tyr Asn Asp Ile Leu
        995                 1000                1005

Pro His Val Thr Tyr Gln Asp Leu Lys Asn Ile Ile Pro Glu
    1010                1015                1020

Leu Pro Lys Leu Lys His Trp Phe Ile Glu Asn Leu Pro Gly Glu
    1025                1030                1035

Tyr His Glu Ile Glu Gln Lys Met Lys Glu Ala Leu Lys Tyr Ala
    1040                1045                1050

Phe Thr Gln Leu Asp Glu Lys Asn Leu Ile His Asn Gly His Phe
    1055                1060                1065

Thr Thr Asn Leu Ile Asp Trp Gln Val Glu Gly Asp Ala Gln Met
    1070                1075                1080

Lys Val Leu Glu Asn Asp Ala Leu Ala Leu Gln Leu Phe Asn Trp
    1085                1090                1095

Asp Ala Ser Ala Ser Gln Ser Ile Asn Ile Leu Glu Phe Asp Glu
    1100                1105                1110

Asp Lys Ala Tyr Lys Leu Arg Val Tyr Ala Gln Gly Ser Gly Thr
    1115                1120                1125
```

```
Ile Gln  Phe Gly Asn Cys Glu  Asp Glu Ala Ile Gln  Phe Asn Thr
    1130             1135                1140

Asn Ser  Phe Ile Tyr Gln Glu  Lys Ile Val Tyr Phe  Asp Thr Pro
    1145             1150                1155

Ser Val  Asn Leu His Ile Gln  Ser Glu Gly Ser Glu  Phe Ile Val
    1160             1165                1170

Ser Ser  Ile Asp Leu Ile Glu  Leu Ser Asp Asp Gln
    1175             1180                1185

<210> SEQ ID NO 9
<211> LENGTH: 1077
<212> TYPE: DNA
<213> ORGANISM: Artificial Sequence
<220> FEATURE:
<223> OTHER INFORMATION: hppdPf-4Pa coding sequence
<220> FEATURE:
<221> NAME/KEY: CDS
<222> LOCATION: (1)..(1077)

<400> SEQUENCE: 9 atg gca gat tta tat gaa aac cca atg gga ctc atg ggc ttc gag ttt         48
Met Ala Asp Leu Tyr Glu Asn Pro Met Gly Leu Met Gly Phe Glu Phe
1               5                   10                  15 att gag ttt gct tct cct act cct gga act ctt gaa cct atc ttc gaa         96
Ile Glu Phe Ala Ser Pro Thr Pro Gly Thr Leu Glu Pro Ile Phe Glu
                20                  25                  30 ata atg ggt ttt aca aag gtc gct acc cac agg tct aag aac gtt cat        144
Ile Met Gly Phe Thr Lys Val Ala Thr His Arg Ser Lys Asn Val His
            35                  40                  45 ctg tac aga caa gga gag ata aat cta atc ctg aac aat gag cca aac        192
Leu Tyr Arg Gln Gly Glu Ile Asn Leu Ile Leu Asn Asn Glu Pro Asn
        50                  55                  60 agc att gct tcc tac ttt gcc gct gaa cat ggt cca tca gtg tgt gga        240
Ser Ile Ala Ser Tyr Phe Ala Ala Glu His Gly Pro Ser Val Cys Gly
65                  70                  75                  80 atg gcc ttt agg gtt aaa gat agc cag aag gca tat aat cgt gct ttg        288
Met Ala Phe Arg Val Lys Asp Ser Gln Lys Ala Tyr Asn Arg Ala Leu
                85                  90                  95 gaa ctg gga gcc caa cca att cac att gat act ggg cca atg gaa ctt        336
Glu Leu Gly Ala Gln Pro Ile His Ile Asp Thr Gly Pro Met Glu Leu
            100                 105                 110 aac ctt cca gcc ata aag gga att gga ggt gct cct ttg tat ctt att        384
Asn Leu Pro Ala Ile Lys Gly Ile Gly Gly Ala Pro Leu Tyr Leu Ile
        115                 120                 125 gac cgc ttc gga gag ggc tct tcc att tac gat atc gac ttc gtt tac        432
Asp Arg Phe Gly Glu Gly Ser Ser Ile Tyr Asp Ile Asp Phe Val Tyr
    130                 135                 140 ttg gaa ggt gtc gaa cgc aat cca gtt gga gct ggt ttg aaa gtg atc        480
Leu Glu Gly Val Glu Arg Asn Pro Val Gly Ala Gly Leu Lys Val Ile
145                 150                 155                 160 gat cac ctt acc cac aat gta tat aga gga agg atg gtg tat tgg gct        528
Asp His Leu Thr His Asn Val Tyr Arg Gly Arg Met Val Tyr Trp Ala
                165                 170                 175 aac ttc tat gag aaa ctc ttc aac ttt aga gag gca agg tat ttc gac        576
Asn Phe Tyr Glu Lys Leu Phe Asn Phe Arg Glu Ala Arg Tyr Phe Asp
            180                 185                 190 att aag gga gaa tac aca ggt cta act tct aaa gct atg tca gca cca        624
Ile Lys Gly Glu Tyr Thr Gly Leu Thr Ser Lys Ala Met Ser Ala Pro
        195                 200                 205
```

```
gac gga atg att agg att cct ctt aat gag gaa agt tct aag ggt gct        672
Asp Gly Met Ile Arg Ile Pro Leu Asn Glu Glu Ser Ser Lys Gly Ala
    210                 215                 220 gga caa atc gaa gag ttc ctt atg cag ttt aac ggt gag gga atc caa        720
Gly Gln Ile Glu Glu Phe Leu Met Gln Phe Asn Gly Glu Gly Ile Gln
225                 230                 235                 240 cac gtt gct ttt ttg aca gac gat ctt gtc aag act tgg gat gct ctg        768
His Val Ala Phe Leu Thr Asp Asp Leu Val Lys Thr Trp Asp Ala Leu
                245                 250                 255 aag aaa att gga atg agg ttt atg act gca cct ccc gat acc tat tac        816
Lys Lys Ile Gly Met Arg Phe Met Thr Ala Pro Pro Asp Thr Tyr Tyr
                    260                 265                 270 gaa atg ctc gaa gga cga ctt cca gat cac ggt gaa ccc gtt gac cag        864
Glu Met Leu Glu Gly Arg Leu Pro Asp His Gly Glu Pro Val Asp Gln
                275                 280                 285 ctc caa gct aga ggt ata cta ctt gat gga agt tct gtg gaa gga gat        912
Leu Gln Ala Arg Gly Ile Leu Leu Asp Gly Ser Ser Val Glu Gly Asp
            290                 295                 300 aag agg ttg ctt ctg cag att ttt tcc gag aca cta atg ggt cca gtt        960
Lys Arg Leu Leu Leu Gln Ile Phe Ser Glu Thr Leu Met Gly Pro Val
305                 310                 315                 320 ttc ttt gag ttt att cag cgt aaa gga gat gac ggc ttt ggc cca tgg       1008
Phe Phe Glu Phe Ile Gln Arg Lys Gly Asp Asp Gly Phe Gly Pro Trp
                    325                 330                 335 aac ttt gcg caa ctt ttc gaa agt att gag cgt gac caa gtt cgt aga       1056
Asn Phe Ala Gln Leu Phe Glu Ser Ile Glu Arg Asp Gln Val Arg Arg
                340                 345                 350 ggt gtt ctt act gct gat tga                                           1077
Gly Val Leu Thr Ala Asp
            355

<210> SEQ ID NO 10
<211> LENGTH: 358
<212> TYPE: PRT
<213> ORGANISM: Artificial Sequence
<220> FEATURE:
<223> OTHER INFORMATION: Synthetic Construct

<400> SEQUENCE: 10

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140
```

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Ala Gln Leu Phe Glu Ser Ile Glu Arg Asp Gln Val Arg Arg
            340                 345                 350

Gly Val Leu Thr Ala Asp
        355

<210> SEQ ID NO 11
<211> LENGTH: 8068
<212> TYPE: DNA
<213> ORGANISM: Artificial Sequence
<220> FEATURE:
<223> OTHER INFORMATION: transformation plasmid pSZ8832 - sequence
      between T-DNA borders
<220> FEATURE:
<221> NAME/KEY: misc_feature
<222> LOCATION: (1)..(130)
<223> OTHER INFORMATION: polylinker
<220> FEATURE:
<221> NAME/KEY: misc_feature
<222> LOCATION: (131)..(400)
<223> OTHER INFORMATION: 3' untranslated region of 35S transcript
      (counter clockwise)
<220> FEATURE:
<221> NAME/KEY: misc_feature
<222> LOCATION: (401)..(411)
<223> OTHER INFORMATION: polylinker
<220> FEATURE:
<221> NAME/KEY: misc_feature
<222> LOCATION: (412)..(3969)
<223> OTHER INFORMATION: cry14Ab-1.b coding sequence (counter clockwise)
<220> FEATURE:
<221> NAME/KEY: misc_feature
<222> LOCATION: (3970)..(5276)
<223> OTHER INFORMATION: ubiquitin-10 promoter (counter clockwise)
<220> FEATURE:
<221> NAME/KEY: misc_feature
<222> LOCATION: (5277)..(5381)
<223> OTHER INFORMATION: polylinker
<220> FEATURE:
<221> NAME/KEY: misc_feature
<222> LOCATION: (5382)..(5576)

<223> OTHER INFORMATION: 3' untranslated region 35S transcript (counter
      clockwise)
<220> FEATURE:
<221> NAME/KEY: misc_feature
<222> LOCATION: (5577)..(5588)
<223> OTHER INFORMATION: polylinker
<220> FEATURE:
<221> NAME/KEY: misc_feature
<222> LOCATION: (5589)..(6665)
<223> OTHER INFORMATION: hppdPf-4Pa coding sequence (counter clockwise)
<220> FEATURE:
<221> NAME/KEY: misc_feature
<222> LOCATION: (6666)..(7037)
<223> OTHER INFORMATION: TPotpY-1Pf optimized transit peptide (counter
      clockwise)
<220> FEATURE:
<221> NAME/KEY: misc_feature
<222> LOCATION: (7038)..(7058)
<223> OTHER INFORMATION: polylinker
<220> FEATURE:
<221> NAME/KEY: misc_feature
<222> LOCATION: (7059)..(7185)
<223> OTHER INFORMATION: Tobacco Etch Virus genomic RNA leader sequence
      (counter clockwise)
<220> FEATURE:
<221> NAME/KEY: misc_feature
<222> LOCATION: (7186)..(7191)
<223> OTHER INFORMATION: polylinker sequence
<220> FEATURE:
<221> NAME/KEY: misc_feature
<222> LOCATION: (7192)..(7941)
<223> OTHER INFORMATION: double enhanced promoter region of CaMV 35S
      transcript (counter clockwise)
<220> FEATURE:
<221> NAME/KEY: misc_feature
<222> LOCATION: (7942)..(8068)
<223> OTHER INFORMATION: polylinker sequence

<400> SEQUENCE: 11
gtactgggcc cttgtggcgc tctatcatag ctataaacct attcagcaca atgggctcga      60
gggcgatcgc tacgggaact cgagaaggat ccttaagctt ctagttctag agcggccgct     120
cgaggaattc tggattttag tactggattt tggttttagg aattagaaat tttattgata     180
gaagtatttt acaaatacaa atacatacta agggtttctt atatgctcaa cacgtgagcg     240
aaaccctata agaaccctaa ttcccttatc tgggaactac tcacacatta ttatggagaa     300
aatagagaga gatagatttg tagagagaga ctggtgattt cagcgtgtcc tctccaaatg     360
aaatgaactt cctatatag aggaagggtc ttgcgaagga ggcgcgcctc atcactggtc      420
gtcggaaagc tcaatgagat cgatggagga cacaatgaac tcggatccct cagactgaat     480
gtgaaggttc acagatgggg tatcgaagta cacgatcttc tcttggtaga tgaagctgtt     540
ggtgttgaac tgaatggcct catcttcgca gtttccgaac tggatagttc cagatccttg     600
agcgtaaacc ctaagcttgt aagccttatc ctcatcgaac tcgaggatgt taatggactg     660
ggaagcagaa gcatcccagt tgaagagctg aagagcaaga gcatcgttct ccaacacctt     720
catctgagca tcaccctcaa cttgccaatc aatgaggttg gtggtgaaat gtccgttgtg     780
aatgaggttc ttctcatcaa gctgggtgaa agcgtacttg agagcttcct tcatcttctg     840
ctcgatctca tggtactcac caggcaagtt ctcaatgaac cagtgcttaa gctttggaag     900
ctctgggatg ataatgttct tgaggtcctg gtaggtcaca tgtggaagga tatcgttgta     960
ccagtttcca tccttgaaga gggagtcaat ctggttgatg ataggctgga gaagctcaga    1020
aatagaagcg cactcaagaa gcttttccct ctcccacttc tggttcttcc tattcacagc    1080 ctggattttcc atctcggtaa gtggcctttc tcaatgatc tcgaggttgg aaatggtgat    1140
gtaaccgttg gactgaacga tcttgagtcc gatctcaatt cctgggttga gttctggatg    1200

```
aagagcaccc acatcgatgg agtagttgaa gaagtgagaa tcagactgtt cgccgtcgca    1260
ttgtccaatt tctggagcgc agcaagtaat ggaagcatca gcggtaattg gaagtggtcc    1320
agcatatgga acgttgagga tcttgtcgat ctctttgccg tatctggaaa tgataagctc    1380
cacctggtta gactgtccaa tgaatcctga caccttgtac ctggtgtatg cttaagggt     1440 ggactcatca atcttttggt aggcgtagga ggtgaagaat ccagaagctg gctgaagaga    1500
aaggtagtta ccgttgaaga ggaaggaatc gtagttgatg taggcgttag ttcccaacac    1560
ccagttctga gtagtctcga agttgcctcc aacaagaagg ttggaagcct caagaagttg    1620
cttggccttg ttcacaagct tcctaagcac gttcttctct tcgcagaaaa gttcatcgga    1680
gagagccatc accttaagag ccacttggga aatctggtaa aggacaccct caagagcaag    1740
ttcttcgtat ggggaggact tgaaaagcat gtacacctgg tggtaatct  tctcaagatc    1800 ggacacttgc tcgaactttg gtggtccaga acaagactgc tgagttccag caatagcaca    1860
cacatgatgt ggtgggttat tgttgccatt gttgtttccg ttgttgttgt tagtgttgcc    1920
tggaactggc atagttggaa cgaactcgat cctgtcgatg aaaatcttct gatctccacc    1980
ggtgatttgg agggtaatat caccggtaga aagcacgttg gtggtgttgt aaaggtcctg    2040
aagggtgtag tttccgttct ctccaatcac gtacacgtta agtggaaggg tgttgttcat    2100
gtcggtggta gagtaaaggg tgaggttgga agaagaaata agggatccgt tctgggtaat    2160
cctaactccg atttgggtgt tggagtttgg gttggcgtat ctgatcctaa tcctgtactg    2220
ggtagcagta aggttagtag cggtcatgaa aagggtgttg ccagaatcaa gtggaacagc    2280
agaagcgccg ttaatccact cttcacaac  ggttggccta gcgttgtttg ggaaatagcc    2340
cttctcagct ggaattccct tgagaatcac gttgttggta tcggaatcaa gctctccgaa    2400
cacgttcttt gggttgagat cgtaggacac gagagaagca agaactccaa gctttccggt    2460
gtttcccttc acgttagcct gagtgaatgg gtaaagagcg ttgatcttct ggttggtgtc    2520
agatgggttg caagaagcct tgtatccgtt agcggtagaa gtgcaagaga atggtggttc    2580
agttggagag catccagtag tgcaatatcc tggaagggaa gctccaattc cgttaagaat    2640
ctcgccatcg aggtacttag agttctgggt agcagcgtta acctgttgaa ttggagcgga    2700
aagggtagaa agtcctccaa gagactctgg atcgttagaa tcgccgtact tgtacttgga    2760
gttggcgtag ttaagcacga agccgtatgg gtaagagtat ccagatccct tctttggtgg    2820
ggtgtaaact ccaagctcaa ggttctgaag ctcgtcgttg tagtaggaga tgaggttcac    2880
gttgttgttt gggattgggg agtgctggta agagaatgag tcgaaggtgt tgtagatcct    2940
gagagatccg tcagtacctt cttcttgacc caccatgtta gagaaggtca ccctagtttg    3000
ctcaagagca gtctgagagg tgtaatcatc tgggtaaagg gatggccaaa tagccacaat    3060
atcgagcacg ttcaaggtca tgcccttgat gtacacgttg taggtgtcca cagagaactt    3120
gttggtgcca atggttggca tgttcttgga gtccttgaac accttcataa cctgctgggt    3180
gtagttaagg atagcgttcc tcatgttctg cttggtccta tcaaggttag ccttctgggt    3240
agtaagttga gcatcggaaa gtcccacttt gtcaatccaa gcgttgcaga acttgatgta    3300
ggattgcata gcagcgaatc tagcggtagc tccaataacg aagtatggag cagcagcaac    3360
atcgaagttt ccgttcatga tgtggttctc gttgttggca atatcgccat cagcagcaat    3420
gaagttggtc acaacgttgg tgtaatcgga ctcggttggg tttctaaggg tcctgttggt    3480
agtgttaaca gttccactcc actgagcatc cacaatagca ccgttgaggt tgttggagga    3540
```

```
atcgaagatg gactcaaggt aagaggacca ctcgttccta tcagcatcga gaagagcctt    3600
gttaagctgc ttctgaatct cggaatcgat gaggttaatg aggttctcgg tatcagcgtt    3660
cttgttcttg tgtggccaaa gccatccaat caccatgttg atgattggag ccacgaaagt    3720
tccacctgga acgaaggatc cagcaagaga aattccagac tggagaaggg taaggtagtt    3780
gaaggttcca ccttgagaag cagagaatcc ctgttggaga gcagtaagag agaaagatcc    3840
ggtcttttgg aactcttccc aagccttctt aagatcaccc acggtatcag taagggagtt    3900
cacgttagaa actggaatag cgagcacgtt gtatggaatg ttctgctggg actgaaggtt    3960
gcaatccatc tgttaatcag aaaaactcag attaatcgac aaattcgatc gcacaaacta    4020
gaaactaaca cctgatctag atagaaatca caaatcgaag agtaattatt cgacaaaact    4080
caaattattt gaacaaatcg gatgatatct atgaaaccct aatcgagaat taagatgata    4140
tctaacgatc aaacccagaa aatcgtcttc gatctaagat taacagaatc taaaccaaag    4200
aacatatacg aaattgggat cgaacgaaaa caaaatcgaa gattttgaga gaataaggaa    4260
cacagaaatt taccttgatc acggtagaga gaattgagag aaagttttta agattttgag    4320
aaattgaaat ctgaattgtg aagaagaaga gctctttggg tattgtttta tagaagaaga    4380
agaagaaaag acgaggacga ctaggtcacg agaaagctaa ggcggtgaag caatagctaa    4440
taataaaatg acacgtgtat tgagcgttgt ttacacgcaa agttgttttt ggctaattgc    4500
cttattttta ggttgaggaa aagtatttgt gctttgagtt gataaacacg actcgtgtgt    4560
gccggctgca accactttga cgccgtttat tactgactcg tcgacaacca caatttctaa    4620
cggtcgtcat aagatccagc cgttgagatt taacgatcgt tacgatttat atttttttag    4680
cattatcgtt ttattttta aatatacggt ggagctgaaa attggcaata attgaaccgt    4740
gggtcccact gcattgaagc gtatttcgta ttttctagaa ttcttcgtgc tttatttctt    4800 ttccttttg tttttttttg ccatttatct aatgcaagtg ggcttataaa atcagtgaat    4860
ttcttggaaa agtaacttct ttatcgtata acatattgtg aaattatcca tttcttttaa    4920 tttttagtg ttattggata tttttgtatg attattgatt tgcataggat aatgacttt    4980 gtatcaagtt ggtgaacaag tctcgttaaa aaaggcaagt ggtttggtga ctcgatttat    5040
tcttgttatt taattcatat atcaatggat cttatttggg gcctggtcca tatttaacac    5100
tcgtgttcag tccaatgacc aataatattt tttcattaat aacaatgtaa caagaatgat    5160
acacaaaaca ttctttgaat aagttcgcta tgaagaaggg aacttatccg gtcctagatc    5220
atcagttcat acaaacctcc atagagttca acatcttaaa caagaatatc ctgatcccca    5280
aacaatgatt aatagatcta agtcgacact aagctttaac tagtttaggc ctaatgaatt    5340
ccaggatcca tactcgagat acccgggcct gcaggcctag gactggattt tggttttagg    5400
aattagaaat tttattgata gaagtatttt acaaatacaa atacatacta agggtttctt    5460
atatgctcaa cacatgagcg aaaccctata agaaccctaa ttcccttatc tgggaactac    5520
tcacacatta ttatagagag agatagattt gtagagagag actggtgatt cagcggacg    5580 tcgttaactc aatcagcagt aagaacacct ctacgaactt ggtcacgctc aatactttcg    5640
aaaagttgcg caaagttcca tgggccaaag ccgtcatctc ctttacgctg aataaactca    5700
aagaaaactg gacccattag tgtctcggaa aaaatctgca gaagcaacct cttatctcct    5760
tccacagaac ttccatcaag tagtatacct ctagctggga ctggtcaacg gggttcaccg    5820
tgatctggaa gtcgtccttc gagcatttcg taataggtat cggaggtgc agtcataaac    5880 ctcattccaa ttttcttcag agcatcccaa gtcttgacaa gatcgtctgt caaaaaagca    5940
```

```
acgtgttgga ttccctcacc gttaaactgc ataaggaact cttcgatttg tccagcaccc      6000
ttagaacttt cctcattaag aggaatccta atcattccgt ctggtgctga catagcttta      6060
gaagttagac ctgtgtattc tcccttaatg tcgaaatacc ttgcctctct aaagttgaag      6120
agtttctcat agaagttagc ccaatacacc atccttcctc tatatacatt gtgggtaagg      6180
tgatcgatca ctttcaaacc agctccaact ggattgcgtt cgacaccttc aagtaaacg       6240 aagtcgatat cgtaaatgga agagccctct ccgaagcgt caataagata caaggagca        6300 cctccaattc cctttatggc tggaaggtta agttccattg cccagtatc aatgtgaatt       6360 ggttgggctc ccagttccaa agcacgatta tatgccttct ggctatcttt aaccctaaag     6420
gccattccac acactgatgg accatgttca gcggcaaagt aggaagcaat gctgtttggc      6480
tcattgttca ggattagatt tatctctcct tgtctgtaca gatgaacgtt cttagacctg      6540
tgggtagcga cctttgtaaa acccattatt tcgaagatag gttcaagagt tccaggagta     6600
ggagaagcaa actcaataaa ctcgaagccc atgagtccca tgggttttc atataaatct       6660 gccatgcacc ggatccttcc gccgttgctg acgttgccga ggcttctgga ggagcggcgg      6720
gcgacgggga ggctggcggt ggacttgagc ccctggaacg gagcgacggc ggtggccgac      6780
gaggccatca tcacggtggg cgccatagac agcggcggca ggtacgacag cgtctcgaac      6840
ttcttgttgc cgtaggccgg ccacacctgc atatattgaa ctcttccacc gttgctggga     6900
agggtggaga agtcgttagc cttcttggtg gtggggaagg cggcgttgga cttaaggccg      6960
gtgaacggag ccaccatgtt ggcctgagca ggggcggtcc ggctaacggt cgcaactgag      7020
gaggagatcg aagccatttt tttttaatt aacacgtgcg ttcgtaaatg gtgaaatttt       7080
tcagaaaatt gcttttgctt taaagaaat gatttaaatt gctgcaatag aagtagaatg        7140
cttgattgct tgagattcgt ttgttttgta tatgttgtgt tgagaattta ttgtcctctc      7200
caaatgaaat gaacttcctt atatagagga agggtcttgc gaaggatagt gggattgtgc      7260
gtcatcccct acgtcagtgg agatatcaca tcaatccact tgctttgaag acgtggttgg      7320
aacgtcttct ttttccacga tgctcctcgt gggtgggggt ccatcttt gg gaccactgtc     7380 ggtagaggca tcttgaacga tagccttttcc tttatcgcaa tgatggcatt tgtaggagcc     7440
accttccttt tccactatct tcacaataaa gtgacagata gctgggcaat ggaatccgag      7500
gaggtttccg gatattaccc tttgttgaaa agtctcaatt gcccttttggt cttctgagac    7560 tgtatctttg atatttttgg agtagacaag tgtgtcgtgc tccaccagtt atcacatcaa      7620
tccacttgct ttgaagacgt ggttggaacg tcttctttt ccacgatgct cctcgtgggt       7680 ggggggtccat ctttgggacc actgtcggca gaggcatctt caacgatggc ctttccttta    7740
tcgcaatgat ggcatttgta ggagccacct tccttttcca ctatcttcac aataaagtga     7800
cagatagctg gcaatggaa tccgaggagg tttccggata ttacccttttg ttgaaaagtc    7860 tcaattgccc tttggtcttc tgagactgta tctttgatat ttttggagta gacaagtgtg     7920
tcgtgctcca ccagttgact attcgctacc ttaggaccgt tatagttacg cccgggttag     7980
ttagttagcg agcggcgaac taataactcc gctctaccga aagttacgat aaacggtcgg     8040
gtgcggagaa agaggtaatg aaatggca                                         8068

<210> SEQ ID NO 12
<211> LENGTH: 22
<212> TYPE: DNA
<213> ORGANISM: Artificial Sequence
<220> FEATURE:
```

```
<223> OTHER INFORMATION: primer PRIM1038

<400> SEQUENCE: 12
gagccacctt cctttccac ta                                         22

<210> SEQ ID NO 13
<211> LENGTH: 28
<212> TYPE: DNA
<213> ORGANISM: Artificial Sequence
<220> FEATURE:
<223> OTHER INFORMATION: primer PRIM1039

<400> SEQUENCE: 13
atagggttac tgcttcgtaa aataagca                                  28

<210> SEQ ID NO 14
<211> LENGTH: 24
<212> TYPE: DNA
<213> ORGANISM: Artificial Sequence
<220> FEATURE:
<223> OTHER INFORMATION: probe TM1788

<400> SEQUENCE: 14
cgcgtccatg atgctgcgac tatg                                      24

<210> SEQ ID NO 15
<211> LENGTH: 20
<212> TYPE: DNA
<213> ORGANISM: Artificial Sequence
<220> FEATURE:
<223> OTHER INFORMATION: primer KVM164

<400> SEQUENCE: 15
ctttctcgca ccaattgaca                                           20

<210> SEQ ID NO 16
<211> LENGTH: 20
<212> TYPE: DNA
<213> ORGANISM: Artificial Sequence
<220> FEATURE:
<223> OTHER INFORMATION: primer KVM165

<400> SEQUENCE: 16
tcaaactcaa cagcgacgac                                           20

<210> SEQ ID NO 17
<211> LENGTH: 26
<212> TYPE: DNA
<213> ORGANISM: Artificial Sequence
<220> FEATURE:
<223> OTHER INFORMATION: probe TM1242

<400> SEQUENCE: 17
ccacaaacac atgcaggtta tcttgg                                    26

<210> SEQ ID NO 18
<211> LENGTH: 30
<212> TYPE: DNA
<213> ORGANISM: Artificial Sequence
<220> FEATURE:
<223> OTHER INFORMATION: primer PRIM1041

<400> SEQUENCE: 18
cattgtgctg aataggttta tagctatgat                                30
```

```
<210> SEQ ID NO 19
<211> LENGTH: 25
<212> TYPE: DNA
<213> ORGANISM: Artificial Sequence
<220> FEATURE:
<223> OTHER INFORMATION: primer PRIM1040

<400> SEQUENCE: 19
tcaaatcaac atgggtgact agaaa                                          25

<210> SEQ ID NO 20
<211> LENGTH: 23
<212> TYPE: DNA
<213> ORGANISM: Artificial Sequence
<220> FEATURE:
<223> OTHER INFORMATION: probe TM1789

<400> SEQUENCE: 20
cagtactggg cccttgtggc gct                                            23

<210> SEQ ID NO 21
<211> LENGTH: 25
<212> TYPE: DNA
<213> ORGANISM: Artificial Sequence
<220> FEATURE:
<223> OTHER INFORMATION: primer PRIM1629

<400> SEQUENCE: 21
ttggtgaaaa acaatttggt gtaca                                          25

<210> SEQ ID NO 22
<211> LENGTH: 20
<212> TYPE: DNA
<213> ORGANISM: Artificial Sequence
<220> FEATURE:
<223> OTHER INFORMATION: probe TM2083

<400> SEQUENCE: 22
aatcaaatcg acatcaatgt                                                20

<210> SEQ ID NO 23
<211> LENGTH: 9663
<212> TYPE: DNA
<213> ORGANISM: Artificial Sequence
<220> FEATURE:
<223> OTHER INFORMATION: soybean event EE-GM5
<220> FEATURE:
<221> NAME/KEY: misc_feature
<222> LOCATION: (1)..(1113)
<223> OTHER INFORMATION: part of T-DNA 5' flanking region
<220> FEATURE:
<221> NAME/KEY: misc_feature
<222> LOCATION: (1114)..(8572)
<223> OTHER INFORMATION: inserted T-DNA region
<220> FEATURE:
<221> NAME/KEY: misc_feature
<222> LOCATION: (8573)..(9663)
<223> OTHER INFORMATION: part of 3' flanking region

<400> SEQUENCE: 23
cattcttata gacttatagt tttcatagat aatactacta cacacttaat tataaaatcg    60
atcacgagaa cctcacccct ttttttcagcc cactcctcac ttttttctca tgctccacac  120
acaaatcacg ataacctcac cttttgtttt catcactgat cctcacataa atcttttcac  180
attgttaaaa aaacagaaaa ataaaataaa ataaggacaa caagtatata aacgtgtaaa  240
gaagaagaag agaggaacaa aaactttatat gatatattc taatttttaa ctcagctttt  300
```

| | |
|---|---|
| acacactttg aactgttaca acaatagctt aaatagagaa attaacaagt ccctaattgg | 360 |
| ctgaaactta aagctaatct aaaataggca tcattaacaa atatctacaa attatttttt | 420 |
| ctggacacaa tcaaccttt aacaaactta tatcataaaa tctgtagaga tatataaata | 480 |
| ttttaacatg atagcaggaa aaatctcaac tgccaactca tatactcaaa aaccataaa | 540 |
| tataatcgtt cacttttctc acaacaacca catacattat acatatagag gacagtttag | 600 |
| aaatgttgat gacacaccat catttgctta acttttcaaa atcaaattaa agtaatttta | 660 |
| aggatgtatt tgtcaacaaa ttatacattc aaaagataaa aataattatt tattctttag | 720 |
| ttaattctaa ttaaatattc taaaaaagat cgaaaggggt atatagtaat ccataaatct | 780 |
| tctaagagta ttttcattat attattggct aaatatatta tttatcttaa atttatgagt | 840 |
| tttataatga caataatatt aaaaaaaatt acataaaaat ttactctaat gttaaaatta | 900 |
| ctaaataaat acttagctta agttttatta aattttaaat tgaaaaaaaa attataataa | 960 |
| tcaattaagt aattcactca agaaacacat taatcaaata atcaattcta ataggaaaaa | 1020 |
| aatatttaaa tagcactgtt taactttaaa taactcattt gagatgatat gatgattcag | 1080 |
| agtcaaatca acatgggtga ctagaaaaaa tcagtactgg gcccttgtgg cgctctatca | 1140 |
| tagctataaa cctattcagc acaatgggct cgagggcgat cgctacggga actcgagaag | 1200 |
| gatccttaag cttctagttc tagagcggcc gctcgaggaa ttctggattt tagtactgga | 1260 |
| ttttggtttt aggaattaga aatttttattg atagaagtat tttacaaata caaatacata | 1320 |
| ctaagggttt cttatatgct caacacgtga gcgaaaccct ataagaaccc taattcccct | 1380 |
| atctgggaac tactcacaca ttattatgga gaaaatagag agagatagat ttgtagagag | 1440 |
| agactggtga tttcagcgtg tcctctccaa atgaaatgaa cttccttata tagaggaagg | 1500 |
| gtcttgcgaa ggaggcgcgc ctcatcactg gtcgtcggaa agctcaatga gatcgatgga | 1560 |
| ggacacaatg aactcggatc cctcagactg aatgtgaagg ttcacagatg gggtatcgaa | 1620 |
| gtacacgatc ttctcttggt agatgaagct gttggtgttg aactgaatgg cctcatcttc | 1680 |
| gcagtttccg aactggatag ttccagatcc ttgagcgtaa accctaagct tgtaagcctt | 1740 |
| atcctcatcg aactcgagga tgttaatgga ctgggaagca gaagcatccc agttgaagag | 1800 |
| ctgaagagca agagcatcgt tctccaacac cttcatctga gcatcaccct caacttgcca | 1860 |
| atcaatgagg ttggtggtga atgtccgtt gtgaatgagg ttcttctcat caagctgggt | 1920 |
| gaaagcgtac ttgagagctt ccttcatctt ctgctcgatc tcatggtact caccaggcaa | 1980 |
| gttctcaatg aaccagtgct taagctttgg aagctctggg atgataatgt tcttgaggtc | 2040 |
| ctggtaggtc acatgtggaa ggatatcgtt gtaccagttt ccatccttga agagggagtc | 2100 |
| aatctggttg atgataggct ggagaagctc agaaatagaa gcgcactcaa gaagcttttc | 2160 |
| cctctcccac ttctggttct tcctattcac agcctggatt tccatctcgg taagtggcct | 2220 |
| ttcctcaatg atctcgaggt tggaaatggt gatgtaaccg ttggactgaa cgatcttgag | 2280 |
| tccgatctca attcctgggt tgagttctgg atgaagagca cccacatcga tggagtagtt | 2340 |
| gaagaagtga gaatcagact gttcgccgtc gcattgtcca atttctggag cgcagcaagt | 2400 |
| aatggaagca tcagcggtaa ttggaagtgg tccagcatat ggaacgttga ggatcttgtc | 2460 |
| gatctctttg ccgtatctgg aaatgataag ctccacctgg ttagactgtc caatgaatcc | 2520 |
| tgacaccttg tacctggtgt atggcttaag ggtggactca tcaatctttt ggtaggcgta | 2580 |
| ggaggtgaag aatccagaag ctggctgaag agaaaggtag ttaccgttga agaggaagga | 2640 |
| atcgtagttg atgtaggcgt tagttcccaa cacccagttc tgagtagtct cgaagttgcc | 2700 |

```
tccaacaaga aggttggaag cctcaagaag ttgcttggcc ttgttcacaa gcttcctaag    2760
cacgttcttc tcttcgcaga aaagttcatc ggagagagcc atcaccttaa gagccacttg    2820
ggaaatctgg taagaggaca cctcaagagc aagttcttcg tatggggagg acttgaaaag    2880
catgtacacc tgggtggtaa tcttctcaag atcggacact tgctcgaact ttggtggtcc    2940
agaacaagac tgctgagttc cagcaatagc acacacatga tgtggtgggt tattgttgcc    3000
attgttgttt ccgttgttgt tgttagtgtt gcctggaact ggcatagttg gaacgaactc    3060
gatcctgtcg atgaaaatct tctgatctcc accggtgatt tggagggtaa tatcaccggt    3120
agaaagcacg ttggtggtgt tgtaaaggtc ctgaagggtg tagtttccgt tctctccaat    3180
cacgtacacg ttaagtggaa gggtgttgtt catgtcggtg gtagagtaaa gggtgaggtt    3240
ggaagaagaa ataagggatc cgttctgggt aatcctaact ccgatttggg tgttggagtt    3300
tgggttggcg tatctgatcc taatcctgta ctgggtagca gtaaggttag tagcggtcat    3360
gaaaaggggt tgccagaat caagtggaac agcagaagcg ccgttaatcc actctttcac    3420
aacggttggc ctagcgttgt ttgggaaata gcccttctca gctggaattc ccttgagaat    3480
cacgttgttg gtatcggaat caagctctcc gaacacgttc tttgggttga gatcgtagga    3540
cacgagagaa gcaagaactc caagcttttcc ggtgtttccc ttcacgttag cctgagtgaa    3600
tgggtaaaga gcgttgatct tctggttggt gtcagatggg ttgcaagaag ccttgtatcc    3660
gttagcggta gaagtgcaag agaatggtgg ttcagttgga gagcatccag tagtgcaata    3720
tcctggaagg gaagctccaa ttccgttaag aatctcgcca tcgaggtact tagagttctg    3780
ggtagcagcg ttaacctgtt gaattggagc ggaaagggta gaaagtcctc caagagactc    3840
tggatcgtta gaatcgccgt acttgtactt ggagttggcg tagttaagca cgaagccgta    3900
tgggtaagag tatccagatc ccttctttgg tggggtgtaa actccaagct caaggttctg    3960
aagctcgtcg ttgtagtagg agatgaggtt cacgttgttg tttgggattg gggagtgctg    4020
gtaagagaat gagtcgaagg tgttgtagat cctgagagat ccgtcagtac cttcttcttg    4080
acccaccatg ttagagaagg tcaccctagt ttgctcaaga gcagtctgag aggtgtaatc    4140
atctgggtaa agggatggcc aaatagccac aatatcgagc acgttcaagg tcatgccctt    4200
gatgtacacg ttgtaggtgt ccacagagaa cttgttggtg ccaatggttg gcatgttctt    4260
ggagtccttg aacaccttca taacctgctg ggtgtagtta aggatagcgt tcctcatgtt    4320
ctgcttggtc ctatcaaggt tagccttctg ggtagtaagt tgagcatcgg aaagtcccac    4380
tttgtcaatc caagcgttgc agaacttgat gtaggattgc atagcagcga atctagcggt    4440
agctccaata acgaagtatg gagcagcagc aacatcgaag tttccgttca tgatgtggtt    4500
ctcgttgttg gcaatatcgc catcagcagc aatgaagttg gtcacaacgt tggtgtaatc    4560
ggactcggtt gggtttctaa gggtcctgtt ggtagtgtta acagttccac tccactgagc    4620
atccacaata gcaccgttga ggttgttgga ggaatcgaag atggactcaa ggtaagagga    4680
ccactcgttc ctatcagcat cgagaagagc cttgttaagc tgcttctgaa tctcggaatc    4740
gatgaggtta atgaggttct cggtatcagc gttcttgttc ttgtgtggcc aaagccatcc    4800
aatcaccatg ttgatgattg gagccacgaa agttccacct ggaacgaagg atccagcaag    4860
agaaattcca gactggagaa gggtaaggta gttgaaggtt ccaccttgag aagcagagaa    4920
tccctgttgg agagcagtaa gagagaaaga tccggtctttt tggaactctt cccaagcctt    4980
cttaagatca cccacggtat cagtaaggga gttcacgtta gaaactggaa tagcgagcac    5040
```

```
gttgtatgga atgttctgct gggactgaag gttgcaatcc atctgttaat cagaaaaact   5100
cagattaatc gacaaattcg atcgcacaaa ctagaaacta acacctgatc tagatagaaa   5160
tcacaaatcg aagagtaatt attcgacaaa actcaaatta tttgaacaaa tcggatgata   5220
tctatgaaac cctaatcgag aattaagatg atatctaacg atcaaaccca gaaaatcgtc   5280
ttcgatctaa gattaacaga atctaaacca agaacatat acgaaattgg atcgaacga    5340 aaacaaaatc gaagatttg agagaataag gaacacagaa atttaccttg atcacggtag    5400
agagaattga gagaaagttt ttaagatttt gagaaattga aatctgaatt gtgaagaaga   5460
agagctcttt gggtattgtt ttatagaaga agaagaagaa aagacgagga cgactaggtc   5520
acgagaaagc taaggcggtg aagcaatagc taataataaa atgacacgtg tattgagcgt   5580
tgtttacacg caaagttgtt tttggctaat tgccttattt ttaggttgag gaaaagtatt   5640
tgtgctttga gttgataaac acgactcgtg tgtgccggct gcaaccactt tgacgccgtt   5700
tattactgac tcgtcgacaa ccacaatttc taacggtcgt cataagatcc agccgttgag   5760
atttaacgat cgttacgatt tatattttt tagcattatc gttttatttt ttaaatatac    5820
ggtggagctg aaaattggca ataattgaac cgtgggtccc actgcattga agcgtatttc   5880
gtattttcta gaattcttcg tgctttattt cttttccttt ttgttttttt ttgccattta   5940
tctaatgcaa gtgggcttat aaaatcagtg aatttcttgg aaaagtaact tctttatcgt   6000
ataacatatt gtgaaattat ccatttcttt taatttttta gtgttattgg atattttgt    6060 atgattattg atttgcatag gataatgact tttgtatcaa gttggtgaac aagtctcgtt   6120
aaaaaaggca agtggtttgg tgactcgatt tattcttgtt attttaattca tatatcaatg   6180 gatcttattt ggggcctggt ccatatttaa cactcgtgtt cagtccaatg accaataata   6240
ttttttcatt aataacaatg taacaagaat gatacacaaa acattctttg aataagttcg   6300
ctatgaagaa gggaacttat ccggtcctag atcatcagtt catacaaacc tccatagagt   6360
tcaacatctt aaacaagaat atcctgatcc ccaaacaatg attaatagat ctaagtcgac   6420
actaagcttt aactagttta ggcctaatga attccaggat ccatactcga gatacccggg   6480
cctgcaggcc taggactgga ttttggtttt aggaattaga aattttattg atagaagtat   6540
tttacaaata caaatacata ctaagggttt cttatatgct caacacatga gcgaaaccct   6600
ataagaaccc taattccctt atctgggaac tactcacaca ttattataga gagagataga   6660
tttgtagaga gagactggtg atttcagcgg acgtcgttaa ctcaatcagc agtaagaaca   6720
cctctacgaa cttggtcacg ctcaatactt tcgaaaagtt gcgcaaagtt ccatgggcca   6780
aagccgtcat ctcctttacg ctgaataaac tcaagaaaa ctggacccat tagtgtctcg    6840
gaaaaaatct gcagaagcaa cctcttatct ccttccacag aacttccatc aagtagtata   6900
cctctagctt ggagctggtc aacgggttca ccgtgatctg gaagtcgtcc ttcgagcatt   6960
tcgtaatagg tatcgggagg tgcagtcata aacctcattc caattttctt cagagcatcc   7020
caagtcttga caagatcgtc tgtcaaaaaa gcaacgtgtt ggattccctc accgttaaac   7080
tgcataagga actcttcgat ttgtccagca cccttagaac tttcctcatt aagaggaatc   7140
ctaatcattc cgtctggtgc tgacatagct ttagaagtta gacctgtgta ttctccctta   7200
atgtcgaaat accttgcctc tctaaagttg aagagtttct catagaagtt agcccaatac   7260
accatccttc ctctatatac attgtgggta aggtgatcga tcactttcaa accagctcca   7320
actggattgc gttcgacacc ttccaagtaa acgaagtcga tatcgtaaat ggaagagccc   7380
tctccgaagc ggtcaataag atacaaagga gcacctccaa ttcccttat ggctggaagg    7440
```

```
ttaagttcca ttggcccagt atcaatgtga attggttggg ctcccagttc caaagcacga    7500
ttatatgcct tctggctatc tttaacccta aaggccattc cacacactga tggaccatgt    7560
tcagcggcaa agtaggaagc aatgctgttt ggctcattgt tcaggattag atttatctct    7620
ccttgtctgt acagatgaac gttcttagac ctgtgggtag cgacctttgt aaacccatt    7680 atttcgaaga taggttcaag agttccagga gtaggagaag caaactcaat aaactcgaag    7740
cccatgagtc ccattgggtt ttcatataaa tctgccatgc accggatcct tccgccgttg    7800
ctgacgttgc cgaggcttct ggaggagcgg cgggcgacgg ggaggctggc ggtggacttg    7860 agccctgga acgagcgac ggcggtggcc gacgaggcca tcatcacggt gggcgccata    7920
gacagcggcg gcaggtacga cagcgtctcg aacttcttgt tgccgtaggc cggccacacc    7980
tgcatatatt gaactcttcc accgttgctg gaagggtgg agaagtcgtt agccttcttg    8040
gtggtgggga aggcggcgtt ggacttaagg ccggtgaacg gagccaccat gttggcctga    8100
gcaggggcgt tccggctaac ggtcgcaact gaggaggaga tcgaagccat tttttttta    8160 attaacacgt gcgttcgtaa atggtgaaaa ttttcagaaa attgcttttg ctttaaaga    8220 aatgatttaa attgctgcaa tagaagtaga atgcttgatt gcttgagatt cgtttgtttt    8280
gtatatgttg tgttgagaat ttattgtcct ctccaaatga aatgaacttc cttatataga    8340
ggaagggtct tgcgaaggat agtgggattg tgcgtcatcc cttacgtcag tggagatatc    8400
acatcaatcc acttgctttg aagacgtggt tggaacgtct tcttttcca cgatgctcct    8460 cgtgggtggg ggtccatctt tgggaccact gtcggtagag gcatcttgaa cgatagcctt    8520
tcctttatcg caatgatggc atttgtagga gccaccttcc ttttccacta tcgcgtccat    8580
gatgctgcga ctatgatcta gttgcttatt ttacgaagca gtaaccctat tccaatagat    8640
ctagttgctt attttgcttg tgctagttgt cgattgagtt attcaaataa accggaatgg    8700
cagtaacaac tccaccagaa gacgacgaac aatcattctc agcagcagcc ggcggcaccg    8760
ccaccctgac ggagaaatta cgactctgt tttctctgcc atcccaatcc ctcaacctgt    8820
aacacaaaga ctgcaagcta tgatcaggca ccgaccctcc aagaaaatcc gaaaccgcta    8880
ttctcgccac tccgatgtct ctcaccactc cggtctccgt cttgcacttc acttcaatcg    8940
tcaagcacct cgcttgcggc cccaactcca ccctgaactt ctcgttccac gtgtggaacc    9000
cgttctcgtt cccgtttgcc atcgccgtcg tgtggctcgt taacgactcc gcgcgaacca    9060
ccgtgaacac gttcttgttc gccggtttac cccttacgtg agaccctcc gcggacaaaa    9120 cagttagctc cagaactttt ggtttggttg ccatgaactg gggattgtga tttacctgtg    9180
aaaccagatt tggatgatgt atcagaattg aataaagaaa aggtgcggtt gcgcctagtt    9240
tttaaacttc accgttgcgc cgcaaaaaat atacagccaa taacttttg acaaaattac    9300 acaattggtc cccaatttat ctctaatttt agatttggtc ccctataat ttaattcaca    9360 aatttggtct ctcaatttta taaattccta caaaattgat cctagaagtt cgatttggac    9420
gttgactatt aacctcaaac gttaactgtc acgtgtgact gttacatgtt aatgtcacgt    9480
atcactgtct gaatggttct ctgaaaaaac ttcatttttt ataggtaaaa ttgtactttt    9540
gattccccaa ttttactcca atttcgattt tgatccccttt ataatttaat ttgcacattt    9600 ggtccccgg ttttataaat ccctttataa attcagtcaa atttcattaa tgaagaagtt    9660
gta                                                                9663
```

<210> SEQ ID NO 24

<211> LENGTH: 1300
<212> TYPE: DNA
<213> ORGANISM: Artificial Sequence
<220> FEATURE:
<223> OTHER INFORMATION: EE-GM5 5' junction
<220> FEATURE:
<221> NAME/KEY: misc_feature
<222> LOCATION: (1)..(1113)
<223> OTHER INFORMATION: part of T-DNA 5' flanking region
<220> FEATURE:
<221> NAME/KEY: misc_feature
<222> LOCATION: (1114)..(1300)
<223> OTHER INFORMATION: part of T-DNA

<400> SEQUENCE: 24

```
cattcttata gacttatagt tttcatagat aatactacta cacacttaat tataaaatcg      60
atcacgagaa cctcacccct ttttttcagcc cactcctcac ttttttctca tgctccacac    120
acaaatcacg ataacctcac cttttgtttt catcactgat cctcacataa atcttttcac    180
attgttaaaa aaacagaaaa ataaaataaa ataaggacaa caagtatata aacgtgtaaa    240
gaagaagaag agaggaacaa aaacttatat gatatatttc taattttaaa ctcagctttt    300
acacactttg aactgttaca caatagctt aaatagagaa attaacaagt ccctaattgg     360
ctgaaactta aagctaatct aaaataggca tcattaacaa atatctacaa attatttttt    420
ctggacacaa tcaacctttt aacaaactta tatcataaaa tctgtagaga tatataaata    480
ttttaacatg atagcaggaa aaatctcaac tgccaactca tatactcaaa aaaccataaa    540
tataatcgtt cactttcctc acaacaacca catacattat acatatagag acagtttag     600 aaatgttgat gacacaccat catttgctta acttttcaaa atcaaattaa agtaattta     660 aggatgtatt tgtcaacaaa ttatacattc aaaagataaa aataattatt tattctttag    720
ttaattctaa ttaaatattc taaaaaagat cgaaagggt atatagtaat ccataaatct     780
tctaagagta ttttcattat attattggct aaatatatta tttatcttaa atttatgagt    840
tttataatga caataatatt aaaaaaaatt acataaaaat ttactctaat gttaaaatta    900
ctaaataaat acttagctta agttttatta aatttaaat tgaaaaaaaa attataataa    960
tcaattaagt aattcactca agaaacacat taatcaaata atcaattcta ataggaaaaa   1020
aatatttaaa tagcactgtt taactttaaa taactcattt gagatgatat gatgattcag    1080
agtcaaatca acatgggtga ctagaaaaaa tcagtactgg gccccttgtgg cgctctatca   1140 tagctataaa cctattcagc acaatgggct cgagggcgat cgctacggga actcgagaag   1200
gatccttaag cttctagttc tagagcggcc gctcgaggaa ttctggattt tagtactgga   1260
ttttggtttt aggaattaga aattttattg atagaagtat                         1300
```

<210> SEQ ID NO 25
<211> LENGTH: 1449
<212> TYPE: DNA
<213> ORGANISM: Artificial Sequence
<220> FEATURE:
<223> OTHER INFORMATION: EE-GM5 3' junction
<220> FEATURE:
<221> NAME/KEY: misc_feature
<222> LOCATION: (1)..(358)
<223> OTHER INFORMATION: part of T-DNA
<220> FEATURE:
<221> NAME/KEY: misc_feature
<222> LOCATION: (359)..(1449)
<223> OTHER INFORMATION: part of T-DNA 3' flanking region

<400> SEQUENCE: 25

```
aaaagaaatg atttaaattg ctgcaataga agtagaatgc ttgattgctt gagattcgtt      60
tgttttgtat atgttgtgtt gagaatttat tgtcctctcc aaatgaaatg aacttcctta     120
tatagaggaa gggtcttgcg aaggatagtg ggattgtgcg tcatcccttg cgtcagtgga     180
gatatcacat caatccactt gctttgaaga cgtggttgga acgtcttctt tttccacgat     240
gctcctcgtg ggtggggggtc catctttggg accactgtcg gtagaggcat cttgaacgat     300
agcctttcct ttatcgcaat gatggcattt gtaggagcca ccttcctttt ccactatcgc     360
gtccatgatg ctgcgactat gatctagttg cttattttac gaagcagtaa ccctattcca     420
atagatctag ttgcttattt tgcttgtgct agttgtcgat tgagttattc aaataaaccg     480
gaatggcagt aacaactcca ccagaagacg acgaacaatc attctcagca gcagccggcg     540
gcaccgccac cctgacggag aaattaacga ctctgttttc tctgccatcc caatccctca     600
acctgtaaca caaagactgc aagctatgat caggcaccga ccctccaaga aaatccgaaa     660
ccgctattct cgccactccg atgtctctca ccactccggt ctccgtcttg cacttcactt     720
caatcgtcaa gcacctcgct tgcggcccca actccaccct gaacttctcg ttccacgtgt     780
ggaacccgtt ctcgttcccg tttgccatcg ccgtcgtgtg gctcgttaac gactccgcgc     840
gaaccaccgt gaacacgttc ttgttcgccg gtttacccct tacgtggaga ccctccgcgg     900
acaaaacagt tagctccaga acttttggtt tggttgccat gaactgggga ttgtgattta     960
cctgtgaaac cagatttgga tgatgtatca gaattgaata agaaaaaggt gcggttgcgc    1020
ctagttttta aacttcaccg ttgcgccgca aaaatatac agccaataac ttttgacaa    1080
aattacacaa ttggtcccca atttatctct aattttagat ttggtcccct tataattaa    1140
ttcacaaatt tggtctctca atttataaa ttcctacaaa attgatccta gaagttcgat    1200
ttggacgttg actattaacc tcaaacgtta actgtcacgt gtgactgtta catgttaatg    1260
tcacgtatca ctgtctgaat ggttctctga aaaaacttca ttttttatag gtaaaattgt    1320
actttttgatt ccccaatttt actccaattt cgatttgat cccttataa tttaattgc    1380
acatttggtc ccccggtttt ataaatccct ttataaattc agtcaaattt cattaatgaa    1440
gaagttgta                                                           1449
```

<210> SEQ ID NO 26
<211> LENGTH: 18
<212> TYPE: DNA
<213> ORGANISM: Artificial Sequence
<220> FEATURE:
<223> OTHER INFORMATION: primer GLPA210

<400> SEQUENCE: 26

```
ctctcaccca gatttcac                                                    18
```

<210> SEQ ID NO 27
<211> LENGTH: 18
<212> TYPE: DNA
<213> ORGANISM: Artificial Sequence
<220> FEATURE:
<223> OTHER INFORMATION: primer GLPA212

<400> SEQUENCE: 27

```
cccatgcggt attatgtg                                                    18
```

<210> SEQ ID NO 28

```
<211> LENGTH: 20
<212> TYPE: DNA
<213> ORGANISM: Artificial Sequence
<220> FEATURE:
<223> OTHER INFORMATION: primer GLPB167

<400> SEQUENCE: 28
tacaacgtgc tcgctattcc                                               20

<210> SEQ ID NO 29
<211> LENGTH: 20
<212> TYPE: DNA
<213> ORGANISM: Artificial Sequence
<220> FEATURE:
<223> OTHER INFORMATION: primer GLPB170

<400> SEQUENCE: 29
tctcggtatc agcgttcttg                                               20

<210> SEQ ID NO 30
<211> LENGTH: 31
<212> TYPE: DNA
<213> ORGANISM: Artificial Sequence
<220> FEATURE:
<223> OTHER INFORMATION: primer PRIM2123

<400> SEQUENCE: 30
gcactgttta actttaaata actcatttga g                                  31

<210> SEQ ID NO 31
<211> LENGTH: 29
<212> TYPE: DNA
<213> ORGANISM: Artificial Sequence
<220> FEATURE:
<223> OTHER INFORMATION: primer PRIM2122

<400> SEQUENCE: 31
caagcaaaat aagcaactag atctattgg                                     29

<210> SEQ ID NO 32
<211> LENGTH: 23
<212> TYPE: DNA
<213> ORGANISM: Artificial Sequence
<220> FEATURE:
<223> OTHER INFORMATION: probe TM2327

<400> SEQUENCE: 32
tttggtgaaa aacaatttgg tgt                                           23

<210> SEQ ID NO 33
<211> LENGTH: 2063
<212> TYPE: DNA
<213> ORGANISM: Glycine max
<220> FEATURE:
<221> NAME/KEY: misc_feature
<222> LOCATION: (1)..(1000)
<223> OTHER INFORMATION: 5' flanking genomic sequence
<220> FEATURE:
<221> NAME/KEY: misc_feature
<222> LOCATION: (1001)..(1063)
<223> OTHER INFORMATION: target site deletion
<220> FEATURE:
<221> NAME/KEY: misc_feature
<222> LOCATION: (1064)..(2063)
<223> OTHER INFORMATION: 3' flanking genomic sequence
```

```
<400> SEQUENCE: 33
tccacacaca aatcacgata acctcacctt ttgttttcat cactgatcct cacataaatc        60
ttttcacatt gttaaaaaaa cagaaaaata aaataaaata aggacaacaa gtatataaac       120
gtgtaaagaa gaagaagaga ggaacaaaaa cttatatgat atatttctaa tttttaactc       180
agcttttaca cactttgaac tgttacaaca atagcttaaa tagagaaatt aacaagtccc       240
taattggctg aaacttaaag ctaatctaaa ataggcatca ttaacaaata tctacaaatt       300
attttttctg gacacaatca acctttttaac aaacttatat cataaaatct gtagagatat      360
ataaatattt taacatgata gcaggaaaaa tctcaactgc caactcatat actcaaaaaa       420
ccataaatat aatcgttcac ttttctcaca acaaccacat acattataca tatagaggac       480
agtttagaaa tgttgatgac acaccatcat ttgcttaact tttcaaaatc aaattaaagt       540
aattttaagg atgtatttgt caacaaatta tacattcaaa agataaaaat aattatttat       600
tctttagtta attctaatta aatattctaa aaaagatcga aagggtata tagtaatcca       660 taaatcttct aagagtattt tcattatatt attggctaaa tatattattt atcttaaatt       720
tatgagtttt ataatgacaa taatattaaa aaaaattaca taaaaattta ctctaatgtt       780
aaaattacta aataaatact tagcttaagt tttattaaat tttaaattga aaaaaaaatt       840
ataataatca attaagtaat tcactcaaga aacacattaa tcaaataatc aattctaata       900
ggaaaaaaat atttaaatag cactgtttaa ctttaaataa ctcatttgag atgatatgat       960
gattcagagt caaatcaaca tgggtgacta gaaaaaatca aatcgacatc aatgtgtgta      1020
caccaaattg tttttcacca aacaataata ataataaaag taatacgaag cagtaaccct      1080
attccaatag atctagttgc ttattttgct tgtgctagtt gtcgattgag ttattcaaat      1140
aaaccggaat ggcagtaaca actccaccag aagacgacga acaatcattc tcagcagcag      1200
ccggcggcac cgccacccctg acggagaaat taacgactcc gttttctctg ccatcccaat      1260
ccctcaacct gtaacacaaa gactgcaagc tatgatcagg caccgaccct ccaagaaaat      1320
ccgaaaccgc tattctcgcc actccgatgt ctctcaccac tccggtctcc gtcttgcact      1380
tcacttcaat cgtcaagcac ctcgcttgcg gccccaactc caccctgaac ttctcgttcc      1440
acgtgtggaa cccgttctcg ttccgtttg ccatcgccgt cgtgtggctc gttaacgact       1500
ccgcgcgaac caccgtgaac acgttcttgt tcgccggttt accccttacg tggagaccct      1560
ccgcggacaa aacagttagc tccagaactt ttggtttggt tgccatgaac tgggattgt       1620 gatttacctg tgaaaccaga tttggatgat gtatcagaat tgaataaaga aaaggtgcgg      1680
ttgcgcctag ttttttaaact tcaccgttgc gccgcaaaaa atatacagcc aataactttt      1740
tgacaaaatt acacaattgg tccccaattt atctctaatt ttagatttgg tcccttata      1800 atttaattca caaatttggt ctctcaattt tataaattcc tacaaaattg atcctagaag      1860
ttcgatttgg acgttgacta ttaacctcaa acgttaactg tcacgtgtga ctgttacatg      1920
ttaatgtcac gtatcactgt ctgaatggtt ctctgaaaaa acttcatttt ttataggtaa      1980
aattgtactt tgattccccc aatttttactc caatttcgat tttgatcccc ttataattta      2040
atttgcacat ttggtccccc ggt                                             2063
```